US011248264B2

(12) United States Patent
Sahin et al.

(10) Patent No.: US 11,248,264 B2
(45) Date of Patent: Feb. 15, 2022

(54) INDIVIDUALIZED VACCINES FOR CANCER

(71) Applicants: TRON-Translationale Onkologie an der Universitätsmedizin der Johannes Gutenberg-Universität Mainz gGmbH, Mainz (DE); BioNTech SE, Mainz (DE)

(72) Inventors: Ugur Sahin, Mainz (DE); Sebastian Kreiter, Mainz (DE); Mustafa Diken, Mainz (DE); Jan Diekmann, Mainz (DE); Michael Koslowski, Oberschleißheim (DE); Cedrik Britten, Mainz (DE); John Christopher Castle, Mainz (DE); Martin Löwer, Mainz (DE); Bernhard Renard, Mainz (DE); Tana Omokoko, Mainz (DE); Johannes Hendrikus De Graaf, Lorzweiler (DE)

(73) Assignees: TRON-Translationale Onkologie an der Universitätsmedizin der Johannes Gutenberg-Universität Mainz gGmbH, Mainz (DE); BioNTech SE, Mainz (DE)

( * ) Notice: Subject to any disclaimer, the term of this patent is extended or adjusted under 35 U.S.C. 154(b) by 0 days.

(21) Appl. No.: 16/920,286

(22) Filed: Jul. 2, 2020

(65) Prior Publication Data
US 2021/0164034 A1    Jun. 3, 2021

Related U.S. Application Data

(62) Division of application No. 14/119,348, filed as application No. PCT/EP2012/002209 on May 23, 2012, now Pat. No. 10,738,355.

(30) Foreign Application Priority Data

May 24, 2011 (WO) ............... PTC/EP2011/002576
Jan. 2, 2012 (WO) ............... PCT/EP2012/000006

(51) Int. Cl.
*A61K 39/00* (2006.01)
*C12Q 1/6869* (2018.01)
*G16B 20/00* (2019.01)
*G16B 40/00* (2019.01)
*C12Q 1/6886* (2018.01)
*G16B 20/20* (2019.01)

(52) U.S. Cl.
CPC ........ *C12Q 1/6869* (2013.01); *A61K 39/0011* (2013.01); *C12Q 1/6886* (2013.01); *G16B 20/00* (2019.02); *G16B 20/20* (2019.02); *G16B 40/00* (2019.02); *A61K 2039/80* (2018.08); *C12Q 2600/156* (2013.01); *Y02A 90/10* (2018.01)

(58) Field of Classification Search
CPC .................................................. A61K 39/0011
See application file for complete search history.

(56) References Cited

U.S. PATENT DOCUMENTS

| | | | |
|---|---|---|---|
| 4,897,355 A | 1/1990 | Eppstein et al. |
| 5,264,618 A | 11/1993 | Felgner et al. |
| 5,703,055 A | 12/1997 | Felgner et al. |
| 6,251,399 B1 | 6/2001 | Diamond et al. |
| 6,472,176 B2 | 10/2002 | Kovesdi et al. |
| 6,500,641 B1 | 12/2002 | Chen et al. |
| 6,586,410 B1 | 7/2003 | Wheeler et al. |
| 7,303,881 B2 | 12/2007 | Huang et al. |
| 7,462,354 B2 | 12/2008 | Sette et al. |
| 7,790,696 B2 | 9/2010 | Gregoriadis |
| 8,140,270 B2 | 3/2012 | Kingsmore et al. |
| 8,217,016 B2 | 7/2012 | Hoerr et al. |
| 8,349,558 B2 | 1/2013 | Fatho et al. |
| 8,703,142 B2 | 4/2014 | Diamond et al. |
| 8,853,283 B2 | 10/2014 | Platscher et al. |
| 8,877,206 B2 | 11/2014 | Chen et al. |
| 9,115,402 B2 | 8/2015 | Hacohen et al. |
| 10,738,355 B2 | 8/2020 | Sahin et al. |
| 2006/0188490 A1 | 8/2006 | Hoerr et al. |
| 2006/0204523 A1 | 9/2006 | Khromykh et al. |

(Continued)

FOREIGN PATENT DOCUMENTS

| | | |
|---|---|---|
| CN | 103608033 B | 6/2016 |
| EP | 0839912 A1 | 5/1998 |

(Continued)

OTHER PUBLICATIONS

Kartikasari et al. (2019, Frontiers in Immunology, vol. 9, pp. 1-15) (Year: 2019).*
Jordan et al. (2010, PNAS, vol. 107(10), pp. 4652-4657). (Year: 2010).*
Nov. 30, 2018—(CA) Office Action—App 2,836,494.
Sep. 25, 2018—(AU) Examination Report—App 2017213515.
Mar. 20, 2019 (EP) Search Report—Appl. 18199105.0.
Abastado et al. J Immunol. 151(7) 3569-75. 1993.
Adzhubei IA et al., Nat Methods 2010;7:248-9.

(Continued)

*Primary Examiner* — Thaian N. Ton
*Assistant Examiner* — David A Montanari
(74) *Attorney, Agent, or Firm* — Choate, Hall & Stewart LLP; Brenda Herschbach Jarrell; Janet M. Tse

(57) ABSTRACT

The present invention relates to the provision of vaccines which are specific for a patient's tumor and are potentially useful for immunotherapy of the primary tumor as well as tumor metastases. In one aspect, the present invention relates to a method for providing an individualized cancer vaccine comprising the steps: (a) identifying cancer specific somatic mutations in a tumor specimen of a cancer patient to provide a cancer mutation signature of the patient; and (b) providing a vaccine featuring the cancer mutation signature obtained in step (a). In a further aspect, the present invention relates to vaccines which are obtainable by said method.

Figure 1:
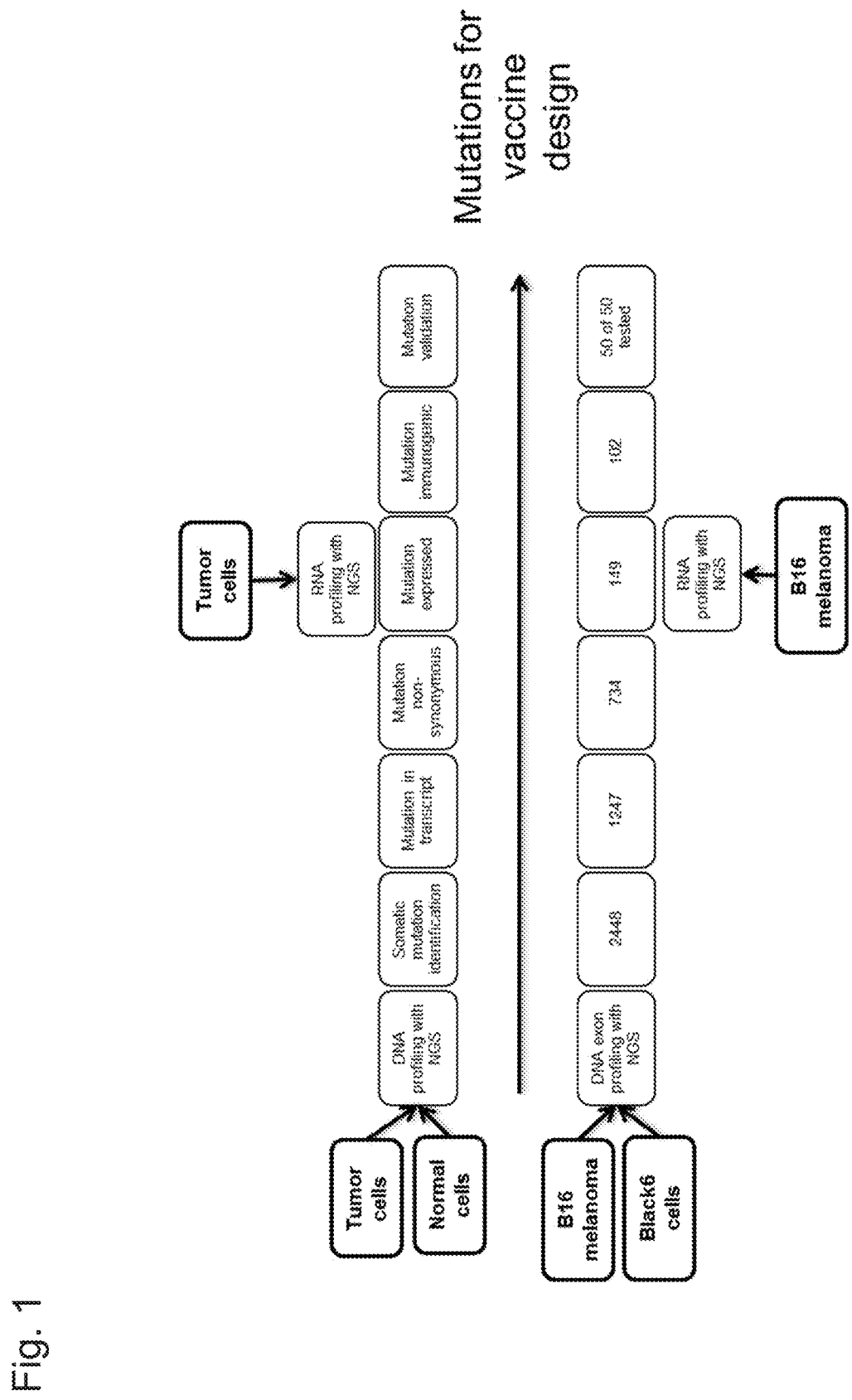

19 Claims, 26 Drawing Sheets
Specification includes a Sequence Listing.

(56) References Cited

U.S. PATENT DOCUMENTS

| | | |
|---|---|---|
| 2007/0025968 A1 | 2/2007 | Van Der Burg et al. |
| 2008/0171711 A1 | 7/2008 | Hoerr et al. |
| 2009/0055944 A1 | 2/2009 | Korman et al. |
| 2009/0217401 A1 | 8/2009 | Korman et al. |
| 2010/0151492 A1 | 6/2010 | Ahmed et al. |
| 2010/0304989 A1 | 12/2010 | Von Hoff et al. |
| 2011/0195090 A1 | 8/2011 | Dimitrov |
| 2011/0257890 A1 | 10/2011 | Weinschenk et al. |
| 2012/0237975 A1 | 9/2012 | Schrum et al. |
| 2013/0115272 A1 | 5/2013 | de Fougerolles et al. |
| 2013/0123481 A1 | 5/2013 | de Fougerolles et al. |
| 2013/0156849 A1 | 6/2013 | de Fougerolles et al. |
| 2013/0203115 A1 | 8/2013 | Schrum et al. |
| 2013/0237593 A1 | 9/2013 | de Fougerolles et al. |
| 2013/0237594 A1 | 9/2013 | de Fougerolles et al. |
| 2013/0244278 A1 | 9/2013 | de Fougerolles et al. |
| 2013/0244279 A1 | 9/2013 | de Fougerolles et al. |
| 2013/0245106 A1 | 9/2013 | de Fougerolles et al. |
| 2013/0245107 A1 | 9/2013 | de Fougerolles et al. |
| 2013/0255281 A1 | 10/2013 | Bray |
| 2013/0266640 A1 | 10/2013 | de Fougerolles et al. |
| 2014/0010861 A1 | 1/2014 | Bancel et al. |
| 2014/0147454 A1 | 5/2014 | Chakraborty et al. |
| 2014/0178438 A1 | 6/2014 | Sahin et al. |
| 2015/0017211 A1 | 1/2015 | de Fougerolles et al. |
| 2015/0030576 A1 | 1/2015 | Bancel |
| 2015/0167017 A1 | 6/2015 | Roy et al. |

FOREIGN PATENT DOCUMENTS

| | | |
|---|---|---|
| EP | 1242108 A1 | 9/2002 |
| EP | 1392341 A2 | 3/2004 |
| EP | 2100620 A1 | 9/2009 |
| EP | 2569633 A2 | 3/2013 |
| EP | 3473267 A1 | 4/2019 |
| JP | 2004527213 A | 9/2004 |
| WO | WO-1994/023031 A1 | 10/1994 |
| WO | WO-96/33739 A1 | 10/1996 |
| WO | WO-97/24447 A1 | 7/1997 |
| WO | WO-97/40156 A1 | 10/1997 |
| WO | WO-1998/014464 A1 | 4/1998 |
| WO | WO-1999/024566 A1 | 5/1999 |
| WO | WO-99/34015 A2 | 7/1999 |
| WO | WO-9934014 A2 | 7/1999 |
| WO | WO-1999/052503 A2 | 10/1999 |
| WO | WO-2000/20029 A1 | 4/2000 |
| WO | WO-2000/067761 A1 | 11/2000 |
| WO | WO-01/19408 A1 | 3/2001 |
| WO | WO-2001/047959 A2 | 7/2001 |
| WO | WO-2001/093902 A2 | 12/2001 |
| WO | WO-02/12281 A2 | 2/2002 |
| WO | WO-2002/048377 A2 | 6/2002 |
| WO | WO-2002/083714 A2 | 10/2002 |
| WO | WO-02/098443 A2 | 12/2002 |
| WO | WO-2003/051401 A2 | 6/2003 |
| WO | WO-03/059381 A2 | 7/2003 |
| WO | WO-2003/068257 A1 | 8/2003 |
| WO | WO-2003/106692 A2 | 12/2003 |
| WO | WO-2004/004743 A1 | 1/2004 |
| WO | WO-2005/028505 A2 | 3/2005 |
| WO | WO-2005/030250 A2 | 4/2005 |
| WO | WO-2005/039533 A1 | 5/2005 |
| WO | WO-2005/040816 A1 | 5/2005 |
| WO | WO-2005/110338 A2 | 11/2005 |
| WO | WO-2006/121168 A2 | 11/2006 |
| WO | WO-2007/024708 A2 | 3/2007 |
| WO | WO-2007/025760 A2 | 3/2007 |
| WO | WO-2007/031222 A2 | 3/2007 |
| WO | WO-2007/036366 A2 | 4/2007 |
| WO | WO-2007/101227 A2 | 9/2007 |
| WO | WO-2007/106545 A2 | 9/2007 |
| WO | WO-2008/080468 A1 | 7/2008 |
| WO | WO-2008/083174 A2 | 7/2008 |
| WO | WO-2008/085562 A2 | 7/2008 |
| WO | WO-2008/116078 A2 | 9/2008 |
| WO | WO-2008/156712 A1 | 12/2008 |
| WO | WO-2009/053041 A2 | 4/2009 |
| WO | WO-2009/118296 A2 | 10/2009 |
| WO | WO-2009/129227 A1 | 10/2009 |
| WO | WO-2010/037395 A2 | 4/2010 |
| WO | WO-2010/037539 A1 | 4/2010 |
| WO | WO-2010/066418 A1 | 6/2010 |
| WO | WO-2011/012316 A2 | 2/2011 |
| WO | WO-2011/143656 A2 | 11/2011 |
| WO | WO-2012/045075 A1 | 4/2012 |
| WO | WO-2012/045082 A2 | 4/2012 |
| WO | WO-2012/135805 A2 | 10/2012 |
| WO | WO-2012/159643 A1 | 11/2012 |
| WO | WO-2012/159729 A1 | 11/2012 |
| WO | WO-2012/159754 A2 | 11/2012 |
| WO | WO-2013/040142 A2 | 3/2013 |
| WO | WO-2013/052523 A1 | 4/2013 |
| WO | WO-2013/090648 A1 | 6/2013 |
| WO | WO-2013/124701 A2 | 8/2013 |
| WO | WO-2013/151663 A1 | 10/2013 |
| WO | WO-2013/151664 A1 | 10/2013 |
| WO | WO-2013/151665 A2 | 10/2013 |
| WO | WO-2013/151672 A2 | 10/2013 |
| WO | WO-2014/012051 A1 | 1/2014 |
| WO | WO-2014/071219 A1 | 5/2014 |
| WO | WO-2014/093924 A1 | 6/2014 |
| WO | WO-2014/144039 A1 | 9/2014 |
| WO | WO-2014/144711 A1 | 9/2014 |
| WO | WO-2014/144767 A1 | 9/2014 |
| WO | WO-2014/152027 A1 | 9/2014 |
| WO | WO-2014/152030 A1 | 9/2014 |
| WO | WO-2014/152031 A1 | 9/2014 |
| WO | WO-2014/152211 A1 | 9/2014 |
| WO | WO-2014/159813 A1 | 10/2014 |
| WO | WO-2014/160243 A1 | 10/2014 |
| WO | WO-2014/164253 A1 | 10/2014 |
| WO | WO-2014/168874 A2 | 10/2014 |
| WO | WO-2015/014375 A1 | 2/2015 |
| WO | WO-2015/034925 A1 | 3/2015 |
| WO | WO-2015/034928 A1 | 3/2015 |
| WO | WO-2015/038892 A1 | 3/2015 |
| WO | WO-2015/043613 A1 | 4/2015 |
| WO | WO-2015/051169 A2 | 4/2015 |
| WO | WO-2015/051173 A2 | 4/2015 |
| WO | WO-2015/058780 A1 | 4/2015 |
| WO | WO-2015/085318 A2 | 6/2015 |
| WO | WO-2015/089511 A2 | 6/2015 |
| WO | WO-2015/117620 A1 | 8/2015 |
| WO | WO-2015/164674 A1 | 10/2015 |
| WO | WO-2015/172843 A1 | 11/2015 |
| WO | WO-2016/062323 A1 | 4/2016 |
| WO | WO-2016/091391 A1 | 6/2016 |
| WO | WO-2016/107877 A1 | 7/2016 |
| WO | WO-2016/155809 A1 | 10/2016 |

OTHER PUBLICATIONS

Agrawal et al., Trend in Biotechnology, 14(10): 376-387, 1996.
Ajay, 5.S. et al., Genome Res. 21,1498-1505 (2011).
Allard WJ. et al. (2004) Clinical Cancer Research 10: 6897-6904.
Aly, Cancer Therapy and Vaccination, Journal of Immunological Methods, Elsevier Science Publishers B.V., Amsterdam, NL, vol. 382, No. 1, May 24, 2012, pp. 1-23.
Anderson, M. and Schrijver, I., Next generation DNA sequencing and the future of genomic medicine, Genes (Basel), 1(1):38-69 (2010).
Azuma et al. 1993: Nature 366, 76-79.
B16 Melanoma, https://en.wikipedia.org/wiki/B16_Melanoma, retrieved from the internet on Sep. 23, 2016, 2 pages.
Bainbridge, M.N. et al., Genome Biol. 11, R62 (2010).
Bansal, V., Bioinformatics 26, 318-324 (2010).
Bei et al. (2010, J. Biomedicine and Biotechnology, pp. 1-12).
Bei et al.J Immunother. May 1998;21(3):159-69.
Bentley, D. et al., Accurate whole human genome sequencing using reversible terminator chemistry, Nature, 456(7218):53-59 (2008). (Author Manuscript).
Berger MF. et al. Integrative analysis of the melanoma transcriptome. Genome Res. Apr. 2010;20(4):413-27.

(56) References Cited

OTHER PUBLICATIONS

Bijker MS et al., J Immunol 2007;179:5033-40.
Bloom MB et al., Exp Med 1997;185:453-9.
Boczkowski et al. (1996). Dendritic cells pulsed with RNA are potent antigen-presenting cells in vitro and in vivo, J Exp. Med. 184: 465-472.
Bogojeska et al. Rtreemix: an R package for estimating evolutionary pathways and genetic progression scores Bioinformatics, vol. 24; No. 20, 2008; pp. 2391-2392.
Bowerman, NA. Engineering the binding properties of the T cell receptor: peptide: MHC ternary complex that governs T cell activity. Mal. Immun. 46: 3000-3008, 2009.
Breiman, L., Statisl. Sci. 16,199-231 (2001).
Brennick et al., Neoepitopes as cancer immunotherapy targets: key challenges and opportunities, Immunotherapy 2017); 9(4); 361-371.
Brickner et al. J Exp. Med 193(2) 195-205 (2001).
Brinckerhoff, L. et al., Melanoma vaccines, Current Opinion Oncology, 12(2):163-173 (2000).
Buckwalter, M. and Srivastava, P., "It is the antigen(s), stupid" and other lessons from over a decade of vaccitherapy of human cancer, Semin Immunol, 20(5):296-300 (2008).
Byers, T. (CA Cancer Journal, 1999, 49: 353-361).
Cai et al., Peptides Derived from Mutated BCR-ABL Elicit T Cell Immunity in CML Patients, Blood, vol. 116, issue 21, pp. 388-388, published Nov. 19, 2010.
Campbell et al. 2010: Nature 467 (7319), 1109-1113.
Canadian Office Action issued in related Canadian Application No. 2,836,494, dated Mar. 28, 2018.
Carbone et al. (J Clin Oncol, 2005, 23: 5099-5107).
Carralot, J. et al., Production and characterization of amplified tumor-derived cRNA libraries to be used as vaccines against metastatic melanomas, Genetic Vaccines and Therapy, 3(6): 10 pages (2005).
Carter, P. et al., Identification and validation of cell surface antigens for antibody targeting in oncology, Endocrine-Related Cancer, 11(4):659-687 (2004).
Chang, S. et al., Peptide length-based prediction of peptide-MHC class II binding, Bioinformatics, 22(22):2761-2767 (2006).
Chapman et al., Applications of Next-Generation Sequencing to Blood and Marrow Transplantation, Biology of Blood and Marrow Transplantation 2012 Elsevier Inc. USA, vol. 18, No. 1, Jan. 2012.
Chenchik, A., Y et al. 1998. Generation and use of high quality cDNA from small amounts of total RNA by SMART PCR. In Gene Cloning and Analysis by RT-PCR. P. L. J. Siebert, ed. BioTechniques Books, MA, Natick. 305-319.
Chmielecki et al. (2010, Nucleic Acids Research, pp. 1-12).
Choi et al. 2009: Proc. Natl. Acad. Sci USA 106, 19096-19101.
Communication (1) of a notice of opposition for EP12723117.3, 34 pages (Apr. 20, 2020).
Communication (2) of a notice of opposition for EP12723117.3, 34 pages (Apr. 20, 2020).
Communication of a notice of opposition for EP12723117.3, 33 pages (Apr. 17, 2020).
Communication pursuant to Rule 113(2) EPC issued in related European Application No. 12723117.3, dated Mar. 13, 2018.
Conry et al. (1994). Immune response to a carcinoembryonic antigen polynucleotide vaccine, Cancer Res. 54:1164-1168.
Conry et al. (1995). Characterization of a messenger RNA polynucleotide vaccine vector, Cancer Res. 55: 1397-1400.
Cornelis J.M. Melief et al., Immunotherapy of established (pre)malignant disease by synthetic long peptide vaccines, Nature Reviews Cancer, vol. 8, No. 5, May 1, 2008.
Coulie et al. (1995). A mutated intron sequence codes for an antigenic peptide recognized by cytolytic T lymphocytes on a human melanoma, Proc. Natl. Acad. Sci. USA 92: 7976-7980.
Dahl et al., Multigene amplification and massively parallel sequencing for cancer mutation discovery, PNAS, 2007, vol. 104, pp. 9387-9392.
Datta SK et al., J Immunol 2003; 170:4102-10.
Decision Revoking the European Patent (Art. 101(2) and 101(3)(b) EPC) for EP11781409.5 (EP 2569633B) and associated documents, 39 pages (Nov. 5, 2018).
Del Val et al., Cell, vol. 66, Issue 6, Sep. 20, 1991, pp. 1145-1153.
Dengjel, J et al. Glycan side chains on naturally presented MHC class II ligands J Mass Spectrom, 2005.
Dennis (Nature. Aug. 7, 2006; 442: 739-741).
DePristo, M.A. et al., Nature Genetics 43, 491-498 (2011).
Dey Net al., Cancer Res 2008;68:1862-71.
Ding et al. Genome remodeling in a basal-like breast cancer metastasis and xenograft Nature, 464: 999-1005, 2010.
Ding et al., Multiepitope Peptide-Loaded Virus-Like Particles as a Vaccine Against Hepatitis B Virus-Related Hepatocellular Carcinoma, Hepatology, vol. 49, No. 5, 2009, 1492-1502.
Ding L et al., Hum Mol Genet 2010; 19:R188-R196.
Dolgin, Nature 522:26.
Dolgin, The Billion-Dollar Biotech, Nature, vol. 522, pp. 26-28, Jun. 4, 2015.
Druley, T.E. et al., Nature Methods 6, 263-265 (2009).
Echchakir H et al., Cancer Res 2001;61:4078-83.
Ecke, T. et al., TP53 Gene Mutations in Prostate Cancer Progression, Anticancer Research, 30:1579-1586 (2010).
European Communication Pursuant to Rule 114(2) issued in related European Application No. 12723117.3, dated Apr. 5, 2018.
European Office Action issued in related European Application No. 12723117.3, dated Apr. 5, 2018.
Ewen, KR. et al., Am. J_ Hum. Genet. 67, 727-736 (2000).
Fawcett et al., An introduction to ROG analysis, Patiern Recognition Letters, Elsevier, Amsterdam, NL, vol. 27, No. 8, Jun. 1, 2006.
Fotin-Mleczek et al., Messenger RNA-based Vaccines With Dual Activity Induce Balanced TLR-7 Dependent Adaptive Immune Responses and Provide Antitumor Activity, J. Immunotherapy; vol. 34, No. 1, Jan. 2011, pp. 1-15.
Fritsch, E. F. et al. HLA-Binding Properties of Tumor Neoepitopes in Humans Cancer Immunology Research, 2: 522-529, 2014.
Frumkin D. et al. (2008) Cancer Research 68: 5924.
Fujita, P.A. et at., Nucleic Acids Res. 39, 876-882 (2011).
Giorgio Parmiani et al., Unique human tumor antigens: immunobiology and use in clinical trials., The Journal of Immunology, vol. 178, No. 4, Feb. 1, 2007.
Gjertsen et al., Mutated ras peptides as vaccines in immunotherapy of cancer, VOX Sanguinis, S. Karger AG, Basel, CH, vol. 74, No. 2, Jan. 1, 1998.
Gnirke A et al., Nat Biotechnol 2009;27: 182-9.
Gnirke, A. Solution hybrid selection with ultra-long oligonucleotides for massively parallel targeted sequencing Nat. Biotechnol, 2009.
Goya, R. et al. SNVMix: predicting single nucleotide variants from next-generation sequencing of tumors, Bioinformatics Bioinformatics, 26: 730-736, 2010.
Gryaznov et al., Biochim. Biophys. Acta, 1489:131-140, 1999.
Gubin, M. et al., Checkpoint blockade cancer immunotherapy targets tumour-specific mutant antigens, Nature, 515(7528):577-581 (2014). (Author Manuscript).
Gura (Science. 1997; 278: 1041-1042).
Guyre et al., Cancer Immunother (1997) 45:146-148.
Hacohen Declaration dated Feb. 16, 14 filed in U.S. Appl. No. 13/108,610, 10 pages.
Hacohen, N. et al., Getting Personal with Neoantigen-Based Therapeutic Cancer Vaccines, Cancer Immunol Res, 1:11-15 (2013). (Author Manuscript).
Hajra KM et al., Apoptosis 2004;9:691-704.
Han Chang et al., Exome Sequencing Reveals Comprehensive Genomic Alterations across Eight Cancer Cell Lines, PLOS ONE, vol. 6, No. 6, Jan. 1, 2011.
Hansen, KO., et al., Nucleic. Acids. Res. 38, e131 (2010).
Hart et al. (2010, Methods in Enzymology, vol. 472, pp. 407-430).
Hodges et al. 2007: Nat. Genet. 39,1522-1527.
Hoerr et al. (2000). In vivo application of RNA leads to induction of specific cytotoxic T lymphocytes and antibodies, Eur. J Immunol. 30: 1-7.
Holtkamp, S et al., Blood, 108: 4009-4017, 2006.
Hoyt MA et al. (2006). EMBO J 25 (8): 1720-9.

(56) References Cited

OTHER PUBLICATIONS

International Preliminary Report on Patentability Chapter I, dated Nov. 26, 2013, Filed in relation to PCT Application No. PCT/EP2011/002576, Filed May 24, 2011, Entitled Individualized Vaccines for Cancer, By Applicant BIONTECH AG, 7 pages.
International Preliminary Reporton Patentability Chapter I, dated Nov. 26, 2013, Filed in relation to PCT Application No. PCT/EP2012/002209, Filed May 23, 2012, Entitled Individualized Vaccines for Cancer, By Applicant BIONTECH AG, 14 pages.
International Search Report for International Patent Application No. PCT/EP2011/002576 dated Apr. 5, 2012.
International Search Report for International Patent Application No. PCT/EP2012/002209 dated May 8, 2013.
International Search Report for PCTIEP2013/003559 dated Feb. 4, 2014.
International Search Report issued in related International Application No. PCT/US2015/049491, dated Dec. 23, 2015.
J. C. Castle et al., Exploiting the mutanome for tumor vaccination, Cancer Research, Jan. 1, 2012.
Japanese Office Action issued in related Japanese Application No. 2014-511773, dated Mar. 19, 2018.
Japanese Office Action issued in related Japanese application No. 2016-172519, dated April 2, 2018.
Jia et al.. Genome-scale search of tumor-specific antigens by collective analysis of mutations, expressions and T-cell recognition, Molecular Immunology, Pergamon, GB, vol. 46, No. 8-9, May 1, 2009.
Jiang et al. Construction of Evolutionary Tree Models for Renal Cell Carcinoma from Comparative Genomic Hybridization Data Cancer Research; 60, pp. 6503-6509, Nov. 15, 2000.
Johanning et al. Nucleic Acids Res. May 11, 1995; 23(9): 1495-1501.
John D. Storey, A direct approach to false discovery rates, PLOS Computational Biology, vol. 64, No. 3, pp. 479-498, Aug. 1, 2002.
Kawakami, Y. et al., Identification of human tumor antigens and its implications for diagnosis and treatment of cancer, Cancer Sci, 95(10):784-791 (2004).
Kenter, G. G. et al. Phase I Immunotherapeutic Trial with Long Peptides Spanning the E6 and E7 sequences of High-risk human papillomavirus 16 in End-stage cervical cancer patients shows low toxicity and robust immunogenicity. Clinical Cancer Research, 14:169-177, 2008.
Keogh, E. et al. Identification of New Epitopes from Four Different Tumor-Associated Antigens: Recognition of Naturally Processed Epitopes Correlates with HLA-A *0201-Binding Affinity, J. Immunol. 167: 787-796, 2001.
Kessler J H et al., Identification of T-cell epitopes for cancer immunotherapy, Leukemia, MacMillan Press Ltd, vol. 21, No. 9, Sep. 1, 2007.
Kircher, M. et al., Genome Biol. 10, R83 (2009). Epub Aug. 14, 2009.
Kreiter et al., Cancer Immunol lmmunother2007;56:1577-87.
Kreiter et al., Intranodal Vaccination with Naked Antigen-Encoding RNA Elicits Potent Prophylactic and Therapeutic Antitumoral Immunity, Microenvironment and Immunology; 2010; pp. 9031-9039.
Kreiter et al., Mutant MHC class II epitopes drive therapeutic immune responses to cancer, Nature, 520, Apr. 30, 2015, 17 pages.
Kreiter S et al., Cancer Res 2010; 70:9031-40.
Kreiter, S. et al., J.Immunol., 180: 309-318, 2008.
Krieg et al., 1995, Nature 374: 546-549.
Kronenberger, K. et al., A polyvalent cellular vaccine induces T-cell responses against specific self-antigens overexpressed in chronic lymphocytic B-cell leukemia, J Immunother, 31(8):723-730 (2008).
Kuhn, A. N. et al., Gene Ther., 17: 961-971, 2010.
Kumar P et al., Nat Protoc 2009;4:1073-81.
Langmead B et al., Genome Biol 2009; 10:R25.
Lassmann.T. et al., Bioinformatics 27, 130-131 (2011).
Ledford (2015). Cancer mutations often misidentified in the clinic, Nature News, 3 pages.
Lee YM et al., Gene 2010;466:16-25.

Lemmel, Claudia et al., Differential quantitative analysis of MHC ligands by mass spectrometry using stable isotope labeling Nat Biotechnol, 2004.
Lennerz et al. (2005). The response of autologous T cells to a human melanoma is dominated by mutated neoantigens, Proc. Natl. Acad. Sci. USA 102: 16013-16018.
Ley et al. (2008). DNA sequencing of a cytogenetically normal acute myeloid leukaemia genome, Nature 456: 66-72.
Li et al., Cancer Genome Sequencing and Its Implications for Personalized Cancer Vaccines, Cancers, 3, 4191-4211, 2011.
Li H and Durbin R, Bioinformatics 2009;25: 1754-1760.
Li, H. et al., Bioinformatics 25, 2078-2079 (2009).
Li, H., BioinJormatics27,1157-1158 (2011).
Linard, B. et al., A ras-mutated peptide targeted by CTL infiltrating a human melanoma lesion, J Immunol., 168(9):4802-4808 (2002).
International Preliminary Reporton Patentability for PCT/EP2012/002209 dated Nov. 26, 2013.
Luigi Buonaguro et al., Translating Tumor Antigens into Cancer Vaccines, Clinical and Vaccine Immunology, vol. 18, No. 1, Jan. 1, 2011, pp. 23-34.
Lundegaard, C. et al., Nelsen M. State of the art and challenges in sequence based T-cell epitope prediction, Immunome Res., 6 Suppl 2(Suppl 2):S3 (2010).
Lundegaard, C., et al., NetMHC-3.0: accurate web accessible predictions of human, mouse and monkey MHC class I affinities for peptides of length 8-11, Nucleic Acids Res., 36:W509-W512 (2008).
Lutz MB et al., J Immunol Methods 1999;223:77-92.
Mahvi et al., Immunology and Cell Biology 75: 456-460, 1997.
Maksyutovand Zagrebelnaya (1993). ADEPT: a computer program for prediction of protein antigenic determinants, Comput. Appl. Biosci. 9: 291-297.
Malcikova, J. et al., Identification of somatic hypermutations in the TP53 gene in B-cell chronic lymphocytic leukemia, Mol Immunol., 45(5):1525-1529 (2008).
Maloy et al. (2001), Proc Natl Acad Sci USA 98:3299-303.
Mandelboim et al. (1995). Regression of established murine carcinoma metastases following vaccination with tumour-associated antigen peptides, Nature Medicine 1: 1179-1183.
Mardis, E. et al., Cancer genome sequencing: a review, Hum Mal Gen, 18:R163-R168 (2009).
Mardis, ER., Recurring Mutations Found by Sequencing an Acute Myeloid Leukemia Genome, New England J. Med., 361:1058-1066 (2009).
Margulies, Marcel et al., Genome Sequencing in Open Microfabricated High Density Picoliter Reactors Nature, 2005.
Martin Lower et al. Confidence-Based Somatic Mutation of Evaluation and Prioritization. PLOS Computational Biology, vol. 8, Issue 9, Sep. 27, 2012.
Martinon et al. (1993). Induction of virus-specific cytotoxic T lymphocytes in vivo by liposome-entrapped mRNA. Eur. J. Immunol 23, 1719-1722.
Mateo et al., An HLA-A2 polyepitope vaccine for melanoma immunotherapy, The Journal of Immunology, The American Association of Immunologists, US, vol. 163, No. 7, Oct. 1, 1999.
Mayer et al., Anticancer Research 25:3917-3924 (2005).
McGranahan et al. (2016). Clonal neoantigens elicit T cell immunoreactivity and sensitivity to immune checkpoint blockade, Science. 351(6280):1463-9.
McKenna A et al, Genome Res 2010;20: 1297-303.
Meleif, C. and Van Der Burg, S., Immunotherapy of established (pre)malignant disease by synthetic long peptide vaccines, Nature Reviews, 8:351-360 (2008).
Men, Y. et al., Assessment of Immunogenicity of Human Melan-A Peptide Analogues in HLA-A*0201/Kb Transgenic Mice, The Journal of Immunology, 162(6):3566-3573 (1999).
Mexican Office Action issued in related Mexican application No. MX/a/2013/0136590, dated Nov. 14, 2017.
Meyerson, M. et al. Advances in understanding cancer genomes through second-generation sequencing Nature Rev. Genetics. 11:685-695, 2010.
Monach et al. (1995). A unique tumor antigen produced by a single amino acid substitution, Immunity 2: 45-59.

(56) References Cited

OTHER PUBLICATIONS

Monica Bocchia et al., Antitumor Vaccination: Where We Stand, Haematologica, The Hematology Journal; Official Organ of the European Hematology Association, Fondazione Ferrata Storti, Rome, IT, vol. 85, No. 11, Nov. 1, 2000, pp. 1172-1206.
Mortazavi (2008). Mapping and quantifying mammalian transcriptomes by RNA-Seq, Nature Methods 5: 621-628.
Mortazavi A et al., Nat Methods 2008,5:621 -8.
N. H. Segal et al., Epitope Landscape in Breast and Colorectal Cancer, Cancer Research, vol. 68, No. 3, Feb. 1, 2008.
Nagrath et al., 2007: Nature 450, 1235-1239.
Nakamura, K et al., Acids Res.(2011).
Naterston RH et al., Nature 2002;420:520-62.
Nature 420,520-562 (2002).
Navin et al. (2011, Nature, vol. 472, pp. 90-95).
Nei X et al., Nat Genet 2011 ;43:442-6.
Neide et al. 2005: J_ Immunother. 31, 180-188.
Neinschenk et al. (2002). Integrated functional genomics approach for the design of patient-individual antitumor vaccines, Cancer Res 62: 5818-5827.
New Zealand Office Action issued in related New Zealand application No. 718326, dated Dec. 8, 2017.
Ng, PC et al., PLoS Gen., 4(8): 1-15, 2008.
Nielsen et al., An in vitro-transcribed-mRNA polyepitope construct encoding 32 distinct HLA class I-restricted epitopes from CMV, EBV, and Influenza for use as a functional control in human immune monitoring studies, Journal of Immunological Methods 360 (2010) 149-156.
Nolff et al. (1990). Direct gene transfer into mouse muscle in vivo, Science 247: 1465-1468.
Nood et al. (2007). The genomic landscapes of human breast and colorectal cancers, Science 318: 1108-1113.
Nortzel et al. (1983). Multiple tumour-specific antigens expressed on a single tumour cell, Nature 304: 165-167.
Nothnagel, M. et al., Hum. Genet. Feb. 23, 2011.
Notice of Opposition to EP 2569633 B (Application No. EP11781409.5) and associated documents (Agenus Inc.), 20 pages (Nov. 9, 2016).
Notice of Opposition to EP 2569633 B (Application No. EP11781409.5) and associated documents (Dr. Christian Muller), 49 pages (Nov. 9, 2016).
Notice of Opposition to EP 2569633 B (Application No. EP11781409.5) and associated documents (Gritstone Oncology, Inc.), 53 pages (Nov. 7, 2016).
Notice of Opposition to EP 2569633 B (Application No. EP11781409.5) and associated documents (James Poole Limited), 35 pages (Nov. 9, 2016).
Notice of Opposition to EP 2569633 B (Application No. EP11781409.5) and associated documents (Strawman Limited) , 39 pages (Nov. 10, 2016).
Novellino et al., A listing of human tumor antigens recognized by T cells: Mar. 2004 update, Cancer Immunol mmunother, 2005, 54: 187-207.
Office Action issued in related European Application No. 12723117.3, dated Nov. 13, 2017.
Ott, P. et al., Vaccines and melanoma, Hematol Oncol Clin North Am, 28(3):559-569 (2014).
Pantel K. et al., Circulating tumour cells in cancer patients: challenges and perspectives, Trends in Molecular Medicine, Elsevier Current Trends, GB, vol. 16, No. 9, Sep. 1, 2010.
Parker et al., J Immunol. 152 (1994), 163-175.
Parkhurst, MR. et al. Improved Induction of Melanoma-reactive CTL with peptides from the melanoma antigen gp100 modified at HLA-A*0201-binding residues. J Immunol. 157: 2549-2548, 1996.
Parmiani, G. et al. Unique Human Tumor Antigens: Immunobiology and Use in Clinical Trials. The Journal of Immunology, 178:1975-1979, 2007.
Pascolo, S., Messenger RNA-based vaccines, Expert Opin. Biol. Ther., 4(8):1285-1294 (2004).
Perissi et al., Electron Spin Resonance and Differential Scanning Calorimetry as Combined Tools for the Study of Liposomes in the Presence of Long Chain Nitroxides, 106 J_ of Phys. Chem. B 10468 (2002).
Pfohl et al., Biological Polyelectrolyte Complexes in Solution and Confined on Patterned Surfaces, 198-200 Colloids & Surfaces A: Physicochemical and Eng. Aspects 613 (2002).
Pilla, L. et al. Multipeptide vaccination in cancer patients Expert Opinion on Biological Therapy, 9: 1043-1055, 2009.
Pleasance, E. et al. A small-cell lung cancer genome with complex signatures of tobacco exposure. Nature, 463: 184-190, 2010.
Pleasance, E. et al., A comprehensive catalogue of somatic mutations from a human cancer genome, Nature, 463:191-196 (2010).
Pokrovskaya and Gurevich (1994, Anal. Biochem. 220: 420-423.
U.S. Appl. No. 61/334,866, filed May 14, 2010.
Pruitt KO et al., Nucleic Acids Res 2007;35:061-065.
Qin et al. (2006). Enhancement of antitumour immunity by a novel chemotactic antigen DNA vaccine encoding chemokines and multiepitopes of prostate-tumour-associated antigens, Immunology, 117(3):419-30.
Qin et al., Enhancement of antitumour immunity by a novel chemotactic antigen DNA vaccine encoding chemokines and multiepitopes of prostate-tumour-associated antigens, Immunology, 2006, 117, 419-430.
Rahma Osama et al., A pilot clinical trial testing mutant van Hippel-Lindau peptide as a novel immune therapy in metastatic renal Cell Carcinoma, Journal of Translational Medicine, Biomed Central, London, GB, vol. 8, No. 1, Jan. 28, 2010.
Rajasagi, M. et al., Systematic identification of personal tumor-specific neoantigens in chronic lymphocytic leukemia, Blood, 124(3):453-462 (2014).
Rammensee (2006). Some considerations on the use of peptides and mRNA for therapeutic vaccination against cancer, Immunol Cell Biol. 84(3):290-4.
Rammensee et al. (2008). Cancer Vaccines: Some Basic Considerations, In Genomic and Personalized Medicine, vol. 1 (Eds.: Willard et al.), Elsevier, 573-589.
Rammensee et al., Immunogenentics, 50 (1999), 213-219.
Rammensee et al., Towards patient-specific tumor antigen selection for vaccination, Immunological Reviews, 2002, vol. 188, pp. 164-176.
Rao (1994). Epitope-based vaccines: One step at a lime, Proc. Indian natn. Sci. Acad. B60: 419-424.
Rao CG. et al. (2005) International Journal of Oncology 27: 49.
Reagan-Shaw et al. (FASEB J, 2007, 22: 659-61).
Ressing, M. et al. Human CTL epitopes encoded by human papillomavirus types 16E6. J Immunol. 154:5934-5943, 1995.
Rizvi, N. et al. Mutational landscape determines sensitivity to PD-1 blockade in non-small cell lung cancer, Cancer Immunology, 348(6230):124-128 (2014).
Robbins, P. et al., A mutated beta-catenin gene encodes a melanoma-specific antigen recognized by tumor infiltrating lymphocytes, J Exp Med., 183(3):1185-1192 (1996).
Ronaghi et al. 1998: A sequencing method based on real-lime pyrophosphate.
Roopa Srinivasan et al., Tumor Antigens for Cancer Immunotherapy: Therapeutic Potential of Xenogeneic DNA Vaccines Journal of Translational Medicine, Biomed Central, London, GB, vol. 2, No. 1, Apr. 16, 2004, p. 12.
Russian Search Report issued in related Russian Application No. RU2013157150A dated Jul. 5, 2018.
Saenz-Badillos et al. (2001). RNA as a tumor vaccine: a review of the literature, Exp Dermatol. 10(3):143-54.
Saeterdal, I. et al., Frameshift-mutation-derived peptides as tumor-specific antigens in inherited and spontaneous colorectal cancer, Proc Natl Acad Sci USA, 98(23):13255-13260 (2001).
Sahin et al. (2017). Personalized RNA mutanome vaccines mobilize poly-specific therapeutic immunity against cancer, Nature. 13;547(7662):222-226.
Sahin, U. and Tureci, O., Personalized vaccines for cancer immunotherapy, Science, 359:1355-1360 (2018).

(56) References Cited

OTHER PUBLICATIONS

Sampson, J. et al., An epidermal growth factor receptor variant III-targeted vaccine is safe and immunogenic in patients with glioblastoma multiforme, Mol Cancer Ther., 8(10):2773-2779 (2009). (Author Manuscript).
Schaffner, C. et al., Somatic ATM mutations indicate a pathogenic role of ATM in B-cell chronic lymphocytic leukemia, Blood, 94(2):748-753 (1999).
Scheibenbogen, C. et al., Analysis of the T cell response to tumor and viral peptide antigens by an IFNγ—ELISPOT assay, Int. J. Cancer, 71:932-936 (1997).
Schietinger et al., Specificity in cancer immunotherapy, Semin Immunol., 2008, 20(5):276-285, Oct. 2008.
Schlessinger et al. Proteins 61 (1) 115-26. 2005.
Schreurs MW et al. Cancer Res 2000;60:6995-7001.
Schulz O et al., Nature 2005;433:887-92.
Schwitalle, Y. et al., Immunogenic peptides generated by frameshift mutations in DNA mismatch repair-deficient cancer cells, Cancer Immun., 4:14, 10 pages (2004).
Science 268:1432-1434, 1995.
Sebastian Kreiter et al., Targeting the Tumor Mutanome for Personalized Vaccination Therapy, OncoImmunology 2012 Landes Bioscience USA, vol. 1, No. 5, pp. 768-769, Aug. 8, 2012.
Sebastian Kreiter et al., Tumor vaccination using messenger RNA: prospects of a future therapy. Current Opinion in Immunology, vol. 23, No. 3, pp. 399-406, Apr. 13, 2011.
Segal et al. (2008). Epitope landscape in breast and colorectal cancer, Cancer Res. 68: 889-892.
Sensi and Aanichini, Unique Tumor Antigens: Evidence for Immune Control of Genome Integrity and Immunogenic Targets for T cell-mediated Patient-Specific Immunotherapy, Clin. Cancer Res. 2006:12(17), 5023.
Sensi et al., Unique Tumor Antigens: Evidence for Immune Control of Genome Integrity and Immunogenic Targets for T Cell—Mediated Patient-Specific Immunotherapy, Clinical Cancer Research; 2006; 12(17) Sep. 1, 2006, pp. 5023-5032.
Sette, A. et al. Peptide Binding to the Most Frequent HLA-A Class I Alleles Measured by Quantitative Molecular Binding Assays Mol. Immunol. 31: 813-822, 1994.
Sette, A. et al. The Relationship Between Class I Binding Affinity and Immunogenicity of Potential Cytotoxic T cell Epitopes. J Immunol. 153: 5586-5592, 1994.
Shah et al. (2009). Mutation of FOXL2 in granulosa-cell tumors of the ovary, N. Eng. J Med. 360: 2719-2729.
Sherry, S.T. et al., Nucleic Acids Res. 29, 308-311 (2009).
Singh-Jasuja, H. et al., The Tubingen approach: identification, selection, and validation of tumor-associated HLA peptides for cancer therapy, Cancer Immunol Immunother., 53:187-195 (2004).
Sjoblom et al. (2006). The consensus coding sequences of human breast and colorectal cancers, Science 314: 268-274.
Smith et al., Human Dendritic Cells Genetically Engineered to Express a Melanoma Polyepitope DNA Vaccine Induce Multiple Cytotoxic T-Cell Responses, Clinical Cancer Research, vol. 7, 4253-4261, Dec. 2001.
So et al., 1997, Mol. Cells 7: 178-186.
Srivastava, N. and Srivastava, P., Modeling the Repertoire of True Tumor-Specific MHC I Epitopes in a Human Tumor, Pios One, 4:1-7 (2009).
Stephens et al. (2005). A screen of the complete protein kinase gene family identifies diverse patterns of somatic mutations in human breast cancer, Nature Genetics, 37: 590-592.
Stratton, M. et al., The cancer genome, Nature, 458(7239):719-724 (2009) (Author Manuscript).
Su MW et al., J Immunol 1993; 151 :658-67.
Suhrbier, Andreas, Multi-epitope DNA vaccines, Immunology and Cell Biology, 75:402-408 (1997).
Suhrbier, Andreas, Polytope vaccines for the codelivery of multiple CD8 T-cell epitopes, Expert Rev. Vaccines, 1(2):207-213 (2002).
Suzuki et al. 2007: Mol. Oncol. 1 (2), 172-180.
Taub, M.A. et al., Genome Med. 2, 87 (2010).
Teer and Mullikin 2010: Human Mol Genet 19 (2), R145-51.
Thomson et al., J Virology (1998), 72(3):2246-2252.
Tobias Sjoblom et al., The Consensus Coding Sequences of Human Breast and Colorectal Cancers, Science, American Association for the Advancement of Science, Washington, DC, US, vol. 314, Oct. 13, 2006.
Toes et al. (1997). Protective anti-tumor immunity induced by vaccination with recombinant adenoviruses encoding multiple tumor-associated cytotoxic T lymphocyte epitopes in a string-of-beads fashion, Proc. Natl. Acad. Sci. USA 94:14660-14665.
Toes RE et al., J Immunol 1996;156:3911-8.
Tong, J. C. et al., Methods and protocols for prediction of immunogenic Briefings in Bioinformatics, 8(2):96-108 (2006).
Tourdot, S. et al., A general strategy to enhance immunogenicity of low-affinity HLA-A2.1-associated peptides: implication in the identification of cryptic tumor epitopes, Eur. J. Immunol., 30(12):3411-3421 (2000).
UniProtKB—P36888 (FLT3_HUMAN), last sequence update: Aug. 21, 2007.
UniProtKB—Q5SW79 (CE170_HUMAN), last sequence update: Dec. 21, 2004.
UniProtKB—Q9NVD7 (PARVA_Human), last sequence update: Oct. 1, 2000.
UniProtKB, "Print-outs from the UniProtKB database concerning the CEP170, PARVA and FLT3 genes."
Van der Bruggen et al. (1991). A gene encoding an antigen recognized by cytolytic T lymphocytes on a human melanoma, Science 254: 1643-1647.
Van Laere AS, Nguyen M, Braunschweig M. et al. A regulatory mutation in IGF2 causes a major QTL effect on muscle growth in the pig. Nature. 2003;425(6960):832-836.
Van Rooij, N. et al., Tumor exome analysis reveals neoantigen-specific T-cell reactivity in an ipilimumab-responsive melanoma, J Clin Oncol., 31(32):e439-e442 (2013). (Author Manuscript).
Van Tassell, C.P. et al., Nature Methods 5, 247-252 (2008).
Verhaak RG et al., Cancer Cell 2010;17:98-110.
Voelkerding et al. 2009: Next generation sequencing: From basic research to diagnostics. Clinical chemistry 55,641-658.
Volpe, G. et al., Alternative BCR/ABL splice variants in Philadelphia chromosome-positive leukemias result in novel tumor-specific fusion proteins that may represent potential targets for immunotherapy approaches, Cancer Res., 67(11):5300-5307 (2007).
Wang Rong-Fu, Tumor antigens discovery: perspectives for cancer therapy, Mol Med, 3(11):716-731 (1997).
Warren et al., A census of predicted mutational epitopes suitable for immunologic cancer control, Human Immunology, New York, US, vol. 71, No. 3, Mar. 1, 2010.
Weinschenk, T. et al., Integrated Functional Genomics Approach for the Design of Patient-individual Antitumor Vaccines, Cancer Research, 62(20):5818-5827 (2002).
Wood, L. et al., The Genome Landscapes of Human Breast and Colorectal Cancers, Science, 318(5853):1108-1113 (2007).
Written Opinion of the International Search Authority, dated Apr. 5, 2012, Filed in relation to PCT Application 11 No. PCT/EP2011/002576, Filed May 24, 2011, Entitled Individualized Vaccines for Cancer, By Applicant 'BIONTECH AG, 6 pages.
Written Opinion of the International Search Authority, dated May 8, 2013, Filed in relation to PCT Application No. PCT/9 EP2012/002209, Filed May 23, 2012, Entitled Individualized Vaccines for Cancer, By Applicant'BIONTECH AG, 13 pages.
Ya et al., Mouse Model for Pre-Clinical Study of Human Cancer Immunotherapy, Curr Protoc Immunol, Feb. 2, 2016, 53 pages.
Yokoyama, Y, et al., Matrilysin (MMP-7) is a novel broadly expressed tumor antigen recognized by antigen-specific T cells, Clin Cancer Res, 14(17):5503-5511 (2008).
Zhang et al. 2011: The impact of next generation sequencing on genomics. J Genet Genomics 38 (3), 95-109.
Zhang et al. J. Biol. Chem., 279(10), 8635-41, 2004.
Zhang, Z., Gerstein, M., Nucleic Acids Res 31, 5338-5348 (2003).
Zhao et al. (2007). MHC-Peptide binding prediction for epitope based vaccine design, IJIB, 1(2):127-40.
Zhou et al., Hum. Gene Ther., 10(16):2719-24, 1999.
Zilfou JT et al.: Cold Spring Harb Perspect Biol 2009; 1 :a001883.

(56) References Cited

OTHER PUBLICATIONS

Zwaveling S et al., Cancer Res 2002;62:6187-93.
Doctoral Thesis by Marc Günder, 216 pages (2012). [Non-English copy].
No Author Listed, The problem with neoantigen prediction, Nat Biotechnol, 35(2):97 (2017).

\* cited by examiner

Figure 10:
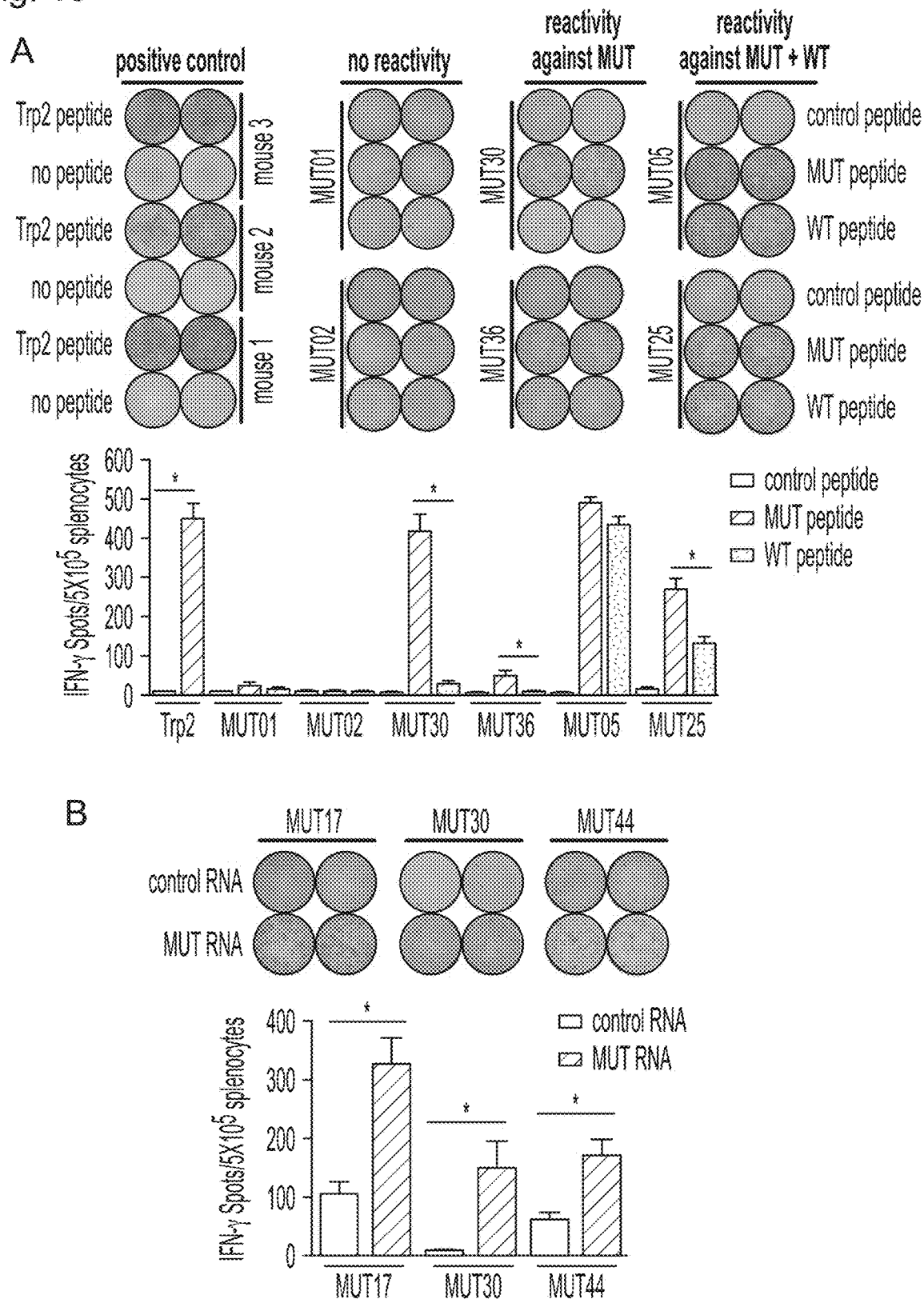

Fig. 10
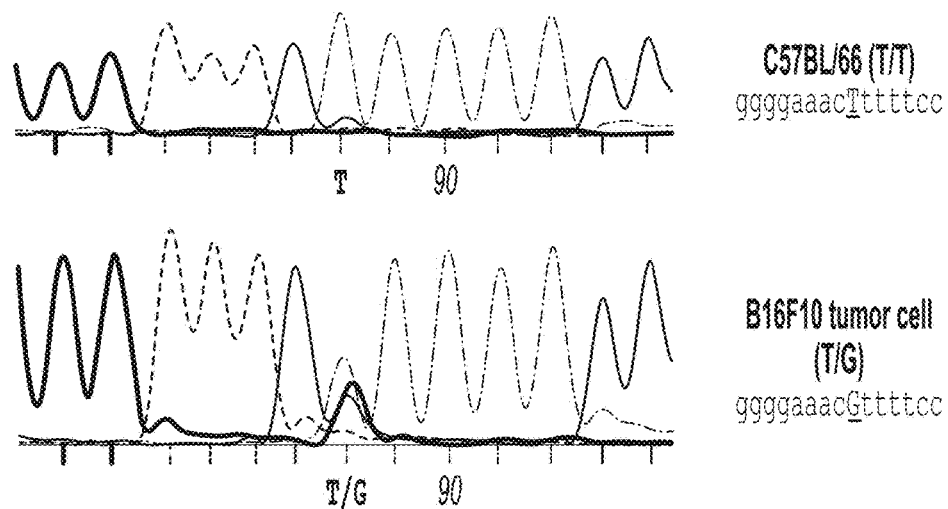
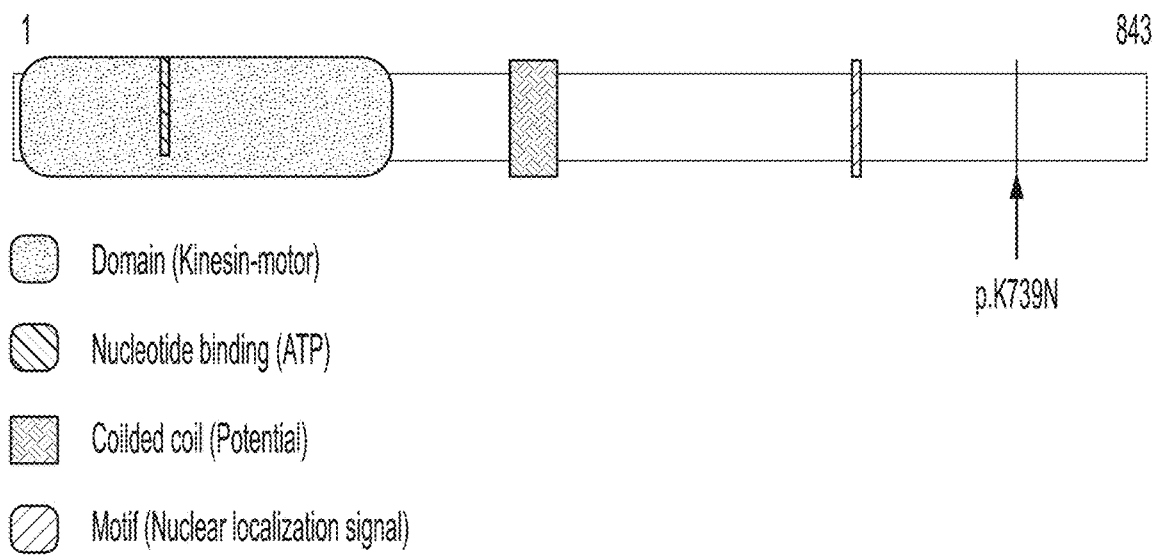

Fig. 14
A
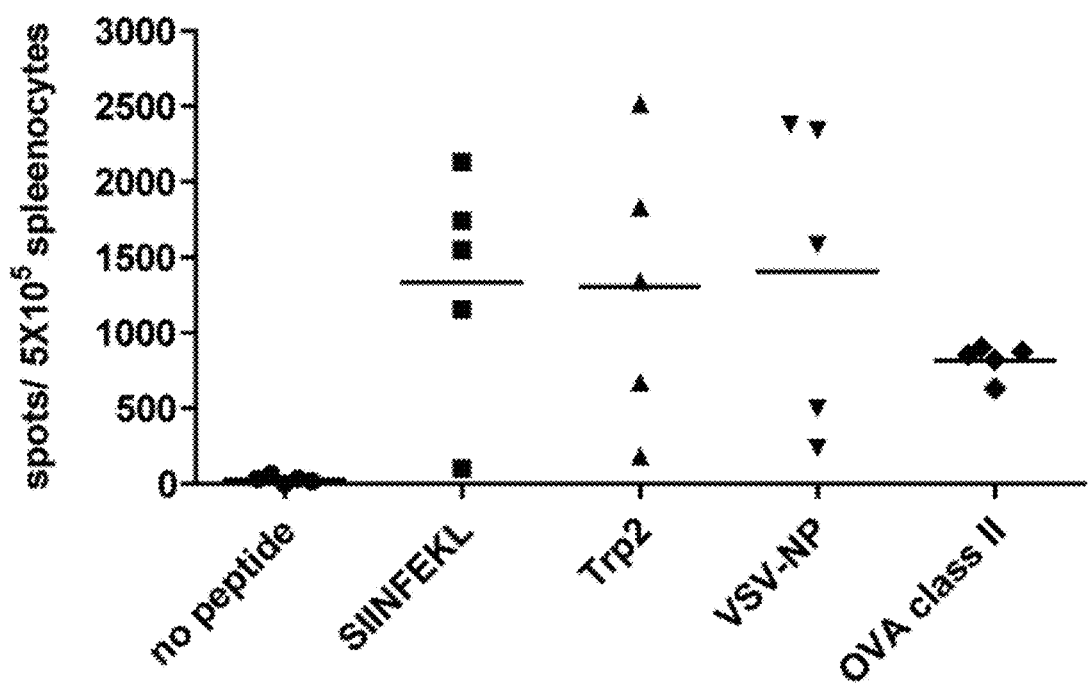
B
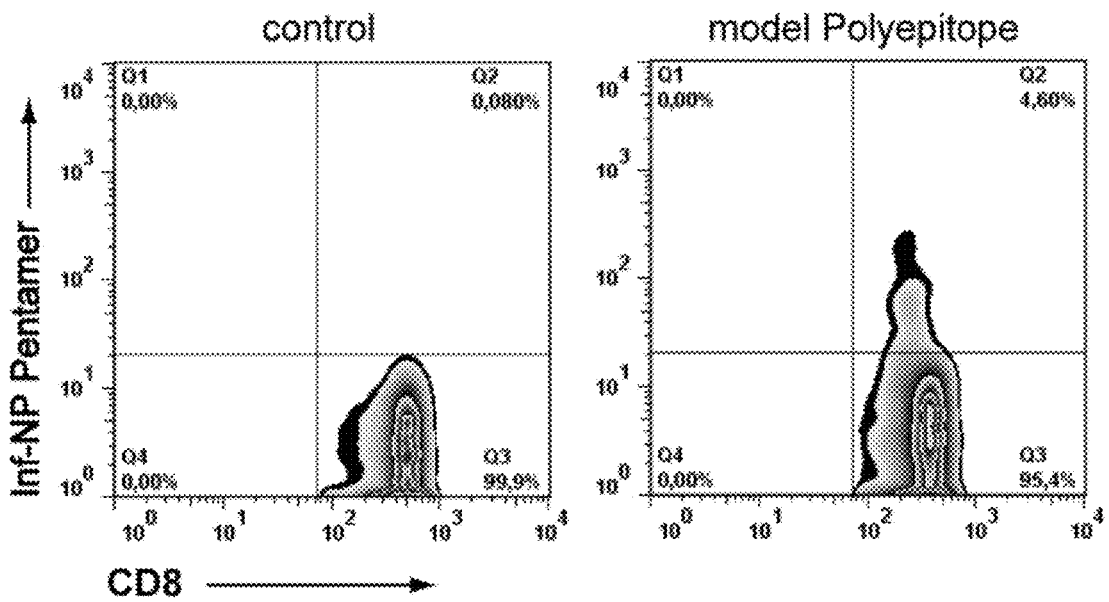

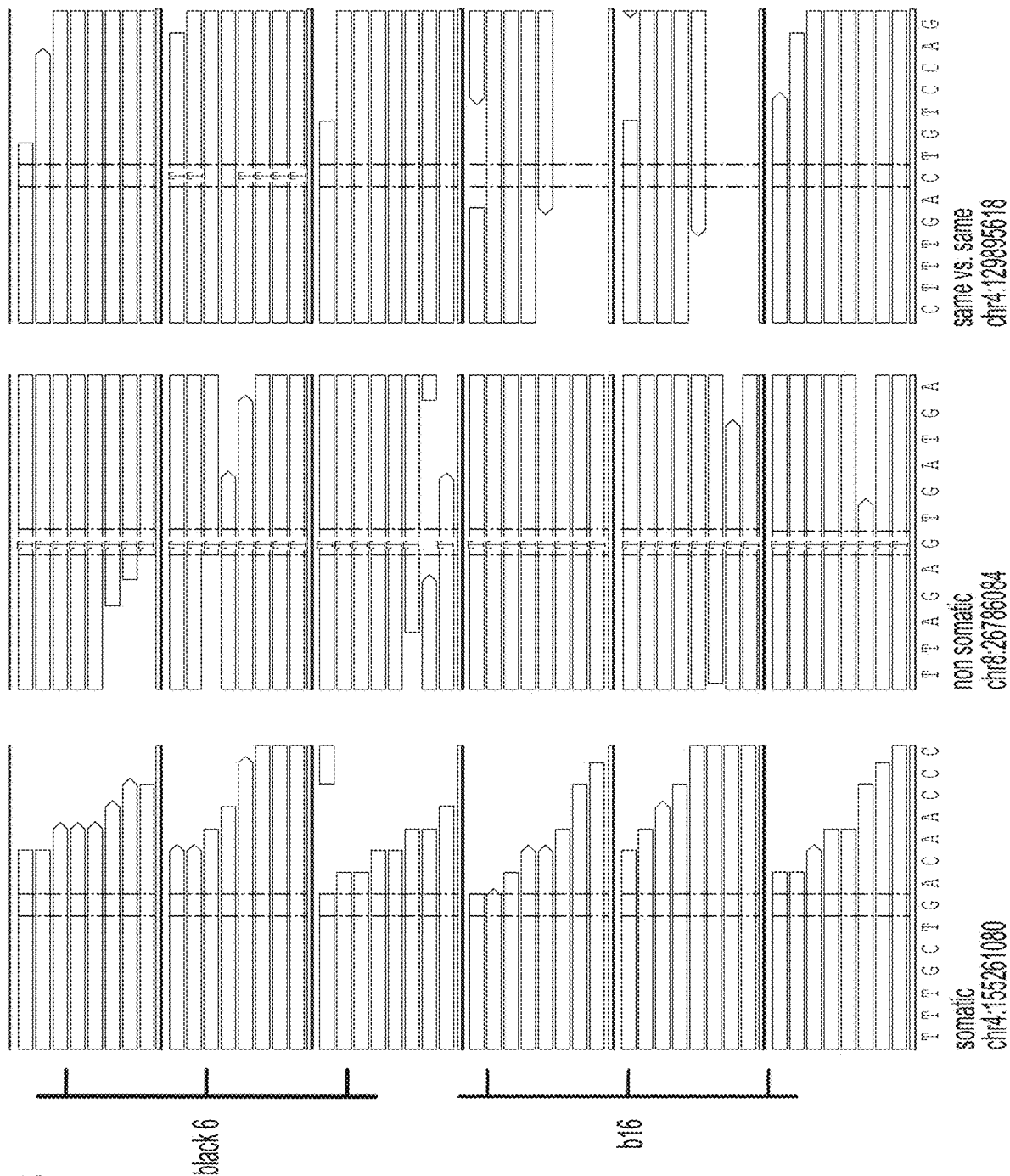

A

| Chromosome | Position | Reference allele | Sample allele(s) | relative rank [%] | FDR [%] |
|---|---|---|---|---|---|
| 8 | 110078987 | G | R | 3,2 | 0,6 |
| 1 | 59540714 | G | S | 7,6 | 0,7 |
| 5 | 124854313 | G | K | 7,8 | 0,7 |
| 10 | 59352802 | C | M | 8,3 | 0,7 |
| 16 | 36919828 | A | M | 9,8 | 0,7 |
| 2 | 144078227 | C | Y | 10,1 | 0,7 |
| 8 | 12834637 | G | S | 10,9 | 0,7 |
| 19 | 6121411 | T | Y | 11,4 | 0,7 |
| 1 | 585533360 | A | M | 12,1 | 0,7 |
| 15 | 98478052 | A | R | 13,6 | 0,7 |

B

INDIVIDUALIZED VACCINES FOR CANCER

CROSS-REFERENCE TO RELATED APPLICATIONS

This application is a continuation of U.S. application Ser. No. 14/119,348 filed Feb. 17, 2014, which is a national stage filing under U.S.C. § 371 of PCT International Application No. PCT/EP2012/002209 filed May 23, 2012, which claims foreign priority to PCT International Application No. PCT/EP2011/002576 filed May 24, 2011 and PCT International Application No. PCT/EP2012/000006 filed Jan. 2, 2012, the contents of each of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jul. 2, 2020, is named 2013237-0072_SL.txt and is 13,317 bytes in size.

TECHNICAL FIELD OF THE INVENTION

The present invention relates to the provision of vaccines which are specific for a patient's tumor and are potentially useful for immunotherapy of the primary tumor as well as tumor metastases.

BACKGROUND OF THE INVENTION

Cancer is a primary cause of mortality, accounting for 1 in 4 of all deaths. The treatment of cancer has traditionally been based on the law of averages—what works best for the largest number of patients. However, owing to the molecular heterogeneity in cancer, often less than 25% of treated individuals profit from the approved therapies. Individualized medicine based on tailored treatment of patients is regarded as a potential solution to low efficacies and high costs for innovation in drug development.

Antigen specific immunotherapy aims to enhance or induce specific immune responses in patients and has been successfully used to control cancer diseases. T cells play a central role in cell-mediated immunity in humans and animals. The recognition and binding of a particular antigen is mediated by the T cell receptors (TCRs) expressed on the surface of T cells. The T cell receptor (TCR) of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell.

The identification of a growing number of pathogen- and tumor-associated antigens (TAA) led to a broad collection of suitable targets for immunotherapy. Cells presenting immunogenic peptides (epitopes) derived from these antigens can be specifically targeted by either active or passive immunization strategies. Active immunization may tend to induce and expand antigen specific T cells in the patient, which are able to specifically recognize and kill diseased cells.

Different antigen formats can be used for tumor vaccination including whole cancer cells, proteins, peptides or immunizing vectors such as RNA, DNA or viral vectors that can be applied either directly in vivo or in vitro by pulsing of DCs following transfer into the patient. Cancers may arise from the accumulation of genomic mutations and epigenetic changes, of which a fraction may have a causative role. In addition to tumor associated antigens, human cancers carry on average 100-120 non-synonymous mutations, of which many are targetable by vaccines. More than 95% of mutations in a tumor are unique and patient specific (Weide et al. 2008: *J. Immunother.* 31, 180-188). The number of protein changing somatic mutations, which may result in tumor specific T cell epitopes, is in the range of 30 to 400. It has been predicted in silico that there are 40 to 60 HLA class I restricted epitopes per patient derived from tumor specific somatic mutations (Azuma et al. 1993: *Nature* 366, 76-79). Moreover, de novo immunogenic HLA class II restricted epitopes likely also result from tumor-associated mutations, however their number is still unknown.

Notably, some non-synonymous mutations are causally involved in neoplastic transformation, crucial for maintaining the oncogenic phenotype (driver mutations) and may represent a potential "Achilles' heel" of cancer cells. As such non-synonymous mutations are not subject to central immune tolerance, they can be ideal candidates for individual cancer vaccine development. Mutations found in the primary tumor may also be present in metastases. However, several studies demonstrated that metastatic tumors of a patient acquire additional genetic mutations during individual tumor evolution which are often clinically relevant (Suzuki et al. 2007: *Mol. Oncol.* 1 (2), 172-180; Campbell et al. 2010: *Nature* 467 (7319). 1109-1113). Furthermore, also the molecular characteristics of many metastases deviate significantly from those of primary tumors.

The technical problem underlying the present invention is to provide a highly effective individualized cancer vaccine.

The present invention is based on the identification of patient specific cancer mutations and targeting a patient's individual cancer mutation "signature". Specifically, the present invention which involves a genome, preferably exome, or transcriptome sequencing based individualized immunotherapy approach aims at immunotherapeutically targeting multiple individual mutations in cancer. Sequencing using Next Generation Sequencing (NGS) allows a fast and cost effective identification of patient specific cancer mutations.

The identification of non-synonymous point mutations resulting in amino acid changes that will be presented the patient's major histocompatibility complex (MHC) molecules provides novel epitopes (neo-epitopes) which are specific for the patient's cancer but are not found in normal cells of the patient. Collecting a set of mutations from cancer cells such as circulating tumor cells (CTC) allows the provision of a vaccine which induces an immune response potentially targeting the primary tumor even if containing genetically distinct subpopulations as well as tumor metastases. For vaccination, such neo-epitopes identified according to the present application are provided in a patient in the form of a polypeptide comprising said neo-epitopes and following appropriate processing and presentation by MHC molecules the neo-epitopes are displayed to the patient's immune system for stimulation of appropriate T cells.

Preferably, such polypeptide is provided in the patient by administering RNA encoding the polypeptide. A strategy wherein in vitro transcribed RNA (IVT-RNA) is directly injected into a patient by different immunization routes has been successfully tested in various animal models. RNA may be translated in transfected cells and the expressed protein following processing presented on the MHC molecules on the surface of the cells to elicit an immune response.

The advantages of using RNA as a kind of reversible gene therapy include transient expression and a non-transforming character. RNA does not need to enter the nucleus in order to be expressed and moreover cannot integrate into the host genome, thereby eliminating the risk of oncogenesis. Transfection rates attainable with RNA are relatively high. Furthermore, the amounts of protein achieved correspond to those in physiological expression.

The rationale for the immunotherapeutic targeting of multiple individual mutations is that (i) these mutations are exclusively expressed, (ii) mutated epitopes can be expected to be ideal for T cell immunotherapy since T cells recognizing them have not undergone thymic selection, (iii) tumor immune escape can be reduced e.g. by targeting "driver mutations" that are highly relevant for the tumor phenotype, and (iv) a multiepitopic immune response has a higher likelihood to result in improved clinical benefit.

DESCRIPTION OF INVENTION

Summary of the Invention

The present invention relates to efficient methods for providing individualized recombinant cancer vaccines inducing an efficient and specific immune response in a cancer patient and potentially targeting the primary tumor as well as tumor metastases. The cancer vaccines provided according to the invention when administered to a patent provide a collection of MHC presented epitopes specific for the patient's tumor suitable for stimulating, priming and/or expanding T cells directed against cells expressing antigens from which the MHC presented epitopes are derived. Thus, the vaccines described herein are preferably capable of inducing or promoting a cellular response, preferably cytotoxic T cell activity, against a cancer disease characterized by presentation of one or more cancer expressed antigens with class I MHC. Since a vaccine provided according to the present invention will target cancer specific mutations it will be specific for the patient's tumor.

In one aspect, the present invention relates to a method for providing an individualized cancer vaccine comprising the steps:
(a) identifying cancer specific somatic mutations in a tumor specimen of a cancer patient to provide a cancer mutation signature of the patient; and
(b) providing a vaccine featuring the cancer mutation signature obtained in step (a).

In one embodiment, the method of the invention comprises the following steps:
  i) providing a tumor specimen from a cancer patient and a non-tumorigenous specimen which preferably is derived from the cancer patient;
  ii) identifying sequence differences between the genome, exome and/or transcriptome of the tumor specimen and the genome, exome and/or transcriptome of the non-tumorigenous specimen;
  iii) designing a polypeptide comprising epitopes incorporating the sequence differences determined in step (ii);
  iv) providing the polypeptide designed in step (iii) or a nucleic acid, preferably RNA, encoding said polypeptide; and
  v) providing a vaccine comprising the polypeptide or nucleic acid provided in step (iv).

According to the invention a tumor specimen relates to any sample such as a bodily sample derived from a patient containing or being expected of containing tumor or cancer cells. The bodily sample may be any tissue sample such as blood, a tissue sample obtained from the primary tumor or from tumor metastases or any other sample containing tumor or cancer cells. Preferably, a bodily sample is blood and cancer specific somatic mutations or sequence differences are determined in one or more circulating tumor cells (CTCs) contained in the blood. In another embodiment, a tumor specimen relates to one or more isolated tumor or cancer cells such as circulating tumor cells (CTCs) or a sample containing one or more isolated tumor or cancer cells such as circulating tumor cells (CTCs).

A non-tumorigenous specimen relates to any sample such as a bodily sample derived from a patient or another individual which preferably is of the same species as the patient, preferably a healthy individual not containing or not being expected of containing tumor or cancer cells. The bodily sample may be any tissue sample such as blood or a sample from a non-tumorigenous tissue.

According to the invention, the term "cancer mutation signature" may refer to all cancer mutations present in one or more cancer cells of a patient or it may refer to only a portion of the cancer mutations present in one or more cancer cells of a patient. Accordingly, the present invention may involve the identification of all cancer specific mutations present in one or more cancer cells of a patient or it may involve the identification of only a portion of the cancer specific mutations present in one or more cancer cells of a patient. Generally, the method of the invention provides for the identification of a number of mutations which provides a sufficient number of neo-epitopes to be included into a vaccine. A "cancer mutation" relates to a sequence difference between the nucleic acid contained in a cancer cell and the nucleic acid contained in a normal cell.

Preferably, the mutations identified in the methods according to the present invention are non-synonymous mutations, preferably non-synonymous mutations of proteins expressed in a tumor or cancer cell.

In one embodiment, cancer specific somatic mutations or sequence differences are determined in the genome, preferably the entire genome, of a tumor specimen. Thus, the method of the invention may comprise identifying the cancer mutation signature of the genome, preferably the entire genome of one or more cancer cells. In one embodiment, the step of identifying cancer specific somatic mutations in a tumor specimen of a cancer patient comprises identifying the genome-wide cancer mutation profile.

In one embodiment, cancer specific somatic mutations or sequence differences are determined in the exome, preferably the entire exome, of a tumor specimen. The exome is part of the genome of an organism formed by exons, which are coding portions of expressed genes. The exome provides the genetic blueprint used in the synthesis of proteins and other functional gene products. It is the most functionally relevant part of the genome and, therefore, it is most likely to contribute to the phenotype of an organism. The exome of the human genome is estimated to comprise 1.5% of the total genome (Ng, P C et al., *PLoS Gen.,* 4(8): 1-15, 2008). Thus, the method of the invention may comprise identifying the cancer mutation signature of the exome, preferably the entire exome of one or more cancer cells. In one embodiment, the step of identifying cancer specific somatic mutations in a tumor specimen of a cancer patient comprises identifying the exome-wide cancer mutation profile.

In one embodiment, cancer specific somatic mutations or sequence differences are determined in the transcriptome, preferably the entire transcriptome, of a tumor specimen. The transcriptome is the set of all RNA molecules, including mRNA, rRNA, tRNA, and other non-coding RNA produced in one cell or a population of cells. In context of the present invention the transcriptome means the set of all RNA molecules produced in one cell, a population of cells, preferably a population of cancer cells, or all cells of a given individual at a certain time point. Thus, the method of the invention may comprise identifying the cancer mutation signature of the transcriptome, preferably the entire transcriptome of one or more cancer cells. In one embodiment, the step of identifying cancer specific somatic mutations in a tumor specimen of a cancer patient comprises identifying the transcriptome-wide cancer mutation profile.

In one embodiment, the step of identifying cancer specific somatic mutations or identifying sequence differences comprises single cell sequencing of one or more, preferably 2, 3, 4, 5, 6, 7, 8, 9, 10, 11, 12, 13, 14, 15, 16, 17, 18, 19, 20 or even more cancer cells. Thus, the method of the invention may comprise identifying a cancer mutation signature of said one or more cancer cells. In one embodiment, the cancer cells are circulating tumor cells. The cancer cells such as the circulating tumor cells may be isolated prior to single cell sequencing.

In one embodiment, the step of identifying cancer specific somatic mutations or identifying sequence differences involves using next generation sequencing (NGS).

In one embodiment, the step of identifying cancer specific somatic mutations or identifying sequence differences comprises sequencing genomic DNA and/or RNA of the tumor specimen.

To reveal cancer specific somatic mutations or sequence differences the sequence information obtained from the tumor specimen is preferably compared with a reference such as sequence information obtained from sequencing nucleic acid such as DNA or RNA of normal non-cancerous cells such as germline cells which may either be obtained from the patient or a different individual. In one embodiment, normal genomic germline DNA is obtained from peripheral blood mononuclear cells (PBMCs)

A vaccine provided according to the methods of the present invention relates to a vaccine which when administered to a patent preferably provides a collection of MHC presented epitopes, such as 2 or more, 5 or more, 10 or more, 15 or more, 20 or more, 25 or more, 30 or more and preferably up to 60, up to 55, up to 50, up to 45, up to 40, up to 35 or up to 30 MHC presented epitopes, incorporating sequence changes based on the identified mutations or sequence differences. Such MHC presented epitopes incorporating sequence changes based on the identified mutations or sequence differences are also termed "neo-epitopes" herein. Presentation of these epitopes by cells of a patient, in particular antigen presenting cells, preferably results in T cells targeting the epitopes when bound to MHC and thus, the patient's tumor, preferably the primary tumor as well as tumor metastases, expressing antigens from which the MHC presented epitopes are derived and presenting the same epitopes on the surface of the tumor cells.

For providing a vaccine, the method of the invention may comprise the arbitrary inclusion of a sufficient number of neo-epitopes (preferably in the form of an encoding nucleic acid) into a vaccine or it may comprise the further step of determining the usability of the identified mutations in epitopes for cancer vaccination. Thus further steps can involve one or more of the following: (i) assessing whether the sequence changes are located in known or predicted MHC presented epitopes, (ii) in vitro and/or in silico testing whether the sequence changes are located in MHC presented epitopes, e.g. testing whether the sequence changes are part of peptide sequences which are processed into and/or presented as MHC presented epitopes, and (iii) in vitro testing whether the envisaged mutated epitopes, in particular when present in their natural sequence context, e.g. when flanked by amino acid sequences also flanking said epitopes in the naturally occurring protein, and when expressed in antigen presenting cells are able to stimulate T cells of the patient having the desired specificity. Such flanking sequences each may comprise 3 or more, 5 or more, 10 or more, 15 or more, 20 or more and preferably up to 50, up to 45, up to 40, up to 35 or up to 30 amino acids and may flank the epitope sequence N-terminally and/or C-terminally.

Mutations or sequence differences determined according to the invention may be ranked for their usability as epitopes for cancer vaccination. Thus, in one aspect, the method of the invention comprises a manual or computer-based analytical process in which the identified mutations are analyzed and selected for their usability in the respective vaccine to be provided. In a preferred embodiment, said analytical process is a computational algorithm-based process. Preferably, said analytical process comprises one or more, preferably all of the following steps:

identifying expressed, protein modifying mutations, e.g. by analyzing transcripts;

identifying mutations which are potentially immunogenic, i.e. by comparing the data obtained with available datasets of confirmed immunogenic epitopes, e.g. those contained in public immune epitope databases such as i.e. the IMMUNE EPITOPE DATABASE AND ANALYSIS RESOURCE at http://www.immunoepitope.org The step of identifying mutations which are potentially immunogenic may comprise determining and/or ranking epitopes according to a prediction of their MHC-binding capacity, preferably MHC class-I binding capacity.

In another embodiment of the invention, the epitopes can be selected and/or ranked by using further parameters such as protein impact, associated gene expression, sequence uniqueness, predicted presentation likelihood, and association with oncogenes.

Multiple CTC analyses also allow selection and prioritization of mutations. For example, a mutation which is found in a larger portion of CTC may be prioritized higher than a mutation found in a lower portion of CTC.

The collection of mutation based neo-epitopes identified according to the invention and provided by a vaccine of the invention is preferably present in the form of a polypeptide comprising said neo-epitopes (polyepitopic polypeptide) or a nucleic acid, in particular RNA, encoding said polypeptide. Furthermore, the neo-epitopes may be present in the polypeptide in the form of a vaccine sequence, i.e. present in their natural sequence context, e.g. flanked by amino acid sequences also flanking said epitopes in the naturally occurring protein. Such flanking sequences each may comprise 5 or more, 10 or more, 15 or more, 20 or more and preferably up to 50, up to 45, up to 40, up to 35 or up to 30 amino acids and may flank the epitope sequence N-terminally and/or C-terminally. Thus, a vaccine sequence may comprise 20 or more, 25 or more, 30 or more, 35 or more, 40 or more and preferably up to 50, up to 45, up to 40, up to 35 or up to 30 amino acids. In one embodiment, the neo-epitopes and/or vaccine sequences are lined up in the polypeptide head-to-tail.

In one embodiment, the neo-epitopes and/or vaccine sequences are spaced by linkers, in particular neutral linkers. The term "linker" according to the invention relates to a peptide added between two peptide domains such as epitopes or vaccine sequences to connect said peptide domains. There is no particular limitation regarding the linker sequence. However, it is preferred that the linker sequence reduces steric hindrance between the two peptide domains, is well translated, and supports or allows processing of the epitopes. Furthermore, the linker should have no or only little immunogenic sequence elements. Linkers preferably should not create non-endogenous neo-epitopes like those generated from the junction suture between adjacent neo-epitopes, which might generate unwanted immune reactions. Therefore, the polyepitopic vaccine should preferably contain linker sequences which are able to reduce the number of unwanted MHC binding junction epitopes. Hoyt et al. (*EMBO J.* 25(8), 1720-9, 2006) and Zhang et al. (*J. Biol. Chem.* 279(10), 8635-41, 2004) have shown that glycine-rich sequences impair proteasomal processing and thus the use of glycine rich linker sequences act to minimize the number of linker-contained peptides that can be processed by the proteasome. Furthermore, glycine was observed to inhibit a strong binding in MHC binding groove positions (Abastado et al., *J. Immunol.* 15(7). 3569-75. 1993). Schlessinger et al. (*Proteins*, 61(1). 115-26, 2005) had found that amino acids glycine and serine included in an amino acid sequence result in a more flexible protein that is more efficiently translated and processed by the proteasome, enabling better access to the encoded neo-epitopes. The linker each may comprise 3 or more, 6 or more, 9 or more, 10 or more, 15 or more, 20 or more and preferably up to 50, up to 45, up to 40, up to 35 or up to 30 amino acids. Preferably the linker is enriched in glycine and/or serine amino acids. Preferably, at least 50%, at least 60%, at least 70%, at least 80%, at least 90%, or at least 95% of the amino acids of the linker are glycine and/or serine. In one preferred embodiment, a linker is substantially composed of the amino acids glycine and serine. In one embodiment, the linker comprises the amino acid sequence $(GGS)_a(GSS)_b(GGG)_c(SSG)_d(GSG)_e$ wherein a, b, c, d and e is independently a number selected from 0, 1, 2, 3, 4, 5, 6, 7, 8, 9, 10, 11, 12, 13, 14, 15, 16, 17, 18, 19, or 20 and wherein a +b+c+d+e are different from 0 and preferably are 2 or more, 3 or more, 4 or more or 5 or more. In one embodiment, the linker comprises a sequence as described herein including the linker sequences described in the examples such as the sequence GGSGGGGSG.

In another embodiment of the present invention the collection of mutation based neo-epitopes identified according to the invention and provided by a vaccine of the invention is preferably present in the form of a collection of polypeptides comprising said neo-epitopes on different polypeptides, wherein said polypeptides each comprise one or more neo-epitopes, which can also be overlapping, or a collection of nucleic acids, in particular RNAs, encoding said polypeptides.

In one particularly preferred embodiment, a polyepitopic polypeptide according to the present invention is administered to a patient in the form of a nucleic acid, preferably RNA such as in vitro transcribed or synthetic RNA, which may be expressed in cells of a patient such as antigen presenting cells to produce the polypeptide. The present invention also envisions the administration of one or more multiepitopic polypeptides which for the purpose of the present invention are comprised by the term "polyepitopic polypeptide", preferably in the form of a nucleic acid, preferably RNA such as in vitro transcribed or synthetic RNA, which may be expressed in cells of a patient such as antigen presenting cells to produce the one or more polypeptides. In the case of an administration of more than one multiepitopic polypeptide the neo-epitopes provided by the different multiepitopic polypeptides may be different or partially overlapping. Once present in cells of a patient such as antigen presenting cells the polypeptide according to the invention is processed to produce the neo-epitopes identified according to the invention. Administration of a vaccine provided according to the invention may provide MHC class II-presented epitopes that are capable of eliciting a CD4+ helper T cell response against cells expressing antigens from which the MHC presented epitopes are derived. Alternatively or additionally, administration of a vaccine provided according to the invention may provide MHC class I-presented epitopes that are capable of eliciting a CD8+ T cell response against cells expressing antigens from which the MHC presented epitopes are derived. Furthermore, administration of a vaccine provided according to the invention may provide one or more neo-epitopes (including known neo-epitopes and neo-epitopes identified according to the invention) as well as one or more epitopes not containing cancer specific somatic mutations but being expressed by cancer cells and preferably inducing an immune response against cancer cells, preferably a cancer specific immune response. In one embodiment, administration of a vaccine provided according to the invention provides neo-epitopes that are MHC class II-presented epitopes and/or are capable of eliciting a CD4+ helper T cell response against cells expressing antigens from which the MHC presented epitopes are derived as well as epitopes not containing cancer-specific somatic mutations that are MHC class I-presented epitopes and/or are capable of eliciting a CD8+ T cell response against cells expressing antigens from which the MHC presented epitopes are derived. In one embodiment, the epitopes not containing cancer-specific somatic mutations are derived from a tumor antigen. In one embodiment, the neo-epitopes and epitopes not containing cancer-specific somatic mutations have a synergistic effect in the treatment of cancer. Preferably, a vaccine provided according to the invention is useful for polyepitopic stimulation of cytotoxic and/or helper T cell responses.

In a further aspect, the present invention provides a vaccine which is obtainable by the method according to the invention. Accordingly, the present invention relates to a vaccine comprising a recombinant polypeptide comprising mutation based neo-epitopes, said neo-epitopes resulting from cancer specific somatic mutations in a tumor specimen of a cancer patient, or a nucleic acid encoding said polypeptide. Such recombinant polypeptide may also include epitopes not including cancer specific somatic mutations as discussed above.

Preferred embodiments of such vaccine are as described above in the context of the method of the invention.

A vaccine provided according to the invention may comprise a pharmaceutically acceptable carrier and may optionally comprise one or more adjuvants, stabilizers etc. The vaccine may in the form of a therapeutic or prophylactic vaccine.

Another aspect relates to a method for inducing an immune response in a patient, comprising administering to the patient a vaccine provided according to the invention.

Another aspect relates to a method of treating a cancer patient comprising the steps:
(a) providing an individualized cancer vaccine by the method according to the invention; and
(b) administering said vaccine to the patient.

Another aspect relates to a method of treating a cancer patient comprising administering the vaccine according to the invention to the patient.

In further aspects, the invention provides the vaccines described herein for use in the methods of treatment described herein, in particular for use in treating or preventing cancer.

The treatments of cancer described herein can be combined with surgical resection and/or radiation and/or traditional chemotherapy.

Another aspect of the invention relates to a method for determining a false discovery rate based on next generation sequencing data, said method including:
- taking a first sample of genetic material from an animal or human;
- taking a second sample of genetic material from an animal or human;
- taking a first sample of genetic material from tumor cells;
- taking a second sample of genetic material from said tumor cells;
- determining a common coverage tumor comparison by counting all bases of the reference genome which is included in both the tumor and at least one of said first sample of genetic material from an animal or human and said second sample of genetic material from an animal or human;
- determining a common coverage same vs. same comparison by counting all bases of the reference genome which are covered by both said first sample of genetic material from an animal or human and said second sample of genetic material from an animal or human;
- dividing said common coverage tumor comparison by said common coverage same vs. same comparison to form a normalization;
- determining a false discovery rate by dividing 1) the number of single nucleotide variations with a quality score greater than Q in a comparison of said first sample of genetic material from an animal or human and said second sample of genetic material from an animal or human, by 2) the number of single nucleotide variations with a quality score greater than Q in a comparison of said first sample of genetic material from said tumor cells and said second sample of genetic material from said tumor cells and 3) multiplying the result by said normalization.

In one embodiment, said genetic material is a DNA.
In one embodiment, Q is determined by:
- establishing a set of quality properties $S=(s_1, \ldots, s_n)$ wherein S is preferable to $T=(t_1, \ldots, t_n)$, denoted by S>T, when $s_i > t_i$ for all $i=1, \ldots, n$;
- defining an intermediate false discovery rate by dividing 1) the number of single nucleotide variations with a quality score S>T in a comparison of said first DNA sample from an animal or human and said second DNA sample from an animal or human, by 2) the number of single nucleotide variations with a quality score S>T in a comparison of said first DNA sample from said tumor cells and said second DNA sample from said tumor cells and 3) multiplying the result by said normalization,
- determining the value range for each property for n mutations with n quality properties each;
- sampling up to p values out of said value range;
- creating each possible combination of sampled quality values which results in $p^n$ data points;
- using a random sample of said data points as a predictor for random forest training;
- using the corresponding intermediate false discovery rate value as a response for said random forest training,
- wherein the resulting regression score of said random forest training is Q.

In one embodiment, said second DNA sample from an animal or human is allogenic to said first DNA sample from an animal or human. In one embodiment, said second DNA sample from an animal or human is autologous to said first DNA sample from an animal or human. In one embodiment, said second DNA sample from an animal or human is xenogenic to said first DNA sample from an animal or human.

In one embodiment, said genetic material is a RNA.
In one embodiment, Q is determined by:
- establishing a set of quality properties $S=(s_1, \ldots, s_n)$ wherein S is preferable to $T=(t_1, \ldots, t_n)$, denoted by S>T, when $s_i > t_i$ for all $i=1, \ldots, n$;
- defining an intermediate false discovery rate by dividing 1) the number of single nucleotide variations with a quality score S>T in a comparison of said first RNA sample from an animal or human and said second RNA sample from an animal or human, by 2) the number of single nucleotide variations with a quality score S>T in a comparison of said first RNA sample from said tumor cells and said second RNA sample from said tumor cells and 3) multiplying the result by said normalization,
- determining the value range for each property for m mutations with n quality properties each;
- sampling up top values out of said value range;
- creating each possible combination of sampled quality values which results in $p^n$ data points;
- using a random sample of said data points as a predictor for random forest training;
- using the corresponding intermediate false discovery rate value as a response for said random forest training,
- wherein the resulting regression score of said random forest training is Q.

In one embodiment, said second RNA sample from an animal or human is allogenic to said first RNA sample from an animal or human. In one embodiment, said second RNA sample from an animal or human is autologous to said first RNA sample from an animal or human. In one embodiment, said second RNA sample from an animal or human is xenogenic to said first RNA sample from an animal or human.

In one embodiment, said false discovery rate is used to make a vaccine formulation. In one embodiment, said vaccine is deliverable intravenously. In one embodiment, said vaccine is deliverable dermally. In one embodiment, said vaccine is deliverable muscularly. In one embodiment, said vaccine is deliverable subcutaneously. In one embodiment, said vaccine is tailored for a specific patient.

In one embodiment, one of said first sample of genetic material from an animal or human and said second sample of genetic material from an animal or human is from said specific patient.

In one embodiment, said step of determining a common coverage tumor comparison by counting all bases of the reference genome which is included in both the tumor and at least one of said first sample of genetic material from an animal or human and said second sample of genetic material from an animal or human uses an automated system to count all bases.

In one embodiment, said step of determining a common coverage same vs. same comparison by counting all bases of the reference genome which are covered by both said first sample of genetic material from an animal or human and said second sample of genetic material from an animal or human uses said automated system.

In one embodiment, said step of dividing said common coverage tumor comparison by said common coverage same vs. same comparison to form a normalization uses said automated system.

In one embodiment, said step of determining a false discovery rate by dividing 1) the number of single nucleotide variations with a quality score greater than Q in a comparison of said first sample of genetic material from an animal or human and said second sample of genetic material from an animal or human, by 2) the number of single nucleotide variations with a quality score greater than Q in a comparison of said first sample of genetic material from said tumor cells and said second sample of genetic material from said tumor cells and 3) multiplying the result by said normalization uses said automated system.

Another aspect of the invention relates to a method for determining an estimated receiver operating curve (ROC), said method including:
receiving a dataset of mutations, each mutation associated with a false discovery rate (FDR); and
for each mutation:
determining a true positive rate (TPR) by subtracting said FDR from one; and
determining a false positive rate (FPR) by setting said FPR equal to said FDR; and
forming an estimated ROC by plotting, for each mutation, a point at the cumulative TPR and FPR values up to said mutation, divided by the sum of all TPR and FPR values.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment RNA comprises a poly(A)-tail consisting of 120 nucleotides and in another preferred embodiment the RNA molecule comprises a 5'-cap analog, then in a preferred embodiment, the RNA comprises the poly(A)-tail consisting of 120 nucleotides and the 5'-cap analog.

Preferably, the terms used herein are defined as described in "A multilingual glossary of biotechnological terms: (IUPAC Recommendations)", H. G. W. Leuenberger, B. Nagel, and H. Kölbl, Eds., (1995) *Helvetica Chimica Acta*, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The vaccine provided according to the invention is a recombinant vaccine.

The term "recombinant" in the context of the present invention means "made through genetic engineering". Preferably, a "recombinant entity" such as a recombinant polypeptide in the context of the present invention is not occurring naturally, and preferably is a result of a combination of entities such as amino acid or nucleic acid sequences which are not combined in nature. For example, a recombinant polypeptide in the context of the present invention may contain several amino acid sequences such as neo-epitopes or vaccine sequences derived from different proteins or different portions of the same protein fused together, e.g., by peptide bonds or appropriate linkers.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

According to the invention, the term "vaccine" relates to a pharmaceutical preparation (pharmaceutical composition) or product that upon administration induces an immune response, in particular a cellular immune response, which recognizes and attacks a pathogen or a diseased cell such as a cancer cell. A vaccine may be used for the prevention or treatment of a disease. The term "individualized cancer vaccine" concerns a particular cancer patient and means that a cancer vaccine is adapted to the needs or special circumstances of an individual cancer patient.

The term "immune response" refers to an integrated bodily response to an antigen and preferably refers to a cellular immune response or a cellular as well as a humoral immune response. The immune response may be protective/preventive/prophylactic and/or therapeutic.

"Inducing an immune response" may mean that there was no immune response against a particular antigen before induction, but it may also mean that there was a certain level of immune response against a particular antigen before induction and after induction said immune response is enhanced. Thus, "inducing an immune response" also includes "enhancing an immune response". Preferably, after inducing an immune response in a subject, said subject is protected from developing a disease such as a cancer disease or the disease condition is ameliorated by inducing an immune response. For example, an immune response against a tumor expressed antigen may be induced in a patient having a cancer disease or in a subject being at risk of developing a cancer disease. Inducing an immune response in this case may mean that the disease condition of the subject is ameliorated, that the subject does not develop metastases, or that the subject being at risk of developing a cancer disease does not develop a cancer disease.

A "cellular immune response", a "cellular response", a "cellular response against an antigen" or a similar term is meant to include a cellular response directed to cells characterized by presentation of an antigen with class I or class II MHC. The cellular response relates to cells called T cells or T-lymphocytes which act as either "helpers" or "killers". The helper T cells (also termed CD4$^+$ T cells) play a central role by regulating the immune response and the killer cells (also termed cytotoxic T cells, cytolytic T cells, CD8$^+$ T cells or CTLs) kill diseased cells such as cancer cells, preventing the production of more diseased cells. In preferred embodiments, the present invention involves the stimulation of an anti-tumor CTL response against tumor cells expressing one or more tumor expressed antigens and preferably presenting such tumor expressed antigens with class I MHC.

An "antigen" according to the invention covers any substance that will elicit an immune response. In particular, an "antigen" relates to any substance, preferably a peptide or protein, that reacts specifically with antibodies or T-lymphocytes (T cells). According to the present invention, the term "antigen" comprises any molecule which comprises at least one epitope. Preferably, an antigen in the context of the present invention is a molecule which, optionally after processing, induces an immune reaction, which is preferably specific for the antigen (including cells expressing the antigen). According to the present invention, any suitable antigen may be used, which is a candidate for an immune reaction, wherein the immune reaction is preferably a cellular immune reaction. In the context of the embodiments of the present invention, the antigen is preferably presented by a cell, preferably by an antigen presenting cell which includes a diseased cell, in particular a cancer cell, in the context of MHC molecules, which results in an immune reaction against the antigen. An antigen is preferably a product which corresponds to or is derived from a naturally occurring antigen. Such naturally occurring antigens include tumor antigens.

In a preferred embodiment, the antigen is a tumor antigen, i.e., a part of a tumor cell such as a protein or peptide expressed in a tumor cell which may be derived from the cytoplasm, the cell surface or the cell nucleus, in particular those which primarily occur intracellularly or as surface antigens of tumor cells. For example, tumor antigens include the carcinoembryonal antigen, α1-fetoprotein, isoferritin, and fetal sulphoglycoprotein, α2-H-ferroprotein and γ-fetoprotein. According to the present invention, a tumor antigen preferably comprises any antigen which is expressed in and optionally characteristic with respect to type and/or expression level for tumors or cancers as well as for tumor or cancer cells. In one embodiment, the term "tumor antigen" or "tumor-associated antigen" relates to proteins that are under normal conditions specifically expressed in a limited number of tissues and/or organs or in specific developmental stages, for example, the tumor antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. Preferably, the tumor antigen or the aberrant expression of the tumor antigen identifies cancer cells. In the context of the present invention, the tumor antigen that is expressed by a cancer cell in a subject, e.g., a patient suffering from a cancer disease, is preferably a self-protein in said subject. In preferred embodiments, the tumor antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system.

According to the invention, the terms "tumor antigen", "tumor expressed antigen", "cancer antigen" and "cancer expressed antigen" are equivalents and are used interchangeably herein.

The term "immunogenicity" relates to the relative effectivity of an antigen to induce an immune reaction.

An "antigen peptide" according to the invention preferably relates to a portion or fragment of an antigen which is capable of stimulating an immune response, preferably a cellular response against the antigen or cells characterized by expression of the antigen and preferably by presentation of the antigen such as diseased cells, in particular cancer cells. Preferably, an antigen peptide is capable of stimulating a cellular response against a cell characterized by presentation of an antigen with class I MHC and preferably is capable of stimulating an antigen-responsive cytotoxic T-lymphocyte (CTL). Preferably, the antigen peptides according to the invention are MHC class I and/or class II presented peptides or can be processed to produce MHC class I and/or class II presented peptides. Preferably, the antigen peptides comprise an amino acid sequence substantially corresponding to the amino acid sequence of a fragment of an antigen. Preferably, said fragment of an antigen is an MHC class I and/or class II presented peptide. Preferably, an antigen peptide according to the invention comprises an amino acid sequence substantially corresponding to the amino acid sequence of such fragment and is processed to produce such fragment, i.e., an MHC class I and/or class II presented peptide derived from an antigen.

If a peptide is to be presented directly, i.e., without processing, in particular without cleavage, it has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length.

If a peptide is part of a larger entity comprising additional sequences, e.g. of a vaccine sequence or polypeptide, and is to be presented following processing, in particular following cleavage, the peptide produced by processing has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably, the sequence of the peptide which is to be presented following processing is derived from the amino acid sequence of an antigen, i.e., its sequence substantially corresponds and is preferably completely identical to a fragment of an antigen. Thus, an antigen peptide or vaccine sequence according to the invention in one embodiment comprises a sequence of 7-20 amino acids in length, more preferably 7-12 amino acids in length, more preferably 8-11 amino acids in length, in particular 9 or 10 amino acids in length which substantially corresponds and is preferably completely identical to a fragment of an antigen and following processing of the antigen peptide or vaccine sequence makes up the presented peptide. According to the invention, such peptide produced by processing comprises the identified sequence change.

According to the invention, an antigen peptide or epitope may be present in a vaccine as a part of a larger entity such as a vaccine sequence and/or a polypeptide comprising more than one antigen peptide or epitope. The presented antigen peptide or epitope is produced following suitable processing.

Peptides having amino acid sequences substantially corresponding to a sequence of a peptide which is presented by the class I MHC may differ at one or more residues that are not essential for TCR recognition of the peptide as presented by the class I MHC, or for peptide binding to MHC. Such substantially corresponding peptides are also capable of stimulating an antigen-responsive CTL and may be considered immunologically equivalent. Peptides having amino acid sequences differing from a presented peptide at residues that do not affect TCR recognition but improve the stability of binding to MHC may improve the immunogenicity of the antigen peptide, and may be referred to herein as "optimized peptide". Using existing knowledge about which of these residues may be more likely to affect binding either to the MHC or to the TCR, a rational approach to the design of substantially corresponding peptides may be employed. Resulting peptides that are functional are contemplated as antigen peptides.

An antigen peptide when presented by MHC should be recognizable by a T cell receptor. Preferably, the antigen peptide if recognized by a T cell receptor is able to induce in the presence of appropriate co-stimulatory signals, clonal expansion of the T cell carrying the T cell receptor specifically recognizing the antigen peptide. Preferably, antigen peptides, in particular if presented in the context of MHC molecules, are capable of stimulating an immune response, preferably a cellular response against the antigen from which they are derived or cells characterized by expression of the antigen and preferably characterized by presentation of the antigen. Preferably, an antigen peptide is capable of stimulating a cellular response against a cell characterized by presentation of the antigen with class I MHC and preferably is capable of stimulating an antigen-responsive CTL. Such cell preferably is a target cell.

"Antigen processing" or "processing" refers to the degradation of a polypeptide or antigen into procession products, which are fragments of said polypeptide or antigen (e.g., the degradation of a polypeptide into peptides) and the association of one or more of these fragments (e.g., via binding) with MHC molecules for presentation by cells, preferably antigen presenting cells, to specific T cells.

"Antigen presenting cells" (APC) are cells which present peptide fragments of protein antigens in association with MHC molecules on their cell surface. Some APCs may activate antigen specific T cells.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells.

The main types of professional antigen-presenting cells are dendritic cells, which have the broadest range of antigen presentation, and are probably the most important antigen-presenting cells, macrophages, B-cells, and certain activated epithelial cells.

Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity.

Dendritic cells are conveniently categorized as "immature" and "mature" cells, which can be used as a simple way to discriminate between two well characterized phenotypes. However, this nomenclature should not be construed to exclude all possible intermediate stages of differentiation.

Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e. g. CD54 and CD11) and costimulatory molecules (e. g., CD40, CD80, CD86 and 4-1 BB).

Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

Non-professional antigen-presenting cells do not constitutively express the MHC class II proteins required for interaction with naive T cells; these are expressed only upon stimulation of the non-professional antigen-presenting cells by certain cytokines such as IFNγ.

"Antigen presenting cells" can be loaded with MHC class I presented peptides by transducing the cells with nucleic acid, preferably RNA, encoding a peptide or polypeptide comprising the peptide to be presented, e.g. a nucleic acid encoding the antigen.

In some embodiments, a pharmaceutical composition of the invention comprising a gene delivery vehicle that targets a dendritic or other antigen presenting cell may be administered to a patient, resulting in transfection that occurs in vivo. In vivo transfection of dendritic cells, for example, may generally be performed using any methods known in the art, such as those described in WO 97/24447, or the gene gun approach described by Mahvi et al., Immunology and cell Biology 75: 456-460, 1997.

According to the invention, the term "antigen presenting cell" also includes target cells.

"Target cell" shall mean a cell which is a target for an immune response such as a cellular immune response. Target cells include cells that present an antigen or an antigen epitope, i.e. a peptide fragment derived from an antigen, and include any undesirable cell such as a cancer cell. In preferred embodiments, the target cell is a cell expressing an antigen as described herein and preferably presenting said antigen with class I MHC.

The term "epitope" refers to an antigenic determinant in a molecule such as an antigen, i.e., to a part in or fragment of the molecule that is recognized by the immune system, for example, that is recognized by a T cell, in particular when presented in the context of MHC molecules. An epitope of a protein such as a tumor antigen preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. It is particularly preferred that the epitope in the context of the present invention is a T cell epitope.

According to the invention an epitope may bind to MHC molecules such as MHC molecules on the surface of a cell and thus, may be a "MHC binding peptide" or "antigen peptide". The term "MHC binding peptide" relates to a peptide which binds to an MHC class I and/or an MHC class II molecule. In the case of class I MHC/peptide complexes, the binding peptides are typically 8-10 amino acids long although longer or shorter peptides may be effective. In the case of class II MHC/peptide complexes, the binding peptides are typically 10-25 amino acids long and are in particular 13-18 amino acids long, whereas longer and shorter peptides may be effective.

The terms "epitope", "antigen peptide", "antigen epitope", "immunogenic peptide" and "MHC binding peptide" are used interchangeably herein and preferably relate to an incomplete representation of an antigen which is preferably capable of eliciting an immune response against the antigen or a cell expressing or comprising and preferably presenting the antigen.

Preferably, the terms relate to an immunogenic portion of an antigen. Preferably, it is a portion of an antigen that is recognized (i.e., specifically bound) by a T cell receptor, in particular if presented in the context of MHC molecules. Preferred such immunogenic portions bind to an MHC class I or class II molecule. As used herein, an immunogenic portion is said to "bind to" an MHC class I or class II molecule if such binding is detectable using any assay known in the art.

As used herein the term "neo-epitope" refers to an epitope that is not present in a reference such as a normal non-cancerous or germline cell but is found in cancer cells. This includes, in particular, situations wherein in a normal non-cancerous or germline cell a corresponding epitope is found, however, due to one or more mutations in a cancer cell the sequence of the epitope is changed so as to result in the neo-epitope.

The term "portion" refers to a fraction. With respect to a particular structure such as an amino acid sequence or protein the term "portion" thereof may designate a continuous or a discontinuous fraction of said structure. Preferably, a portion of an amino acid sequence comprises at least 1%, at least 5%, at least 10%, at least 20%, at least 30%, preferably at least 40%, preferably at least 50%, more preferably at least 60%, more preferably at least 70%, even more preferably at least 80%, and most preferably at least 90% of the amino acids of said amino acid sequence. Preferably, if the portion is a discontinuous fraction said discontinuous fraction is composed of 2, 3, 4, 5, 6, 7, 8, or more parts of a structure, each part being a continuous element of the structure. For example, a discontinuous fraction of an amino acid sequence may be composed of 2, 3, 4, 5, 6, 7, 8, or more, preferably not more than 4 parts of said amino acid sequence, wherein each part preferably comprises at least 5 continuous amino acids, at least 10 continuous amino acids, preferably at least 20 continuous amino acids, preferably at least 30 continuous amino acids of the amino acid sequence.

The terms "part" and "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope, peptide or protein is preferably immunologically equivalent to the epitope, peptide or protein it is derived from. In the context of the present invention, a "part" of a structure such as an amino acid sequence preferably comprises, preferably consists of at least 10%, at least 20%, at least 30%, at least 40%, at least 50%, at least 60%, at least 70%, at least 80%, at least 85%, at least 90%, at least 92%, at least 94%, at least 96%, at least 98%, at least 99% of the entire structure or amino acid sequence.

The term "immunoreactive cell" in the context of the present invention relates to a cell which exerts effector functions during an immune reaction. An "immunoreactive cell" preferably is capable of binding an antigen or a cell characterized by presentation of an antigen or an antigen peptide derived from an antigen and mediating an immune response. For example, such cells secrete cytokines and/or chemokines, secrete antibodies, recognize cancerous cells, and optionally eliminate such cells. For example, immunoreactive cells comprise T cells (cytotoxic T cells, helper T cells, tumor infiltrating T cells), B cells, natural killer cells, neutrophils, macrophages, and dendritic cells. Preferably, in the context of the present invention, "immunoreactive cells" are T cells, preferably CD4$^+$ and/or CD8$^+$ T cells.

Preferably, an "immunoreactive cell" recognizes an antigen or an antigen peptide derived from an antigen with some degree of specificity, in particular if presented in the context of MHC molecules such as on the surface of antigen presenting cells or diseased cells such as cancer cells. Preferably, said recognition enables the cell that recognizes an antigen or an antigen peptide derived from said antigen to be responsive or reactive. If the cell is a helper T cell (CD4$^+$ T cell) bearing receptors that recognize an antigen or an antigen peptide derived from an antigen in the context of MHC class II molecules such responsiveness or reactivity may involve the release of cytokines and/or the activation of CD8$^+$ lymphocytes (CTLs) and/or B-cells. If the cell is a CTL such responsiveness or reactivity may involve the elimination of cells presented in the context of MHC class I molecules, i.e., cells characterized by presentation of an antigen with class I MHC, for example, via apoptosis or perforin-mediated cell lysis. According to the invention, CTL responsiveness may include sustained calcium flux, cell division, production of cytokines such as IFN-γ and TNF-α, upregulation of activation markers such as CD44 and CD69, and specific cytolytic killing of antigen expressing target cells. CTL responsiveness may also be determined using an artificial reporter that accurately indicates CTL responsiveness. Such CTL that recognizes an antigen or an antigen peptide derived from an antigen and are responsive or reactive are also termed "antigen-responsive CTL" herein. If the cell is a B cell such responsiveness may involve the release of immunoglobulins.

The terms "T cell" and "T lymphocyte" are used interchangeably herein and include T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

The first signal in activation of T cells is provided by binding of the T cell receptor to a short peptide presented by the major histocompatibility complex (MHC) on another cell. This ensures that only a T cell with a TCR specific to that peptide is activated. The partner cell is usually a professional antigen presenting cell (APC), usually a dendritic cell in the case of naïve responses, although B cells and macrophages can be important APCs. The peptides presented to CD8+ T cells by MHC class I molecules are typically 8-10 amino acids in length; the peptides presented to CD4+ T cells by MHC class II molecules are typically longer, as the ends of the binding cleft of the MHC class II molecule are open.

According to the present invention, a T cell receptor is capable of binding to a predetermined target if it has a significant affinity for said predetermined target and binds to said predetermined target in standard assays. "Affinity" or "binding affinity" is often measured by equilibrium dissociation constant ($K_D$). A T cell receptor is not (substantially) capable of binding to a target if it has no significant affinity for said target and does not bind significantly to said target in standard assays.

A T cell receptor is preferably capable of binding specifically to a predetermined target. A T cell receptor is specific for a predetermined target if it is capable of binding to said predetermined target while it is not (substantially) capable of binding to other targets, i.e. has no significant affinity for other targets and does not significantly bind to other targets in standard assays.

Cytotoxic T lymphocytes may be generated in vivo by incorporation of an antigen or an antigen peptide into antigen-presenting cells in vivo. The antigen or antigen peptide may be represented as protein, as DNA (e.g. within a vector) or as RNA. The antigen may be processed to produce a peptide partner for the MHC molecule, while a fragment thereof may be presented without the need for further processing. The latter is the case in particular, if these can bind to MHC molecules. In general, administration to a patient by intradermal injection is possible. However, injection may also be carried out intranodally into a lymph node (Maloy et al. (2001), Proc Natl Acad Sci USA 98:3299-303). The resulting cells present the complex of interest and are recognized by autologous cytotoxic T lymphocytes which then propagate.

Specific activation of CD4+ or CD8+ T cells may be detected in a variety of ways. Methods for detecting specific T cell activation include detecting the proliferation of T cells, the production of cytokines (e.g., lymphokines), or the generation of cytolytic activity. For CD4+ T cells, a preferred method for detecting specific T cell activation is the detection of the proliferation of T cells. For CD8+ T cells, a preferred method for detecting specific T cell activation is the detection of the generation of cytolytic activity.

The term "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self antigens (peptide fragments from the cell itself) and non-self antigens (e.g., fragments of invading microorganisms) to a T cell.

The MHC region is divided into three subgroups, class I, class II, and class III. MHC class I proteins contain an α-chain and β2-microglobulin (not part of the MHC encoded by chromosome 15). They present antigen fragments to cytotoxic T cells. On most immune system cells, specifically on antigen-presenting cells, MHC class II proteins contain α- and β-chains and they present antigen fragments to T-helper cells. MHC class III region encodes for other immune components, such as complement components and some that encode cytokines.

In humans, genes in the MHC region that encode antigen-presenting proteins on the cell surface are referred to as human leukocyte antigen (HLA) genes. However the abbreviation MHC is often used to refer to HLA gene products. HLA genes include the nine so-called classical MHC genes: HLA-A, HLA-B, HLA-C, HLA-DPA1, HLA-DPB1, HLA-DQA1, HLA-DQB1, HLA-DRA, and HLA-DRB1.

In one preferred embodiment of all aspects of the invention an MHC molecule is an HLA molecule.

By "cell characterized by presentation of an antigen" or "cell presenting an antigen" or similar expressions is meant a cell such as a diseased cell, e.g. a cancer cell, or an antigen presenting cell presenting the antigen it expresses or a fragment derived from said antigen, e.g. by processing of the antigen, in the context of MHC molecules, in particular MHC Class I molecules. Similarly, the terms "disease characterized by presentation of an antigen" denotes a disease involving cells characterized by presentation of an antigen, in particular with class I MHC. Presentation of an antigen by a cell may be effected by transfecting the cell with a nucleic acid such as RNA encoding the antigen.

By "fragment of an antigen which is presented" or similar expressions is meant that the fragment can be presented by MHC class I or class II, preferably MHC class I, e.g. when added directly to antigen presenting cells. In one embodiment, the fragment is a fragment which is naturally presented by cells expressing an antigen.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral and/or cellular immune response, the strength and/or duration of the induced immune reaction, or the specificity of the induced immune reaction. In the context of the present invention, the term "immunologically equivalent" is preferably used with respect to the immunological effects or properties of a peptide used for immunization. For example, an amino acid sequence is immunologically equivalent to a reference amino acid sequence if said amino acid sequence when exposed to the immune system of a subject induces an immune reaction having a specificity of reacting with the reference amino acid sequence.

The term "immune effector functions" in the context of the present invention includes any functions mediated by components of the immune system that result, for example, in the killing of tumor cells, or in the inhibition of tumor growth and/or inhibition of tumor development, including inhibition of tumor dissemination and metastasis. Preferably, the immune effector functions in the context of the present invention are T cell mediated effector functions. Such functions comprise in the case of a helper T cell (CD4$^+$ T cell) the recognition of an antigen or an antigen peptide derived from an antigen in the context of MHC class II molecules by T cell receptors, the release of cytokines and/or the activation of CD8$^+$ lymphocytes (CTLs) and/or B-cells, and in the case of CTL the recognition of an antigen or an antigen peptide derived from an antigen in the context of MHC class I molecules by T cell receptors, the elimination of cells presented in the context of MHC class I molecules, i.e., cells characterized by presentation of an antigen with class I MHC, for example, via apoptosis or perforin-mediated cell lysis, production of cytokines such as IFN-γ and TNF-α, and specific cytolytic killing of antigen expressing target cells.

The term "genome" relates to the total amount of genetic information in the chromosomes of an organism or a cell. The term "exome" refers to the coding regions of a genome. The term "transcriptome" relates to the set of all RNA molecules.

A "nucleic acid" is according to the invention preferably deoxyribonucleic acid (DNA) or ribonucleic acid (RNA), more preferably RNA, most preferably in vitro transcribed RNA (IVT RNA) or synthetic RNA. Nucleic acids include according to the invention genomic DNA, cDNA, mRNA, recombinantly produced and chemically synthesized molecules. According to the invention, a nucleic acid may be present as a single-stranded or double-stranded and linear or covalently circularly closed molecule. A nucleic acid can, according to the invention, be isolated. The term "isolated nucleic acid" means, according to the invention, that the nucleic acid (i) was amplified in vitro, for example via polymerase chain reaction (PCR), (ii) was produced recombinantly by cloning, (iii) was purified, for example, by cleavage and separation by gel electrophoresis, or (iv) was synthesized, for example, by chemical synthesis. A nucleic can be employed for introduction into, i.e. transfection of, cells, in particular, in the form of RNA which can be prepared by in vitro transcription from a DNA template. The RNA can moreover be modified before application by stabilizing sequences, capping, and polyadenylation.

The term "genetic material" refers to isolated nucleic acid, either DNA or RNA, a section of a double helix, a section of a chromosome, or an organism's or cell's entire genome, in particular its exome or transcriptome.

The term "mutation" refers to a change of or difference in the nucleic acid sequence (nucleotide substitution, addition or deletion) compared to a reference. A "somatic mutation" can occur in any of the cells of the body except the germ cells (sperm and egg) and therefore are not passed on to children. These alterations can (but do not always) cause cancer or other diseases. Preferably a mutation is a non-synonymous mutation. The term "non-synonymous mutation" refers to a mutation, preferably a nucleotide substitution, which does result in an amino acid change such as an amino acid substitution in the translation product.

According to the invention, the term "mutation" includes point mutations, Indels, fusions, chromothripsis and RNA edits.

According to the invention, the term "Indel" describes a special mutation class, defined as a mutation resulting in a colocalized insertion and deletion and a net gain or loss in nucleotides. In coding regions of the genome, unless the length of an indel is a multiple of 3, they produce a frameshift mutation. Indels can be contrasted with a point mutation; where an Indel inserts and deletes nucleotides from a sequence, a point mutation is a form of substitution that replaces one of the nucleotides.

Fusions can generate hybrid genes formed from two previously separate genes. It can occur as the result of a translocation, interstitial deletion, or chromosomal inversion. Often, fusion genes are oncogenes. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. Oncogenic fusion transcripts may also be caused by trans-splicing or read-through events.

According to the invention, the term "chromothripsis" refers to a genetic phenomenon by which specific regions of the genome are shattered and then stitched together via a single devastating event.

According to the invention, the term "RNA edit" or "RNA editing" refers to molecular processes in which the information content in an RNA molecule is altered through a chemical change in the base makeup. RNA editing includes nucleoside modifications such as cytidine (C) to uridine (U) and adenosine (A) to inosine (I) deaminations, as well as non-templated nucleotide additions and insertions. RNA editing in mRNAs effectively alters the amino acid sequence of the encoded protein so that it differs from that predicted by the genomic DNA sequence.

The term "cancer mutation signature" refers to a set of mutations which are present in cancer cells when compared to non-cancerous reference cells.

According to the invention, a "reference" may be used to correlate and compare the results obtained in the methods of the invention from a tumor specimen. Typically the "reference" may be obtained on the basis of one or more normal specimens, in particular specimens which are not affected by a cancer disease, either obtained from a patient or one or more different individuals, preferably healthy individuals, in particular individuals of the same species. A "reference" can be determined empirically by testing a sufficiently large number of normal specimens.

Any suitable sequencing method can be used according to the invention, Next Generation Sequencing (NGS) technologies being preferred. Third Generation Sequencing methods might substitute for the NGS technology in the future to speed up the sequencing step of the method. For clarification purposes: the terms "Next Generation Sequencing" or "NGS" in the context of the present invention mean all novel high throughput sequencing technologies which, in contrast to the "conventional" sequencing methodology known as Sanger chemistry, read nucleic acid templates randomly in parallel along the entire genome by breaking the entire genome into small pieces. Such NGS technologies (also known as massively parallel sequencing technologies) are able to deliver nucleic acid sequence information of a whole genome, exome, transcriptome (all transcribed sequences of a genome) or methylome (all methylated sequences of a genome) in very short time periods, e.g. within 1-2 weeks, preferably within 1-7 days or most preferably within less than 24 hours and allow, in principle, single cell sequencing approaches. Multiple NGS platforms which are commercially available or which are mentioned in the literature can be used in the context of the present invention e.g. those described in detail in Zhang et al. 2011: *The impact of next-generation sequencing on genomics. J. Genet Genomics* 38 (3). 95-109; or in Voelkerding et al. 2009: *Next generation sequencing: From basic research to diagnostics. Clinical chemistry* 55, 641-658. Non-limiting examples of such NGS technologies/platforms are 1) The sequencing-by-synthesis technology known as pyrosequencing implemented e.g. in the GS-FLX 454 Genome Sequencer™ of Roche-associated company 454 Life Sciences (Branford, Conn.), first described in Ronaghi et al. 1998: *A sequencing method based on real-time pyrophosphate"*. Science 281 (5375), 363-365. This technology uses an emulsion PCR in which single-stranded DNA binding beads are encapsulated by vigorous vortexing into aqueous micelles containing PCR reactants surrounded by oil for emulsion PCR amplification. During the pyrosequencing process, light emitted from phosphate molecules during nucleotide incorporation is recorded as the polymerase synthesizes the DNA strand.

2) The sequencing-by-synthesis approaches developed by Solexa (now part of Illumina Inc., San Diego, Calif.) which is based on reversible dye-terminators and implemented e.g. in the Illumina/Solexa Genome Analyzer™ and in the Illumina HiSeq 2000 Genome Analyzer™. In this technology, all four nucleotides are added simultaneously into oligo-primed cluster fragments in flow-cell channels along with DNA polymerase. Bridge amplification extends cluster strands with all four fluorescently labeled nucleotides for sequencing.

3) Sequencing-by-ligation approaches, e.g. implemented in the SOLid™ platform of Applied Biosystems (now Life Technologies Corporation, Carlsbad, Calif.). In this technology, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting bead, each containing only copies of the same DNA molecule, are deposited on a glass slide. As a second example, he Polonator™ G.007 μlatform of Dover Systems (Salem, N.H.) also employs a sequencing-by-ligation approach by using a randomly arrayed, bead-based, emulsion PCR to amplify DNA fragments for parallel sequencing.

4) Single-molecule sequencing technologies such as e.g. implemented in the PacBio RS system of Pacific Biosciences (Menlo Park, Calif.) or in the HeliScope™ platform of Helicos Biosciences (Cambridge, Mass.). The distinct characteristic of this technology is its ability to sequence single DNA or RNA molecules without amplification, defined as Single-Molecule Real Time (SMRT) DNA sequencing. For example, HeliScope uses a highly sensitive fluorescence detection system to directly detect each nucleotide as it is synthesized. A similar approach based on fluorescence resonance energy transfer (FRET) has been developed from Visigen Biotechnology (Houston, Tex.). Other fluorescence-based single-molecule techniques are from U.S. Genomics (GeneEngine™) and Genovoxx (AnyGene™).

5) Nano-technologies for single-molecule sequencing in which various nanostructures are used which are e.g. arranged on a chip to monitor the movement of a polymerase molecule on a single strand during replication. Non-limiting examples for approaches based on nano-technologies are the GridON™ platform of Oxford Nanopore Technologies (Oxford, UK), the hybridization-assisted nano-pore sequencing (HANS™) platforms developed by Nabsys (Providence, R.I.), and the proprietary ligase-based DNA sequencing platform with DNA nanoball (DNB) technology called combinatorial probe-anchor ligation (cPAL™).

6) Electron microscopy based technologies for single-molecule sequencing, e.g. those developed by Light-Speed Genomics (Sunnyvale, Calif.) and Halcyon Molecular (Redwood City, Calif.)

7) Ion semiconductor sequencing which is based on the detection of hydrogen ions that are released during the polymerisation of DNA. For example, Ion Torrent Systems (San Francisco, Calif.) uses a high-density array of micro-machined wells to perform this biochemical process in a massively parallel way. Each well holds a different DNA template. Beneath the wells is an ion-sensitive layer and beneath that a proprietary Ion sensor.

Preferably, DNA and RNA preparations serve as starting material for NGS. Such nucleic acids can be easily obtained from samples such as biological material, e.g. from fresh, flash-frozen or formalin-fixed paraffin embedded tumor tissues (FFPE) or from freshly isolated cells or from CTCs which are present in the peripheral blood of patients. Normal non-mutated genomic DNA or RNA can be extracted from normal, somatic tissue, however germline cells are preferred in the context of the present invention. Germline DNA or RNA is extracted from peripheral blood mononuclear cells (PBMCs) in patients with non-hematological malignancies. Although nucleic acids extracted from FFPE tissues or freshly isolated single cells are highly fragmented, they are suitable for NGS applications.

Several targeted NGS methods for exome sequencing are described in the literature (for review see e.g. Teer and Mullikin 2010: *Human Mol Genet* 19 (2), R145-51), all of which can be used in conjunction with the present invention. Many of these methods (described e.g. as genome capture, genome partitioning, genome enrichment etc.) use hybridization techniques and include array-based (e.g. Hodges et al. 2007: *Nat. Genet.* 39, 1522-1527) and liquid-based (e.g. Choi et al. 2009: *Proc. Nat. Acad. Sci USA* 106, 19096-19101) hybridization approaches. Commercial kits for DNA sample preparation and subsequent exome capture are also available: for example, Illumina Inc. (San Diego, Calif.) offers the TruSeq™ DNA Sample Preparation Kit and the Exome Enrichment Kit TruSeq™ Exome Enrichment Kit.

In order to reduce the number of false positive findings in detecting cancer specific somatic mutations or sequence differences when comparing e.g. the sequence of a tumor sample to the sequence of a reference sample such as the sequence of a germ line sample it is preferred to determine the sequence in replicates of one or both of these sample types. Thus, it is preferred that the sequence of a reference sample such as the sequence of a germ line sample is determined twice, three times or more. Alternatively or additionally, the sequence of a tumor sample is determined twice, three times or more. It may also be possible to determine the sequence of a reference sample such as the sequence of a germ line sample and/or the sequence of a tumor sample more than once by determining at least once the sequence in genomic DNA and determining at least once the sequence in RNA of said reference sample and/or of said tumor sample. For example, by determining the variations between replicates of a reference sample such as a germ line sample the expected rate of false positive (FDR) somatic mutations as a statistical quantity can be estimated. Technical repeats of a sample should generate identical results and any detected mutation in this "same vs. same comparison" is a false positive. In particular, to determine the false discovery rate for somatic mutation detection in a tumor sample relative to a reference sample, a technical repeat of the reference sample can be used as a reference to estimate the number of false positives.

Furthermore, various quality related metrics (e.g. coverage or SNP quality) may be combined into a single quality score using a machine learning approach. For a given somatic variation all other variations with an exceeding quality score may be counted, which enables a ranking of all variations in a dataset.

According to the invention, a high-throughput genome-wide single cell genotyping method can be applied.

In one embodiment of the high-throughput genome-wide single cell genotyping the Fluidigm platform may be used. Such approach may comprise the following steps:

1. Sample tumor tissue/cells and healthy tissue from a given patient.
2. The genetic material is extracted from cancerous and healthy cells and then its exome (DNA) is sequenced using standard next generation sequencing (NGS) protocols. The coverage of the NGS is such that heterozygote alleles with at least 5% frequency can be detected. The transcriptome (RNA) is also extracted from the cancer cells, converted into cDNA and sequenced to determine which genes are expressed by the cancer cells.
3. Non-synonymous expressed single nucleotide variations (SNVs) are identified as described herein. Sites that are SNPs in the healthy tissue are filtered out.
4. N=96 mutations from (3) are selected spanning different frequencies. SNP genotyping assays based on florescence detection are designed and synthesized for these mutations (examples of such assays include: TaqMan based SNP assays by Life Technologies or SNPtype assays by Fluidigm). Assays will include specific target amplification (STA) primers to amplify amplicons containing the given SNV (this is standard in TaqMan and SNPtype assays).
5. Individual cells will be isolated from the tumor and from healthy tissue either by laser microdissection (LMD) or by disaggregation into single-cell suspensions followed by sorting as previously described (Dalerba P. et al. (2011) *Nature Biotechnology* 29: 1120-1127). Cells can either be chosen without pre-selection (i.e., unbiased), or alternatively, cancerous cells can be enriched. Enriching methods include: specific staining, sorting by cell size, histological inspection during LMD, and so on.
6. Individual cells will be isolated in PCR tubes containing a master mix with the STA primers and the amplicons containing the SNVs will be amplified. Alternatively the genome of the single cell will be amplified via whole genome amplification (WGA) as previously described (Frukin D. et al. (2008) *Cancer Research* 68: 5924). Cell lysis will be achieved either via the 95° C. heating step or via a dedicated lysis buffer.
7. STA amplified samples are diluted and loaded onto the Fluidigm genotyping array.
8. Samples from healthy tissue will be used as positive controls to determine homozygote allele clusters (no mutation). Since NGS data indicates that homozygote mutations are extremely rare, typically only two clusters are expected: XX and XY, with X=healthy.

9. The number of arrays that can be executed is not limited, allowing, in practice up to ~1000 single cells to be assayed (~10 arrays). If performed in 384 μlates sample prep can be reduced to a few days.

10. SNVs for each cell are then determined.

In another embodiment of the high-throughput genome-wide single cell genotyping the NGS platform may be used. Such approach may comprise the following steps:

1. Steps 1 through 6 above are identical, except that N (number of SNVs assayed) can be much larger than 96. In case of WGA, several cycles of STA will be performed after. STA primers will contain two universal tag sequences on each primer.

2. After the STA, barcode primers will be PCR amplified into the amplicons. Barcode primers contain unique barcode sequences and the above universal tag sequences. Each cell will thus contain a unique barcode.

3. Amplicons from all cells will be mixed and sequenced via NGS. The practical limitation on the number of cells that can be multiplexed is the number of plates that can be prepared. Since samples can be prepared in 384 μlates, a practical limit would be ~5000 cells.

4. Based on sequence data SNVs (or other structural anomalies) of the individual cells are detected.

For prioritizing antigens, tumor phylogenetic reconstruction based on single cell genotyping ("phylogenetic antigen prioritization") may be used according to the invention. Besides antigen prioritization based on criteria such as expression, the type of mutation (non-synonymous versus other), MHC binding characteristics and so on, a further dimension for prioritization designed to cope with intra and inter-tumor heterogeneity and biopsy bias can be used as described for example below.

1. Identifying the Most Abundant Antigens

The frequency of each SNV can be accurately estimated based on the single cell assay described above in connection with the high-throughput genome-wide single cell genotyping method and the most abundant SNVs present can be selected for providing individualized vaccines for cancer (IVAC).

2. Identifying Primary Basal Antigens Based on Rooted Tree Analysis

NGS data from tumors suggest that homozygote mutations (hits in both alleles) are rare events. Therefore there is no need for haplotyping and a phylogenetic tree of the tumor somatic mutations can be created from the singe cell SNV dataset. The germline sequence will be used to root the tree. Using algorithms to reproduce ancestral sequences the sequences of nodes near the root of the tree will be reproduced. These sequences contain the earliest mutations predicted to exist in the primary tumor (defined here as the primary basal mutations/antigens). Due to the low probability that two mutations will occur on the same alleles in the same position on the genome, the mutations in the ancestral sequences are predicted to be fixed in the tumor.

Prioritizing primary basal antigens is not equivalent to prioritizing the most frequent mutations in the biopsy (although primary basal mutations are expected to be among the most frequent in the biopsy). The reason is the following: say two SNVs appear to be present in all cells derived from a biopsy (and thus have the same frequency—100%), but one mutation is basal and the other is not, then the basal mutation should be selected for IVAC. This is because the basal mutation is likely to present in all regions of the tumor, whereas the latter mutation may be a more recent mutation that by chance was fixed in the region where the biopsy was taken. In addition, basal antigens are likely to exist in metastatic tumors derived from the primary tumor. Therefore by prioritizing basal antigens for IVAC one may greatly increase the chance that IVAC will be able to eradicate the entire tumor and not just a part of the tumor.

If secondary tumors exist and these were also sampled, an evolutionary tree of the all tumors can be estimated. This can improve the robustness of the tree and allow the detection of mutations basal to all tumors.

3. Identifying Antigens that Maximally Span the Tumor(s)

Another approach to obtaining antigens that maximally cover all tumor sites is to take several biopsies from the tumor. One strategy would be to select antigens identified by the NGS analysis to be present in all biopsies. To improve the odds of identifying basal mutations, a phylogenetic analysis based on single cell mutations from all biopsies can be performed.

In case of metastasis, biopsies from all tumors can be obtained and mutations identified via NGS which are common to all tumors can be selected.

4. Using CTCs to Prioritize Antigens that Inhibit Metastasis

It is believed that metastatic tumors are derived from single cells. Therefore by genotyping individual cells extracted from different tumors of a given patient in conjunction with genotyping the patient's circulating tumor cells (CTCs), one can reconstruct the evolutionary history of the cancer. The expectation is to observe the metastatic tumor evolving from the original tumor through a clade of CTCs derived from the primary tumor.

Below (unbiased method to identify, count and genetically probe CTCs) we describe an extension of the above described high-throughput genome-wide single cell genotyping method for an unbiased isolation and genomic analysis CTCs. Using the analysis described above, one can then reconstruct a phylogenetic tree of the primer tumor, CTCs and secondary tumors arising from metastasis (if they exist). Based on this tree one can identify mutations (passenger or driver) that occurred at the time or closely after CTCs first detached from the primary tumor. The expectation is that the genomes of CTCs arising from the primary tumor are evolutionary more similar to the primary tumor genomes than to secondary tumor genomes. Furthermore it is expected that the genomes of CTCs arising from the primary tumor will contain unique mutations that are fixed in the secondary tumors, or that will likely be fixed if secondary tumors will be formed in the future. These unique mutations can be prioritized for IVAC to target (or prevent) metastasis.

The advantage of prioritizing CTC mutations versus primary basal mutations is that antigens derived from CTCs can mobilize T cells specifically to target metastasis, and therefore will be an independent arm from the T cells targeting the primary tumor (using different antiges). In addition, if there are few (or no) secondary tumors, then the chance for immune escape from CTC derived antigens is expected to be lower as the probably for tumor escape should scale with the number of cancer cells carrying the given antigen.

5. Identifying Antigens Co-Occurring on the Same Cell (the "Cocktail" IVAC)

It is believed that the tumor evolves to suppress mutations due to the selection pressure of the immune system and therapy. Cancer vaccines targeting multiple antigens that co-occur on the same cell and that are also frequent in the tumor have a greater chance of overriding tumor escape mechanisms and therefore reduce the chance for relapse. Such "cocktail vaccines" would be analogous to the anti-retroviral combination therapy for HIV+ patients. Co-occurring mutations can be identified by phylogenetic analysis or by inspecting the SNV alignment of all cells.

Furthermore, according to the invention, an unbiased method to identify, count and genetically probe CTCs can be used. Such approach may comprise the following steps:

1. Obtain biopsy of tumor(s) and determine atlas of somatic mutations.
2. Option 1: Select N≥96 mutations for further investigation based on previously established prioritization schemes.
   Option 2: Perform single cell assay (see above described high-throughput genome-wide single cell genotyping method) followed phylogenetic analysis to select N≥96 primary basal mutations and possibly more recent mutations to maximize diversity. The former mutations are useful for identifying the CTCs (see below), and the latter for generating a phylogenetic analysis (see section "Identifying antigens co-occurring on the same cell (the "cocktail" IVAC")).
3. Obtain whole blood from the cancer patient
4. Lyse red blood cells
5. Remove white blood cells by depleting CD45+ cells (e.g., via sorting, magnetic beads conjugated to anti CD45 antibody, etc.) to enrich for CTCs.
6. Remove free DNA by DNAase digestion. The origin of free DNA can be DNA present in the blood or DNA from dead cells.
7. Sort remaining cells into PCR tubes, perform the STA (based on selected mutations) and screen on Fluidigm (above described high-throughput genome-wide single cell genotyping method). CTCs should generally be positive for multiple SNVs.
8. Cells identified as cancerous (=CTCs) can be then be further analyzed phylogenetically based on the panel of SNVs screened (see section "Identifying antigens co-occurring on the same cell (the "cocktail" IVAC")).

It is also possible to combine this method with previous established methods for isolated CTCs. For example, one can sort for EpCAM+ cells, or cells positive for cytokeratins (Rao C G. et al. (2005) International journal of oncology 27: 49; Allard W J. et al. (2004) Clinical Cancer Research 10: 6897-6904). These putative CTCs can then be verified/profiled on the Fluidigm/NGS to derive their mutations.

This method can be used to count CTCs. Since the method does not rely on one particular marker, which may nor may not be expressed by the cancer cells, but rather on the mutation profile of cancer somatic mutations unique to the patient, this is an unbiased method to detect and enumerate CTCs.

According to the invention, an approach involving tumor phylogenetic reconstruction based on single cell genotyping to enrich for driver mutations ("phylogenetic filtering") may be used.

In one embodiment of this approach, a pan-tumor phylogenetic analysis to recover driver mutations is performed.

For example, driver mutations from n−1 tumors may be detected.

In the above section "Identifying primary basal antigens based on rooted tree analysis" we describe a method to recover ancestral sequences and/or identify cells that have sequences close to the root of the tree. The number of mutations in these sequences is expected to be significantly less than the number of mutations in the bulk sample of the cancer since by definition these are sequences close to the root of the tree. Therefore, by selecting sequences close to the root of the tree many passenger mutations are expected to be "phylogenetically filtered" out. This procedure has the potential to greatly enrich for driver mutations. Driver mutations can then be used to identify/selects treatment for a patient or can be used as leads for novel therapies.

In another example, driver mutations from n>1 tumors of a given type may be detected.

By reconstructing primary basal mutations from many tumors of a particular type one can greatly increase the chance of detecting driver mutations. Since basal sequences near the root of the tree filter out many passenger mutations, the signal to noise ratio in detecting driver mutations is expected to greatly increase. This method therefore has the potential to detect (1) less frequent driver mutation (2) frequent driver mutations from less samples.

In another embodiment of the approach involving tumor phylogenetic reconstruction based on single cell genotyping to enrich for driver mutations ("phylogenetic filtering"), a phylogenetic analysis to recover metastasis causing driver mutations is performed.

In the above section "Using CTCs to prioritize antigens that inhibit metastasis" we describe a method to detect CTC-associated mutations. This method can also be used to enrich for driver mutations leading to metastasis. For example, by mapping the combined phylogeny of the primer tumor, secondary tumors and CTCs, CTCs derived from the primary tumor should connect between the clades of the primary secondary tumors. Such a phylogenetic analysis can help pinpoint the mutations unique at this transition between primer and secondary tumors. A fraction of these mutations can be driver mutations. Furthermore, by comparing unique CTC mutations from different instances of the same cancer (i.e., n>1 tumors), one can further enrich for the unique driver mutations causing metastasis.

According to the invention, phylogenetic analysis to identify primary versus secondary tumors may be used.

In case of metastasis, if all tumors are sampled, a rooted tree can be used to predict the temporal order that tumors appeared: which tumor is the primary tumor (nodes closest to the root of the tree) and which tumors are the most recent ones. This can be helpful in cases where it is difficult to determine which tumor is the primary.

In the context of the present invention, the term "RNA" relates to a molecule which comprises at least one ribonucleotide residue and preferably being entirely or substantially composed of ribonucleotide residues. "Ribonucleotide" relates to a nucleotide with a hydroxyl group at the 2'-position of a β-D-ribofuranosyl group. The term "RNA" comprises double-stranded RNA, single-stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA". The term "mRNA" means "messenger-RNA" and relates to a "transcript" which is generated by using a DNA template and encodes a peptide or polypeptide. Typically, an mRNA comprises a 5'-UTR, a protein coding region, and a 3'-UTR. mRNA only possesses limited half-life in cells and in vitro. In the context of the present invention, mRNA may be generated by in vitro transcription from a DNA template. The in vitro transcription methodology is known to the skilled person. For example, there is a variety of in vitro transcription kits commercially available.

According to the invention, the stability and translation efficiency of RNA may be modified as required. For example, RNA may be stabilized and its translation increased by one or more modifications having a stabilizing effects and/or increasing translation efficiency of RNA. Such modifications are described, for example, in PCT/EP2006/009448 incorporated herein by reference. In order to increase expression of the RNA used according to the present invention, it may be modified within the coding region, i.e. the sequence encoding the expressed peptide or protein, preferably without altering the sequence of the expressed peptide or protein, so as to increase the GC-content to increase mRNA stability and to perform a codon optimization and, thus, enhance translation in cells.

The term "modification" in the context of the RNA used in the present invention includes any modification of an RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA and/or enhance translation of RNA if attached thereto, preferably in vivo and/or in a cell.

Preferably, the 5' end of the RNA includes a Cap structure having the following general formula:

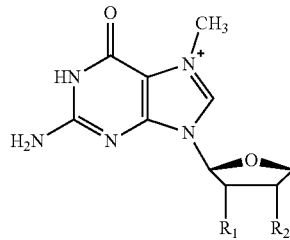 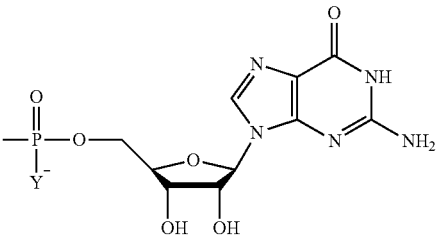

wherein $R_1$ and $R_2$ are independently hydroxy or methoxy and $W^-$, $X^-$ and $Y^-$ are independently oxygen, sulfur, selenium, or $BH_3$. In a preferred embodiment, $R_1$ and $R_2$ are hydroxy and $W^-$, $X^-$ and $Y^-$ are oxygen. In a further preferred embodiment, one of $R_1$ and $R_2$, preferably $R_1$ is hydroxy and the other is methoxy and $W^-$, $X^-$ and $Y^-$ are oxygen. In a further preferred embodiment, $R_1$ and $R_2$ are hydroxy and one of $W^-$, $X^-$ and $Y^-$, preferably $X^-$ is sulfur, selenium, or $BH_3$, preferably sulfur, while the other are oxygen. In a further preferred embodiment, one of $R_1$ and $R_2$, preferably $R_2$ is hydroxy and the other is methoxy and one of $W^-$, $X^-$ and $Y^-$, preferably $X^-$ is sulfur, selenium, or $BH_3$, preferably sulfur while the other are oxygen.

In the above formula, the nucleotide on the right hand side is connected to the RNA chain through its 3' group.

Those Cap structures wherein at least one of $W^-$, $X^-$ and $Y^-$ is sulfur, i.e. which have a phosphorothioate moiety, exist in different diastereoisomeric forms all of which are encompassed herein. Furthermore, the present invention encompasses all tautomers and stereoisomers of the above formula.

For example, the Cap structure having the above structure wherein $R_1$ is methoxy, $R_2$ is hydroxy, $X^-$ is sulfur and $W^-$ and $Y^-$ are oxygen exists in two diastereoisomeric forms (Rp and Sp). These can be resolved by reverse phase HPLC and are named D1 and D2 according to their elution order from the reverse phase HPLC column. According to the invention, the D1 isomer of $m_2^{7,2'-O}Gpp_sG$ is particularly preferred.

Providing an RNA with a 5'-cap or 5'-cap analog may be achieved by in vitro transcription of a DNA template in presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the exchange of the existing 3'-UTR with or the insertion of one or more, preferably two copies of a 3'-UTR derived from a globin gene, such as alpha2-globin, alpha1-globin, beta-globin, preferably beta-globin, more preferably human beta-globin.

RNA having an unmasked poly-A sequence is translated more efficiently than RNA having a masked poly-A sequence. The term "poly(A) tail" or "poly-A sequence" relates to a sequence of adenyl (A) residues which typically is located on the 3'-end of a RNA molecule and "unmasked poly-A sequence" means that the poly-A sequence at the 3' end of an RNA molecule ends with an A of the poly-A sequence and is not followed by nucleotides other than A located at the 3' end, i.e. downstream, of the poly-A sequence. Furthermore, a long poly-A sequence of about 120 base pairs results in an optimal transcript stability and translation efficiency of RNA.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. To further increase stability and/or expression of the RNA used according to the invention, the poly-A sequence can be unmasked.

In addition, incorporation of a 3'-non translated region (UTR) into the 3'-non translated region of an RNA molecule can result in an enhancement in translation efficiency. A synergistic effect may be achieved by incorporating two or more of such 3'-non translated regions. The 3'-non translated regions may be autologous or heterologous to the RNA into which they are introduced. In one particular embodiment the 3'-non translated region is derived from the human β-globin gene.

A combination of the above described modifications, i.e. incorporation of a poly-A sequence, unmasking of a poly-A sequence and incorporation of one or more 3'-non translated regions, has a synergistic influence on the stability of RNA and increase in translation efficiency.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

Of course, if according to the present invention it is desired to decrease stability and/or translation efficiency of RNA, it is possible to modify RNA so as to interfere with the function of elements as described above increasing the stability and/or translation efficiency of RNA.

The term "expression" is used according to the invention in its most general meaning and comprises the production of RNA and/or peptides or polypeptides, e.g. by transcription and/or translation. With respect to RNA, the term "expression" or "translation" relates in particular to the production of peptides or polypeptides. It also comprises partial expression of nucleic acids. Moreover, expression can be transient or stable.

According to the invention, the term expression also includes an "aberrant expression" or "abnormal expression". "Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The term "translation" according to the invention relates to the process in the ribosomes of a cell by which a strand of messenger RNA directs the assembly of a sequence of amino acids to make a peptide or polypeptide.

Expression control sequences or regulatory sequences, which according to the invention may be linked functionally with a nucleic acid, can be homologous or heterologous with respect to the nucleic acid. A coding sequence and a regulatory sequence are linked together "functionally" if they are bound together covalently, so that the transcription or translation of the coding sequence is under the control or under the influence of the regulatory sequence. If the coding sequence is to be translated into a functional protein, with functional linkage of a regulatory sequence with the coding sequence, induction of the regulatory sequence leads to a transcription of the coding sequence, without causing a reading frame shift in the coding sequence or inability of the coding sequence to be translated into the desired protein or peptide.

The term "expression control sequence" or "regulatory sequence" comprises, according to the invention, promoters, ribosome-binding sequences and other control elements, which control the transcription of a nucleic acid or the translation of the derived RNA. In certain embodiments of the invention, the regulatory sequences can be controlled. The precise structure of regulatory sequences can vary depending on the species or depending on the cell type, but generally comprises 5'-untranscribed and 5'- and 3'-untranslated sequences, which are involved in the initiation of transcription or translation, such as TATA-box, capping-sequence, CAAT-sequence and the like. In particular, 5'-untranscribed regulatory sequences comprise a promoter region that includes a promoter sequence for transcriptional control of the functionally bound gene. Regulatory sequences can also comprise enhancer sequences or upstream activator sequences.

Preferably, according to the invention, the RNA to be expressed in a cell is introduced into said cell. In one embodiment of the methods according to the invention, the RNA that is to be introduced into a cell is obtained by in vitro transcription of an appropriate DNA template.

According to the invention, terms such as "RNA capable of expressing" and "RNA encoding" are used interchangeably herein and with respect to a particular peptide or polypeptide mean that the RNA, if present in the appropriate environment, preferably within a cell, can be expressed to produce said peptide or polypeptide. Preferably, RNA according to the invention is able to interact with the cellular translation machinery to provide the peptide or polypeptide it is capable of expressing.

Terms such as "transferring", "introducing" or "transfecting" are used interchangeably herein and relate to the introduction of nucleic acids, in particular exogenous or heterologous nucleic acids, in particular RNA into a cell. According to the present invention, the cell can form part of an organ, a tissue and/or an organism. According to the present invention, the administration of a nucleic acid is either achieved as naked nucleic acid or in combination with an administration reagent. Preferably, administration of nucleic acids is in the form of naked nucleic acids. Preferably, the RNA is administered in combination with stabilizing substances such as RNase inhibitors. The present invention also envisions the repeated introduction of nucleic acids into cells to allow sustained expression for extended time periods.

Cells can be transfected with any carriers with which RNA can be associated, e.g. by forming complexes with the RNA or forming vesicles in which the RNA is enclosed or encapsulated, resulting in increased stability of the RNA compared to naked RNA. Carriers useful according to the invention include, for example, lipid-containing carriers such as cationic lipids, liposomes, in particular cationic liposomes, and micelles, and nanoparticles. Cationic lipids may form complexes with negatively charged nucleic acids. Any cationic lipid may be used according to the invention.

Preferably, the introduction of RNA which encodes a peptide or polypeptide into a cell, in particular into a cell present in vivo, results in expression of said peptide or polypeptide in the cell. In particular embodiments, the targeting of the nucleic acids to particular cells is preferred. In such embodiments, a carrier which is applied for the administration of the nucleic acid to a cell (for example, a retrovirus or a liposome), exhibits a targeting molecule. For example, a molecule such as an antibody which is specific for a surface membrane protein on the target cell or a ligand for a receptor on the target cell may be incorporated into the nucleic acid carrier or may be bound thereto. In case the nucleic acid is administered by liposomes, proteins which bind to a surface membrane protein which is associated with endocytosis may be incorporated into the liposome formulation in order to enable targeting and/or uptake. Such proteins encompass capsid proteins of fragments thereof which are specific for a particular cell type, antibodies against proteins which are internalized, proteins which target an intracellular location etc.

According to the present invention, the term "peptide" refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "polypeptide" or "protein" refers to large peptides, preferably to peptides with more than 100 amino acid residues, but in general the terms "peptide", "polypeptide" and "protein" are synonyms and are used interchangeably herein.

According to the invention, the term "sequence change" with respect to peptides or proteins relates to amino acid insertion variants, amino acid addition variants, amino acid deletion variants and amino acid substitution variants, preferably amino acid substitution variants. All these sequence changes according to the invention may potentially create new epitopes.

Amino acid insertion variants comprise insertions of single or two or more amino acids in a particular amino acid sequence.

Amino acid addition variants comprise amino- and/or carboxy-terminal fusions of one or more amino acids, such as 1, 2, 3, 4 or 5, or more amino acids.

Amino acid deletion variants are characterized by the removal of one or more amino acids from the sequence, such as by removal of 1, 2, 3, 4 or 5, or more amino acids.

Amino acid substitution variants are characterized by at least one residue in the sequence being removed and another residue being inserted in its place.

The term "derived" means according to the invention that a particular entity, in particular a particular sequence, is present in the object from which it is derived, in particular an organism or molecule. In the case of amino acid sequences, especially particular sequence regions, "derived" in particular means that the relevant amino acid sequence is derived from an amino acid sequence in which it is present.

The term "cell" or "host cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transformed or transfected with an exogenous nucleic acid. The term "cell" includes according to the invention prokaryotic cells (e.g., E. coli) or eukaryotic cells (e.g., dendritic cells, B cells, CHO cells, COS cells, K562 cells, HEK293 cells, HELA cells, yeast cells, and insect cells). The exogenous nucleic acid may be found inside the cell (i) freely dispersed as such, (ii) incorporated in a recombinant vector, or (iii) integrated into the host cell genome or mitochondrial DNA. Mammalian cells are particularly preferred, such as cells from humans, mice, hamsters, pigs, goats, and primates. The cells may be derived from a large number of tissue types and include primary cells and cell lines. Specific examples include keratinocytes, peripheral blood leukocytes, bone marrow stem cells, and embryonic stem cells. In further embodiments, the cell is an antigen-presenting cell, in particular a dendritic cell, a monocyte, or macrophage.

A cell which comprises a nucleic acid molecule preferably expresses the peptide or polypeptide encoded by the nucleic acid.

The term "clonal expansion" refers to a process wherein a specific entity is multiplied. In the context of the present invention, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

Terms such as "reducing" or "inhibiting" relate to the ability to cause an overall decrease, preferably of 5% or greater, 10% or greater, 20% or greater, more preferably of 50% or greater, and most preferably of 75% or greater, in the level. The term "inhibit" or similar phrases includes a complete or essentially complete inhibition, i.e. a reduction to zero or essentially to zero.

Terms such as "increasing", "enhancing", "promoting" or "prolonging" preferably relate to an increase, enhancement, promotion or prolongation by about at least 10%, preferably at least 20%, preferably at least 30%, preferably at least 40%, preferably at least 50%, preferably at least 80%, preferably at least 100%, preferably at least 200% and in particular at least 300%. These terms may also relate to an increase, enhancement, promotion or prolongation from zero or a non-measurable or non-detectable level to a level of more than zero or a level which is measurable or detectable.

The agents, compositions and methods described herein can be used to treat a subject with a disease, e.g., a disease characterized by the presence of diseased cells expressing an antigen and presenting an antigen peptide. Particularly preferred diseases are cancer diseases. The agents, compositions and methods described herein may also be used for immunization or vaccination to prevent a disease described herein.

According to the invention, the term "disease" refers to any pathological state, including cancer diseases, in particular those forms of cancer diseases described herein.

The term "normal" refers to the healthy state or the conditions in a healthy subject or tissue, i.e., non-pathological conditions, wherein "healthy" preferably means non-cancerous.

"Disease involving cells expressing an antigen" means according to the invention that expression of the antigen in cells of a diseased tissue or organ is detected. Expression in cells of a diseased tissue or organ may be increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases involving or being associated with cells expressing an antigen include cancer diseases.

Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not.

Malignant tumor is essentially synonymous with cancer. Malignancy, malignant neoplasm, and malignant tumor are essentially synonymous with cancer.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

A benign tumor is a tumor that lacks all three of the malignant properties of a cancer. Thus, by definition, a benign tumor does not grow in an unlimited, aggressive manner, does not invade surrounding tissues, and does not spread to non-adjacent tissues (metastasize).

Neoplasm is an abnormal mass of tissue as a result of neoplasia. Neoplasia (new growth in Greek) is the abnormal proliferation of cells. The growth of the cells exceeds, and is uncoordinated with that of the normal tissues around it. The growth persists in the same excessive manner even after cessation of the stimuli. It usually causes a lump or tumor. Neoplasms may be benign, pre-malignant or malignant.

"Growth of a tumor" or "tumor growth" according to the invention relates to the tendency of a tumor to increase its size and/or to the tendency of tumor cells to proliferate.

For purposes of the present invention, the terms "cancer" and "cancer disease" are used interchangeably with the terms "tumor" and "tumor disease".

Cancers are classified by the type of cell that resembles the tumor and, therefore, the tissue presumed to be the origin of the tumor. These are the histology and the location, respectively.

The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases and relapse of cancer.

The main types of lung cancer are small cell lung carcinoma (SCLC) and non-small cell lung carcinoma (NSCLC). There are three main sub-types of the non-small cell lung carcinomas: squamous cell lung carcinoma, adenocarcinoma, and large cell lung carcinoma. Adenocarcinomas account for approximately 10% of lung cancers. This cancer usually is seen peripherally in the lungs, as opposed to small cell lung cancer and squamous cell lung cancer, which both tend to be more centrally located.

Skin cancer is a malignant growth on the skin. The most common skin cancers are basal cell cancer, squamous cell cancer, and melanoma. Malignant melanoma is a serious type of skin cancer. It is due to uncontrolled growth of pigment cells, called melanocytes.

According to the invention, a "carcinoma" is a malignant tumor derived from epithelial cells. This group represents the most common cancers, including the common forms of breast, prostate, lung and colon cancer.

"Bronchiolar carcinoma" is a carcinoma of the lung, thought to be derived from epithelium of terminal bronchioles, in which the neoplastic tissue extends along the alveolar walls and grows in small masses within the alveoli. Mucin may be demonstrated in some of the cells and in the material in the alveoli, which also includes denuded cells.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

Renal cell carcinoma also known as renal cell cancer or renal cell adenocarcinoma is a kidney cancer that originates in the lining of the proximal convoluted tubule, the very small tubes in the kidney that filter the blood and remove waste products. Renal cell carcinoma is by far the most common type of kidney cancer in adults and the most lethal of all the genitorurinary tumors. Distinct subtypes of renal cell carcinoma are clear cell renal cell carcinoma and papillary renal cell carcinoma. Clear cell renal cell carcinoma is the most common form of renal cell carcinoma. When seen under a microscope, the cells that make up clear cell renal cell carcinoma appear very pale or clear. Papillary renal cell carcinoma is the second most common subtype. These cancers form little finger-like projections (called papillae) in some, if not most, of the tumors.

Lymphoma and leukemia are malignancies derived from hematopoietic (blood-forming) cells.

Blastic tumor or blastoma is a tumor (usually malignant) which resembles an immature or embryonic tissue. Many of these tumors are most common in children.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

In ovarian cancer, metastasis can occur in the following ways: by direct contact or extension, it can invade nearby tissue or organs located near or around the ovary, such as the fallopian tubes, uterus, bladder, rectum, etc.; by seeding or shedding into the abdominal cavity, which is the most common way ovarian cancer spreads. Cancer cells break off the surface of the ovarian mass and "drop" to other structures in the abdomen such as the liver, stomach, colon or diaphragm; by breaking loose from the ovarian mass, invading the lymphatic vessels and then traveling to other areas of the body or distant organs such as the lung or liver; by breaking loose from the ovarian mass, invading the blood system and traveling to other areas of the body or distant organs.

According to the invention, metastatic ovarian cancer includes cancer in the fallopian tubes, cancer in organs of the abdomen such as cancer in the bowel, cancer in the uterus, cancer in the bladder, cancer in the rectum, cancer in the liver, cancer in the stomach, cancer in the colon, cancer in the diaphragm, cancer in the lungs, cancer in the lining of the abdomen or pelvis (peritoneum), and cancer in the brain. Similarly, metastatic lung cancer refers to cancer that has spread from the lungs to distant and/or several sites in the body and includes cancer in the liver, cancer in the adrenal glands, cancer in the bones, and cancer in the brain.

The term "circulating tumor cells" or "CTCs" relates to cells that have detached from a primary tumor or tumor metastases and circulate in the bloodstream. CTCs may constitute seeds for subsequent growth of additional tumors (metastasis) in different tissues. Circulating tumor cells are found in frequencies in the order of 1-10 CTC per mL of whole blood in patients with metastatic disease. Research methods have been developed to isolate CTC.

Several research methods have been described in the art to isolate CTCs, e.g. techniques which use of the fact that epithelial cells commonly express the cell adhesion protein EpCAM, which is absent in normal blood cells. Immunomagnetic bead-based capture involves treating blood specimens with antibody to EpCAM that has been conjugated with magnetic particles, followed by separation of tagged cells in a magnetic field. Isolated cells are then stained with antibody to another epithelial marker, cytokeratin, as well as a common leukocyte marker CD45, so as to distinguish rare CTCs from contaminating white blood cells. This robust and semi-automated approach identifies CTCs with an average yield of approximately 1 CTC/mL and a purity of 0.1% (Allard et al., 2004: *Clin Cancer Res* 10, 6897-6904). A second method for isolating CTCs uses a microfluidic-based CTC capture device which involves flowing whole blood through a chamber embedded with 80,000 microposts that have been rendered functional by coating with antibody to EpCAM. CTCs are then stained with secondary antibodies against either cytokeratin or tissue specific markers, such as PSA in prostate cancer or HER2 in breast cancer and are visualized by automated scanning of microposts in multiple planes along three dimensional coordinates. CTC-chips are able to identifying cytokerating-positive circulating tumor cells in patients with a median yield of 50 cells/ml and purity ranging from 1-80% (Nagrath et al., 2007: *Nature* 450, 1235-1239). Another possibility for isolating CTCs is using the CellSearch Circulating Tumor Cell (CTC) Test from Veridex, LLC (Raritan, N.J.) which captures, identifies, and counts CTCs in a tube of blood. The CellSearch™ system is a U.S. Food and Drug Administration (FDA) approved methodology for enumeration of CTC in whole blood which is based on a combination of immunomagnetic labeling and automated digital microscopy. There are other methods for isolating CTCs described in the literature all of which can be used in conjunction with the present invention.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

By "treat" is meant to administer a compound or composition as described herein to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject. In particular, the term "treatment of a disease" includes curing, shortening the duration, ameliorating, preventing, slowing down or inhibiting progression or worsening, or preventing or delaying the onset of a disease or the symptoms thereof.

By "being at risk" is meant a subject, i.e. a patient, that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

The term "immunotherapy" relates to a treatment involving activation of a specific immune reaction. In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for a tumor, as described above, would be a candidate for therapy to prevent a tumor.

A prophylactic administration of an immunotherapy, for example, a prophylactic administration of the composition of the invention, preferably protects the recipient from the development of a disease. A therapeutic administration of an immunotherapy, for example, a therapeutic administration of the composition of the invention, may lead to the inhibition of the progress/growth of the disease. This comprises the deceleration of the progress/growth of the disease, in particular a disruption of the progression of the disease, which preferably leads to elimination of the disease.

Immunotherapy may be performed using any of a variety of techniques, in which agents provided herein function to remove diseased cells from a patient. Such removal may take place as a result of enhancing or inducing an immune response in a patient specific for an antigen or a cell expressing an antigen.

Within certain embodiments, immunotherapy may be active immunotherapy, in which treatment relies on the in vivo stimulation of the endogenous host immune system to react against diseased cells with the administration of immune response-modifying agents (such as polypeptides and nucleic acids as provided herein).

The agents and compositions provided herein may be used alone or in combination with conventional therapeutic regimens such as surgery, irradiation, chemotherapy and/or bone marrow transplantation (autologous, syngeneic, allogeneic or unrelated).

The term "immunization" or "vaccination" describes the process of treating a subject with the purpose of inducing an immune response for therapeutic or prophylactic reasons.

The term "in vivo" relates to the situation in a subject.

The terms "subject", "individual", "organism" or "patient" are used interchangeably and relate to vertebrates, preferably mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans. The term "subject" may also include a patient, i.e., an animal, preferably a human having a disease, preferably a disease as described herein.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "heterologous" is used to describe something consisting of multiple different elements. As an example, the transfer of one individual's bone marrow into a different individual constitutes a heterologous transplant. A heterologous gene is a gene derived from a source other than the subject.

As part of the composition for an immunization or a vaccination, preferably one or more agents as described herein are administered together with one or more adjuvants for inducing an immune response or for increasing an immune response. The term "adjuvant" relates to compounds which prolongs or enhances or accelerates an immune response. The composition of the present invention preferably exerts its effect without addition of adjuvants. Still, the composition of the present application may contain any known adjuvant. Adjuvants comprise a heterogeneous group of compounds such as oil emulsions (e.g., Freund's adjuvants), mineral compounds (such as alum), bacterial products (such as *Bordetella pertussis* toxin), liposomes, and immune-stimulating complexes. Examples for adjuvants are monophosphoryl-lipid-A (MPL SmithKline Beecham). Saponins such as QS21 (SmithKline Beecham), DQS21 (SmithKline Beecham; WO 96/33739), QS7, QS17, QS18, and QS-L1 (So et al., 1997, Mol. Cells 7: 178-186), incomplete Freund's adjuvants, complete Freund's adjuvants, vitamin E, montanid, alum, CpG oligonucleotides (Krieg et al., 1995, Nature 374: 546-549), and various water-in-oil emulsions which are prepared from biologically degradable oils such as squalene and/or tocopherol.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (cf. *Science* 268:1432-1434, 1995), GM-CSF and IL-18.

There are a number of compounds which enhance an immune response and which therefore may be used in a vaccination. Said compounds comprise co-stimulating molecules provided in the form of proteins or nucleic acids such as B7-1 and B7-2 (CD80 and CD86, respectively).

According to the invention, a "tumor specimen" is a sample such as a bodily sample containing tumor or cancer cells such as circulating tumor cells (CTC), in particular a tissue sample, including body fluids, and/or a cellular sample. According to the invention, a "non-tumorigenous specimen" is a sample such as a bodily sample not containing tumor or cancer cells such as circulating tumor cells (CTC), in particular a tissue sample, including body fluids, and/or a cellular sample. Such bodily samples may be obtained in the conventional manner such as by tissue biopsy, including punch biopsy, and by taking blood, bronchial aspirate, sputum, urine, feces or other body fluids. According to the invention, the term "sample" also includes processed samples such as fractions or isolates of biological samples, e.g. nucleic acid or cell isolates.

The therapeutically active agents, vaccines and compositions described herein may be administered via any conventional route, including by injection or infusion. The administration may be carried out, for example, orally, intravenously, intraperitoneally, intramuscularly, subcutaneously or transdermally. In one embodiment, administration is carried out intranodally such as by injection into a lymph node. Other forms of administration envision the in vitro transfection of antigen presenting cells such as dendritic cells with nucleic acids described herein followed by administration of the antigen presenting cells.

The agents described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The pharmaceutical compositions of the invention are preferably sterile and contain an effective amount of the therapeutically active substance to generate the desired reaction or the desired effect.

The pharmaceutical compositions of the invention are generally administered in pharmaceutically compatible amounts and in pharmaceutically compatible preparation. The term "pharmaceutically compatible" refers to a nontoxic material which does not interact with the action of the active component of the pharmaceutical composition. Preparations of this kind may usually contain salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the invention may comprise a pharmaceutically compatible carrier. The term "carrier" refers to an organic or inorganic component, of a natural or synthetic nature, in which the active component is combined in order to facilitate application. According to the invention, the term "pharmaceutically compatible carrier" includes one or more compatible solid or liquid fillers, diluents or encapsulating substances, which are suitable for administration to a patient. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, solutions, suspensions, syrups, elixirs or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1:
Top: Process to discover and prioritize likely immunogenic somatic mutations in bulk tumor samples. Bottom: Process as applied to the B16 and Black6 system.

Figure 2:
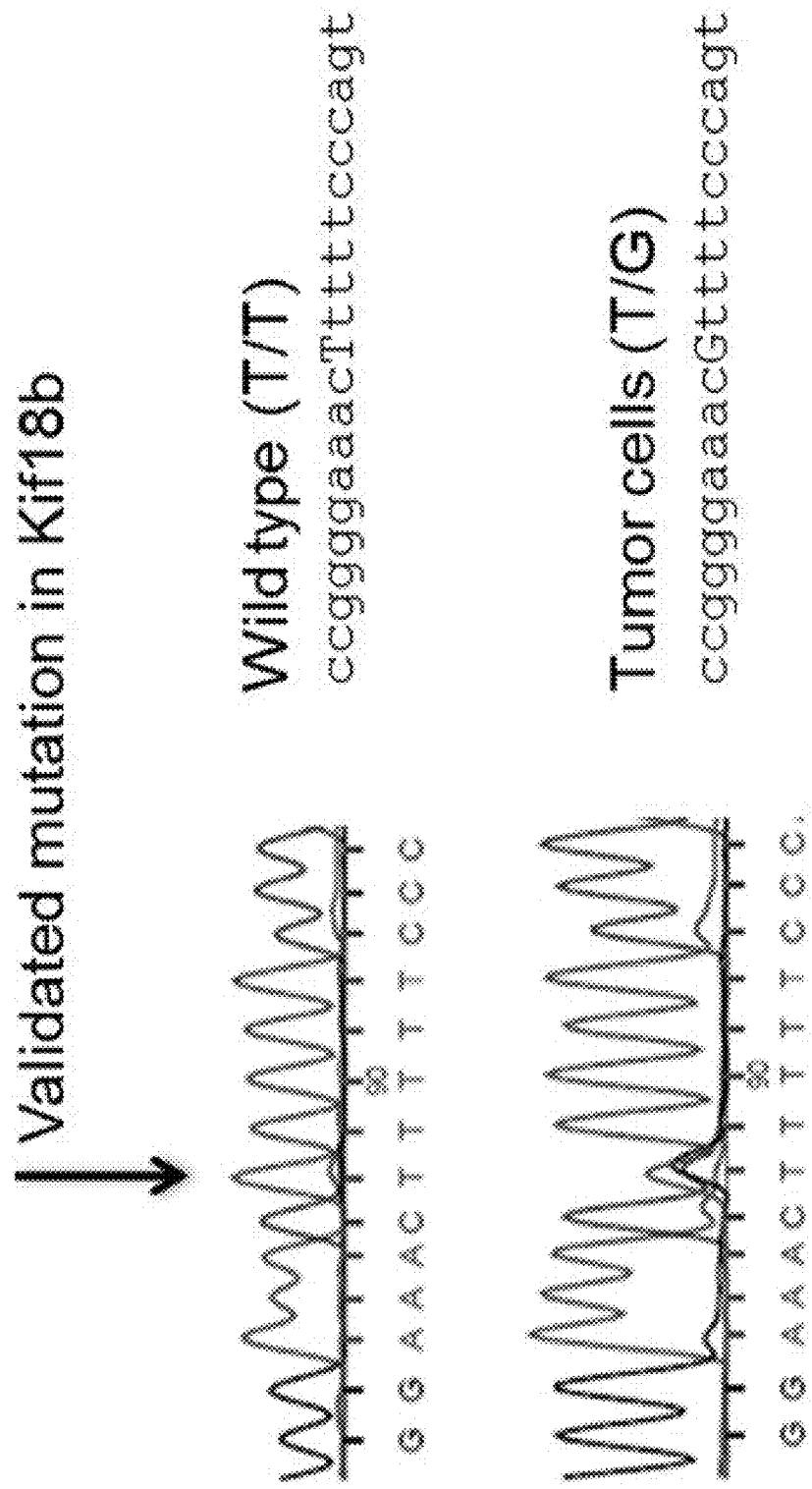

FIG. 2: Example Validated Mutation In KIf18b
A mutation identified in gene Kif18b by NGS exome-sequencing that was confirmed by Sanger sequencing. In the wild type cells, the sequence is T/T. In the tumor cells, the sequence is a mix of T/G.

Figure 3:
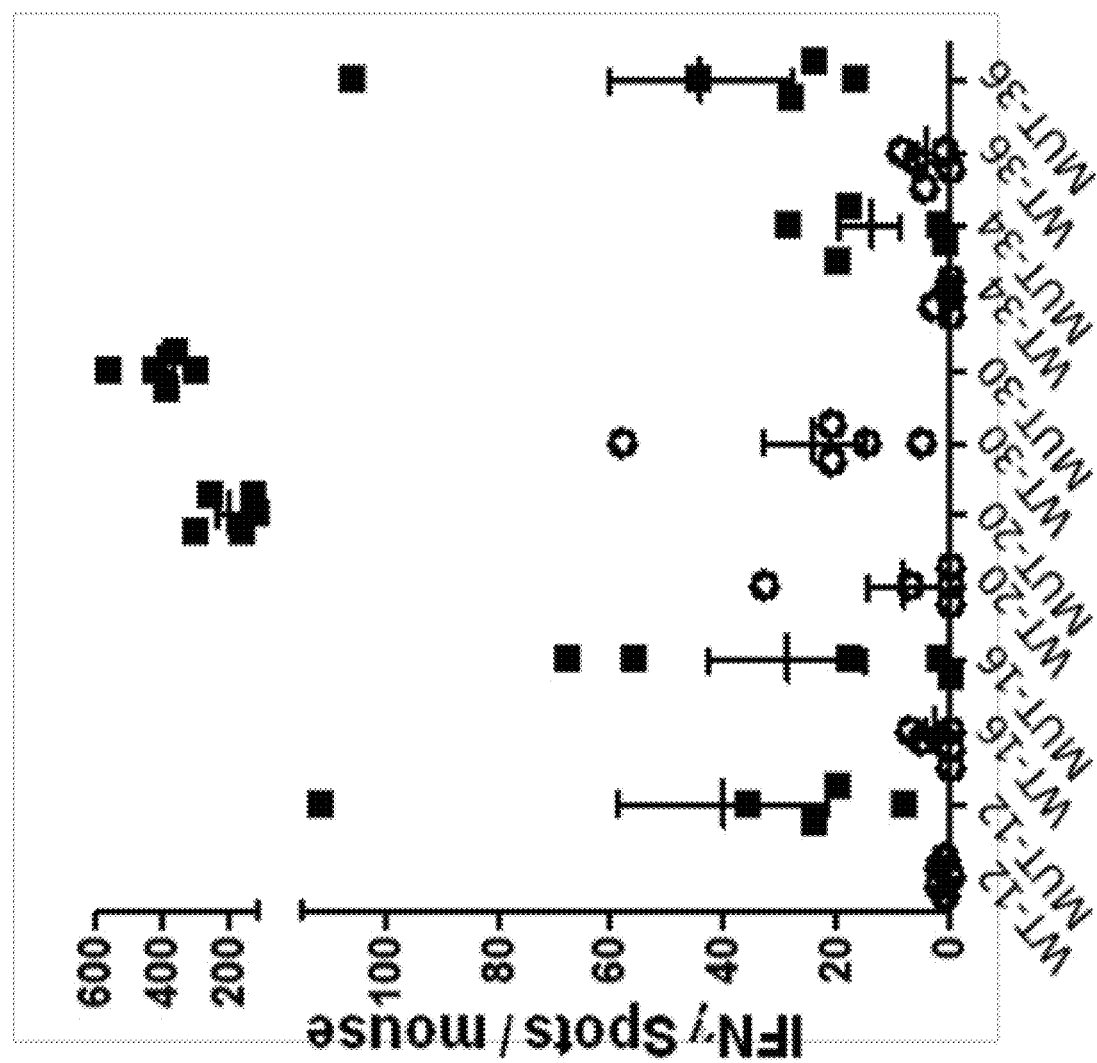

FIG. 3: Immunologic reactivity against mutated sequences

Mice (n=5) were immunized twice (d0, d7) with mutated peptide sequences (100 µg+50 µg PolyI:C; s.c.). At day 12 mice were sacrificed and the spleen cells harvested. IFNγ ELISpot was performed using $5 \times 10^5$ spleen cells/well as effectors and $5 \times 10^4$ bone marrow dendritic cells loaded with peptides (2 µg/ml for 2 h at 37° C. and 5% $CO_2$) as target cells. The effector spleen cells were tested against the mutated peptide, the wild type peptide and a control peptide (vesiculostomatitis virus nucleoprotein, VSV-NP, aa 52-59). Shown is the mean measured spot number from which the background spots against VSV-NP were subtracted for every mouse (empty circles: mice immunized with wildtype peptide; filled boxes: mice immunized with mutated peptides). Data are shown for each mouse and mean t SEM is depicted.

Figure 4:
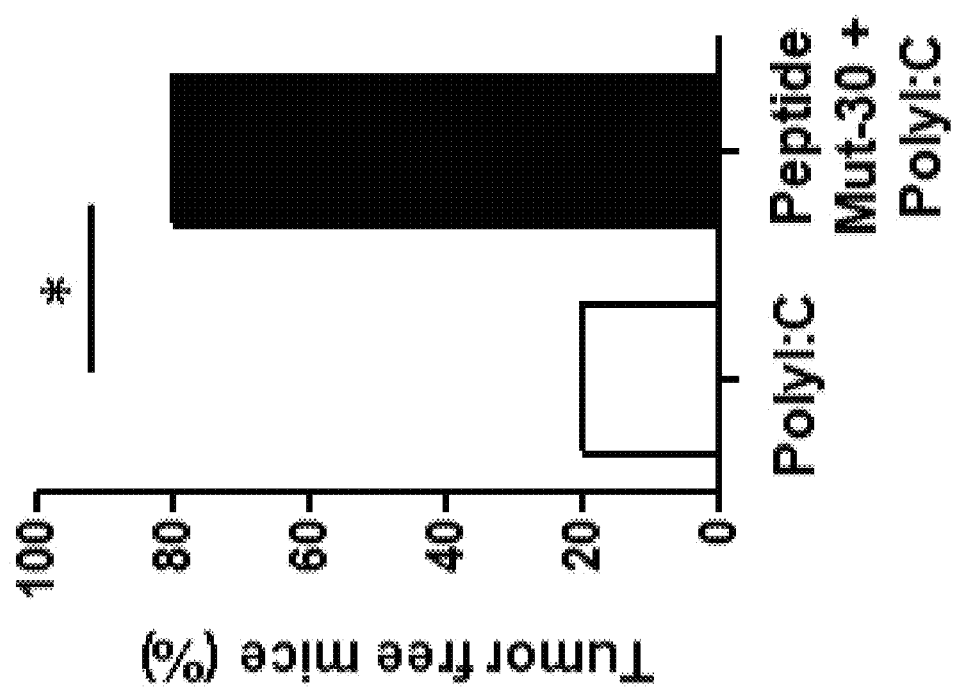

FIG. 4: Survival benefit for mice vaccinated with newly identified mutated peptide sequence B16F10 cells ($7.5 \times 10^4$) were inoculated subcutaneously on d0. Mice were vaccinated with peptide 30 (Jerini Peptide Technologies (Berlin); 100 µg peptide+50 µg PolyI:C s.c. (Invivogen)) on day −4, day +2, day +9. The control group received only Poly I:C (50 µg s.c.). Tumor growth was monitored until day +16*, p<0.05 in Log-rank (Mantel-Cox) test.

FIG. 5:

(A) Examples of enhanced protein expression (left eGFP, right Luciferase) with RNA optimized for stability and translational efficiency (B) Example of polyepitopic expansion of antigen-specific $CD8^+$ and $CD4^+$ T cells with RNA optimized for effective antigen routing (s. Reference Kreiter, Konrad, Sester et al, Cancer Immunol. Immunother. 56: 1577-1587, 2007). T (C) Example of a preclinical proof of antitumoral efficacy in B16 melanoma model using an RNA vaccine that codes for a single epitope (OVA-SIINFEKL). Survival data were obtained for mice treated with vaccine alone or vaccine in combination with adjuvant. (D) Individualized, poly-neo-epitopic vaccine design. The vaccine vehicle integrates functional elements for increased expression and optimized immunogenicity. Up to 30 mutated epitopes that are spaced by linkers can be integrated per molecule in their natural sequence context.

Figure 6:
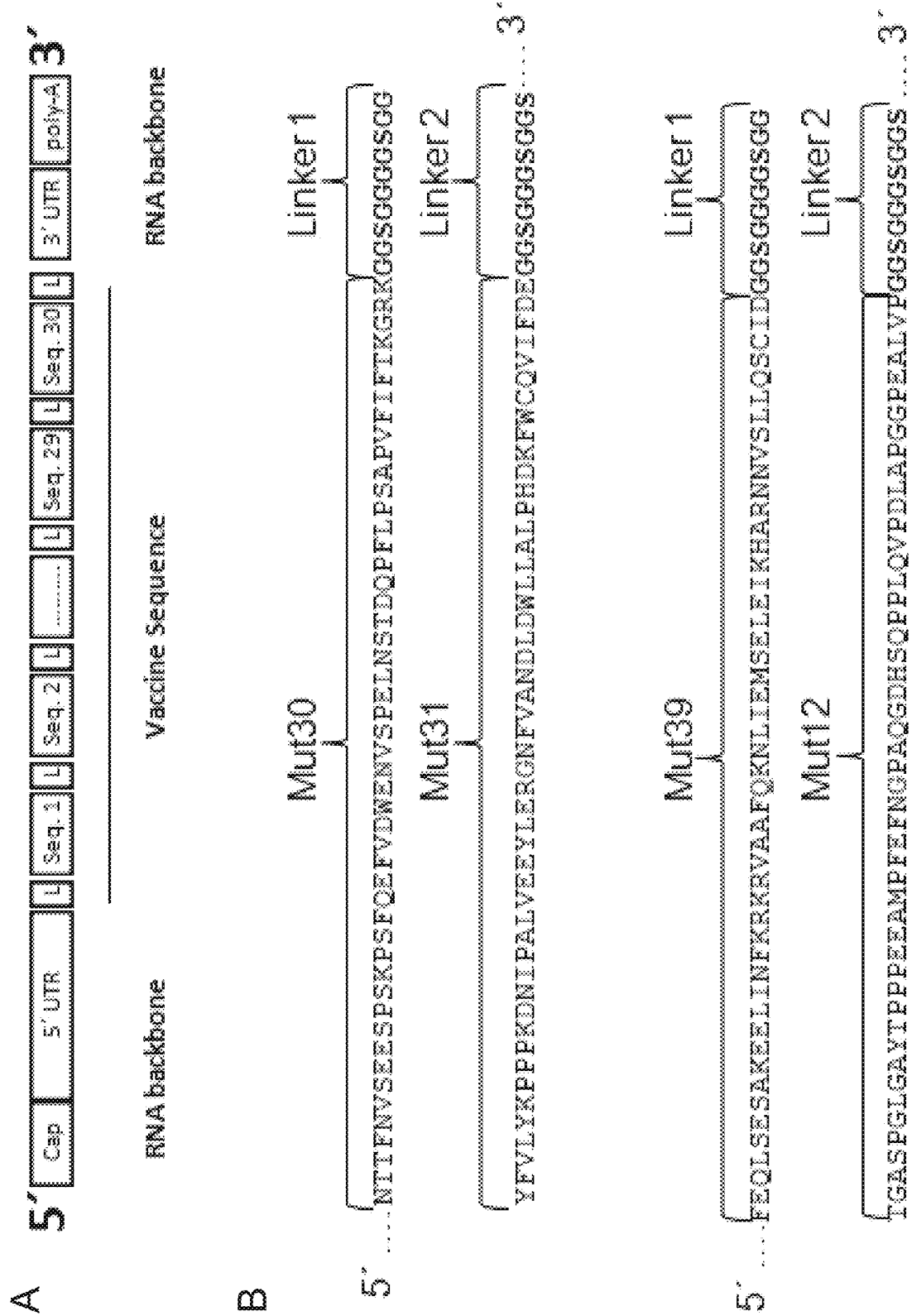

FIG. 6: Construct design (A) Schematic diagram of a RNA polyepitope construct. Cap: cap analogon; 5'UTR 5'untranslated region; L: linker; Seq. 1: RNA sequence coding for peptide containing mutated aa; 3'UTR: 3'untranslated sequence; poly-A: poly-A tail. (B) Sequence of the RNA constructs coding for 2 aa sequences including a mutated aa from B16F10. The start- and stop-codon as well as the signal peptide and the MITD sequence are not part of the schematic drawing which is symbolized by " . . . ".

Figure 7:
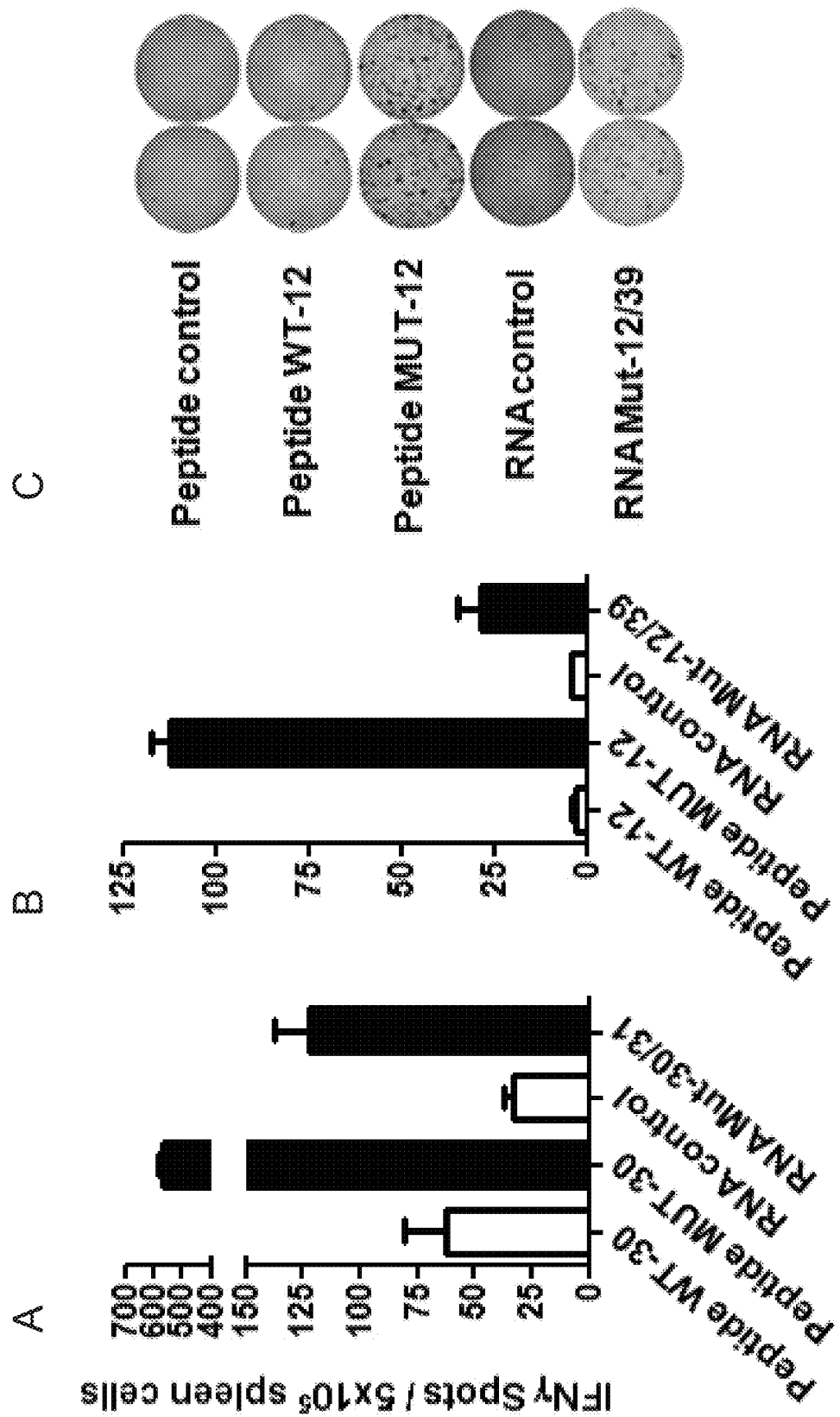

FIG. 7: Functionality of RNA Poly epitope (A-C) Data for IFNγ ELISpot using $5 \times 10^5$ spleen cells per well as effectors and $5 \times 10^4$ BMDC as target cells. The BMDC were loaded with peptide (2 µg/ml for 2 h at 37° C. and 5% $CO_2$) or transfected with RNA (20 µg) by electroporation. The control RNA was eGFP (left panel) or a RNA construct coding for 2 unrelated peptides containing mutated aa separated by a linker. Data are shown as mean±SEM. (A) Data for mutation peptide 30, wild type peptide 30 and RNA coding for mutation 30 and 31 are shown. (B) Data for mutation peptide 12, wild type peptide 12 and RNA coding for mutation 12 and 39 are shown. (C) Representative ELISpot scan from a single mouse of the read-out shown in (B) is depicted.

Figure 8:
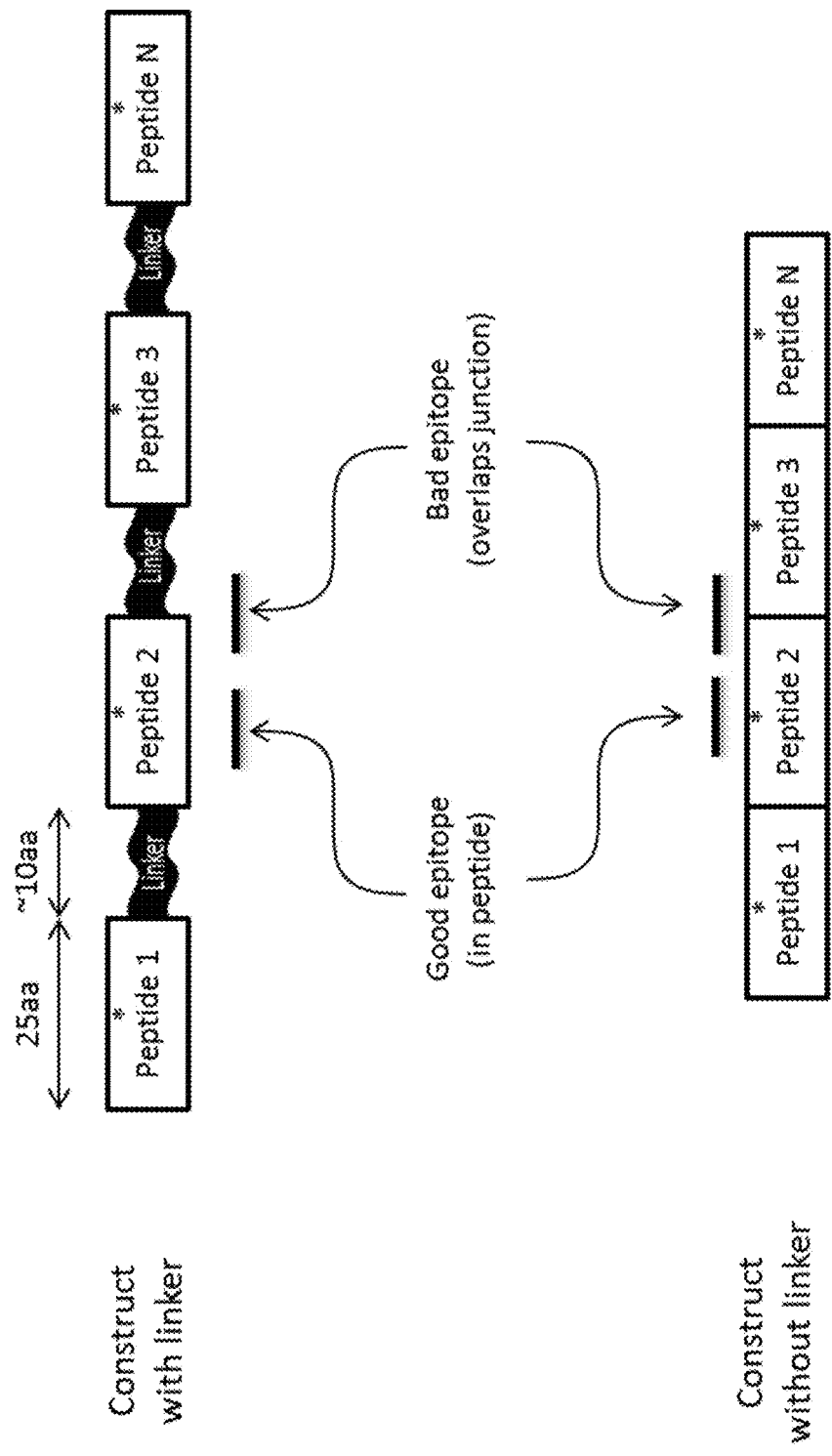

FIG. 8: Two embodiments of RNA pol-neo-epitopic vaccines showing junction epitopes The RNA vaccine can be constructed with (top) or without linkers (bottom) between mutation-encoding peptides. Good epitopes include those that include the somatic mutation ("*") and bind to MHC molecules. Bad epitopes include epitopes that bind to MHC molecules but contain either parts of two peptides (bottom) or parts of peptide and linker sequences (top).

Figure 9:
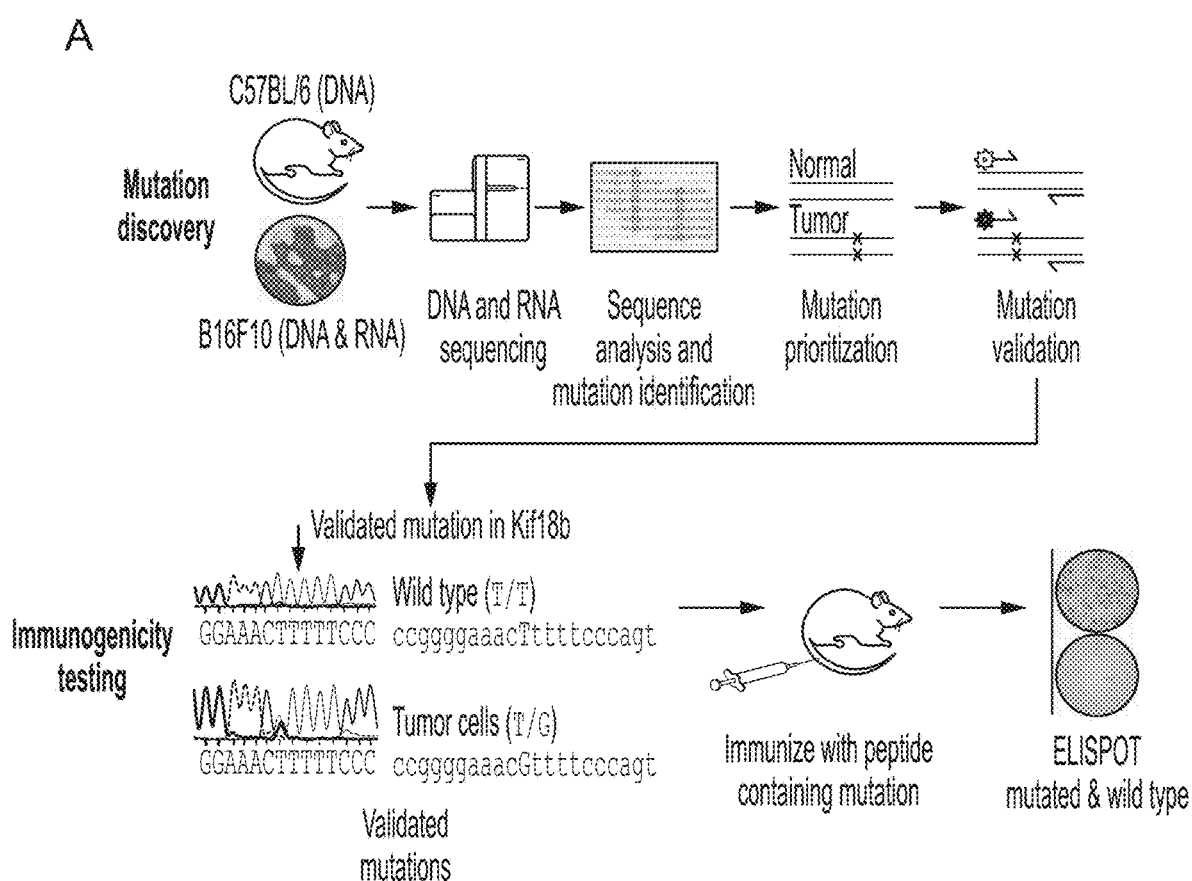
Figure 9:
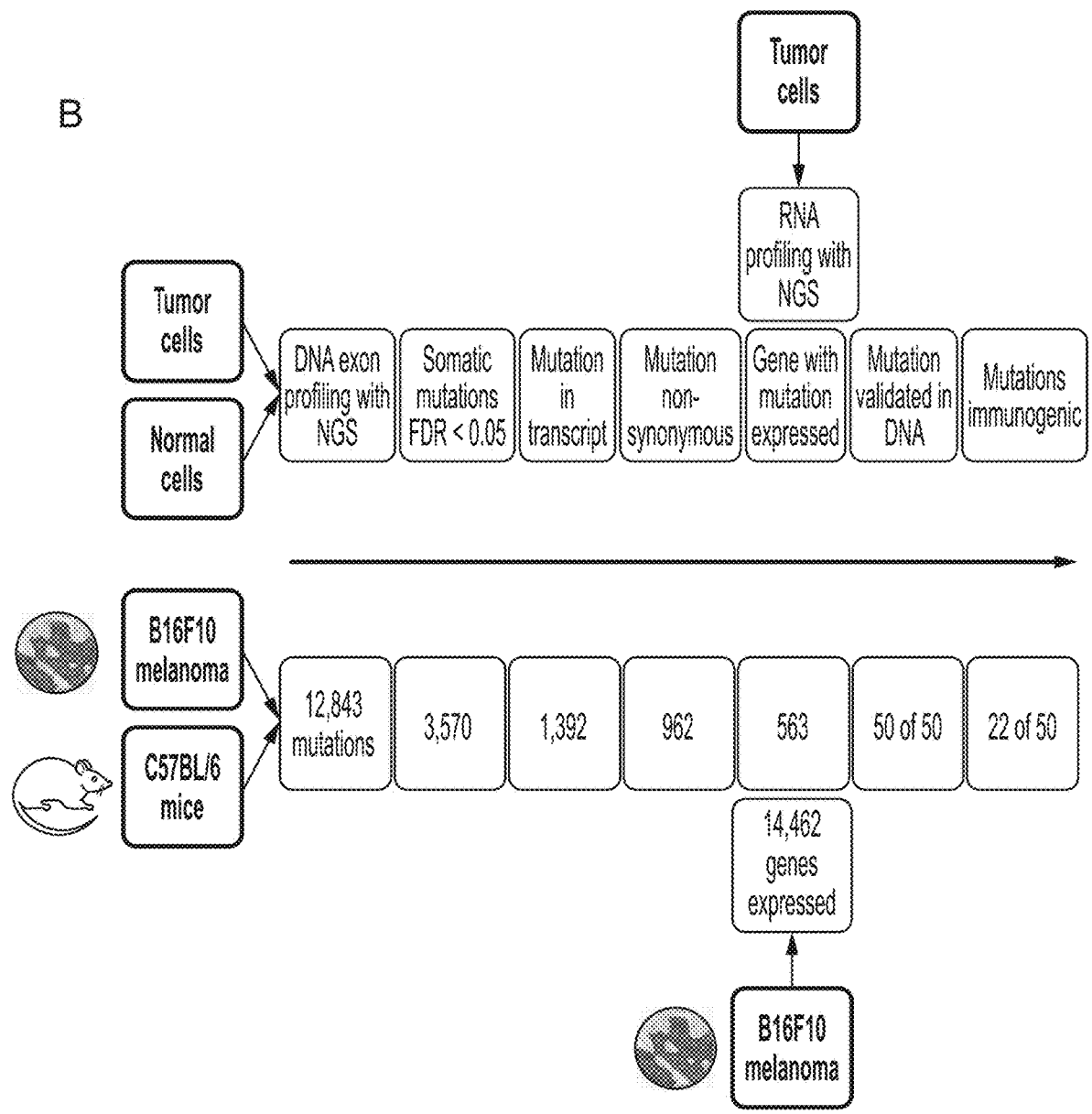
Figure 9:
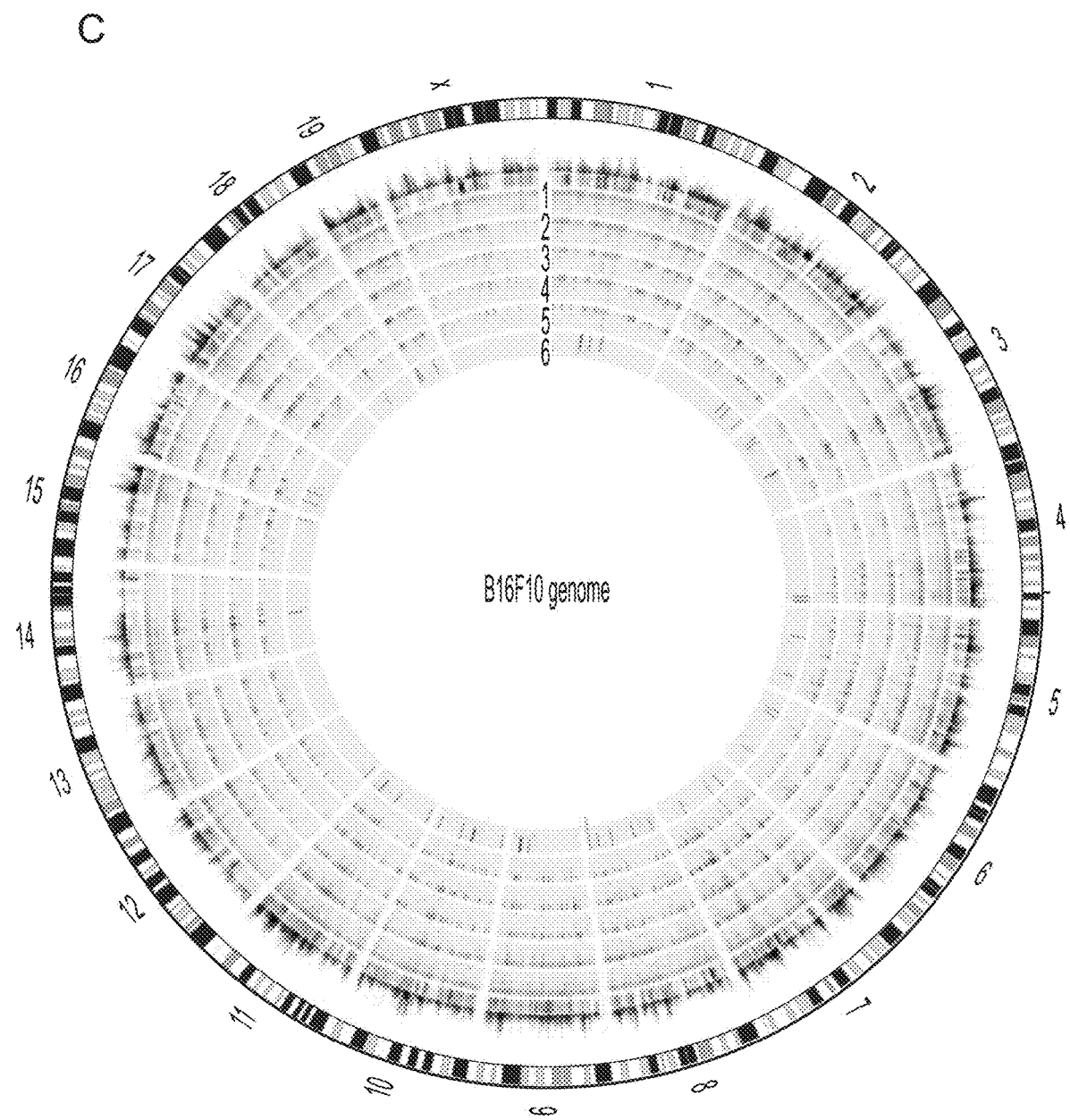

FIG. 9: Discovery and characterization of the "T-cell druggable mutanome"

(A) Flow chart gives an overview of the experimental procedure starting from B16F10 and C57BL/6 samples to ELISPOT readout. (B) The number of hits for each evaluation step and the process for selection of mutations for DNA validation and immunogenicity testing is shown. Mutations selected for validation and immunogenicity testing were those predicted to be immunogenic and in genes expressed at RPKM >10. (C) The T-cell druggable mutanome was mapped to the genome of B16F10. Rings from outside to inside stand for following subsets: (1) present in all triplicates, (2) have an FDR <0.05, (3) are located in protein coding regions, (4) cause nonsynonymous changes, (5) are localized in expressed genes, and (6) are in the validated set. Mouse chromosomes (outer circle), gene density (green), gene expression (green(low)/yellow/red(high)), and somatic mutations (orange).

FIG. 10: Immune responses elicited in vivo by vaccination of mice with mutation representing long synthetic peptides (A,B) IFN-γ ELISPOT analysis of T-cell effectors from mice vaccinated with mutation coding peptides. Columns represent means (±SEM) of 5 mice per group. Asterisks indicate statistically significant differences of reactivity against mutation and wild-type peptide (student's t-test; value p<0.05). (A) Splenocytes of vaccinated mice were restimulated with BMDCs transfected with the mutation coding peptide used for vaccination, the corresponding wild-type peptide and an irrelevant control peptide (VSV-NP). (B) For analysis of T-cell reactivity against endogenously processed mutations splenocytes of vaccinated mice were restimulated with BMDCs transfected with control RNA (eGFP) or a RNA coding for the indicted mutation. (C) Mutation 30 (gene Kif18B, protein Q6PFD6, mutation p.K739N). Sanger sequencing trace and sequence of mutation (top). Protein domains and mutation location (bottom).

Figure 11:
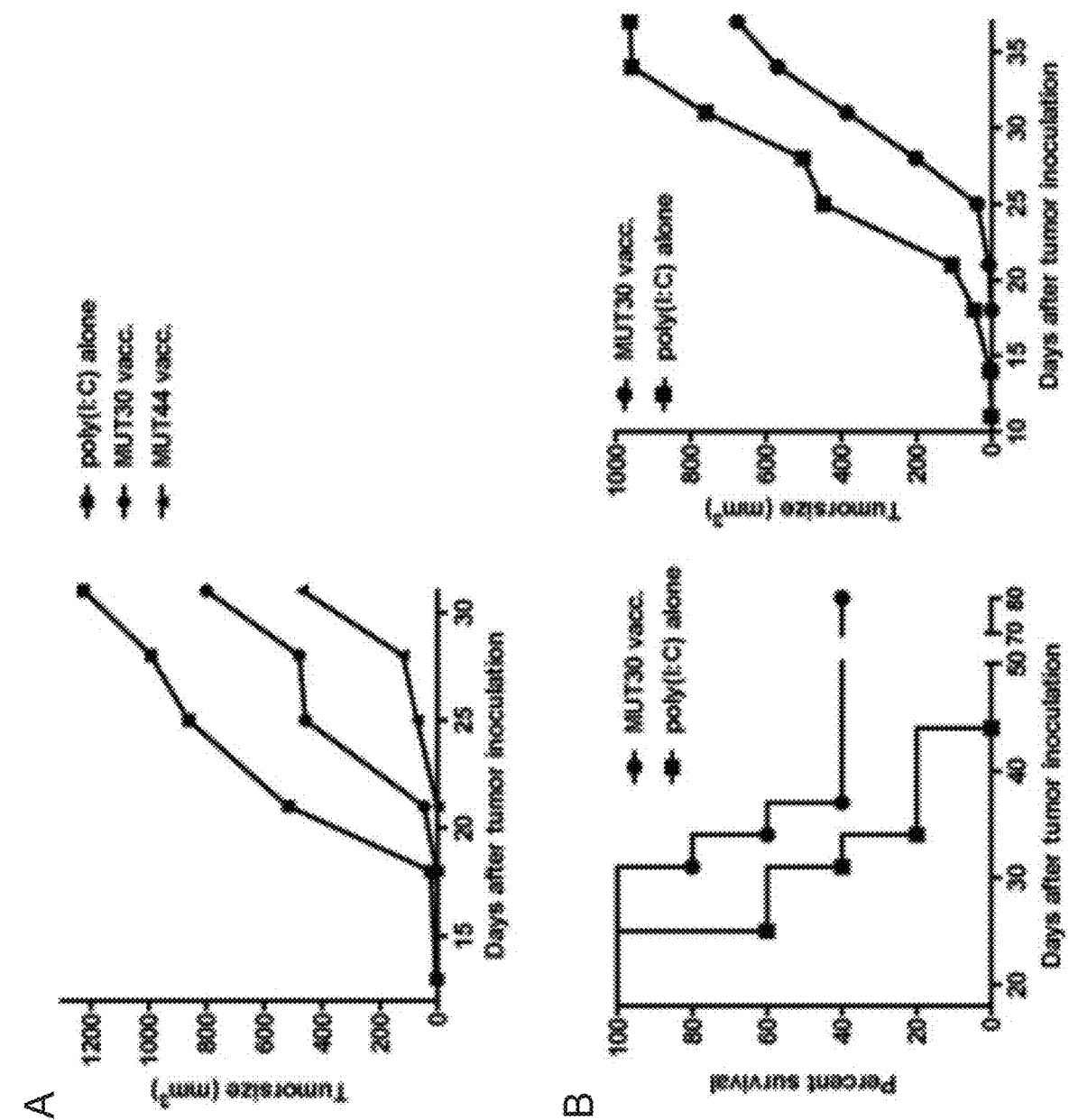

FIG. 11: Antitumoral effects of mutated peptide vaccines in mice with aggressively growing B16F10 tumors (A) C57BL/6 mice (n=7) were inoculated with $7.5 \times 10^4$ B16F10 cells s.c. into the flank of the mice. On day 3 and 10 after tumor inoculation the mice were vaccinated with 100 µg MUT30 or MUT44 peptide+50 µg poly(I:C) or with adjuvant alone. (B) C57BL/6 mice (n=5) received one immunization of 100 µg MUT30 peptide+50 µg poly(I:C) on day −4. On day 0 $7.5 \times 10^4$ B16F10 cells were inoculated s.c. into the flank of the mice. Booster immunizations with MUT30 peptide (+ poly(I:C)) were done on days 2 and 9. Kaplan-Meier survival Blot (left). Tumor growth kinetics (right).

Figure 12:
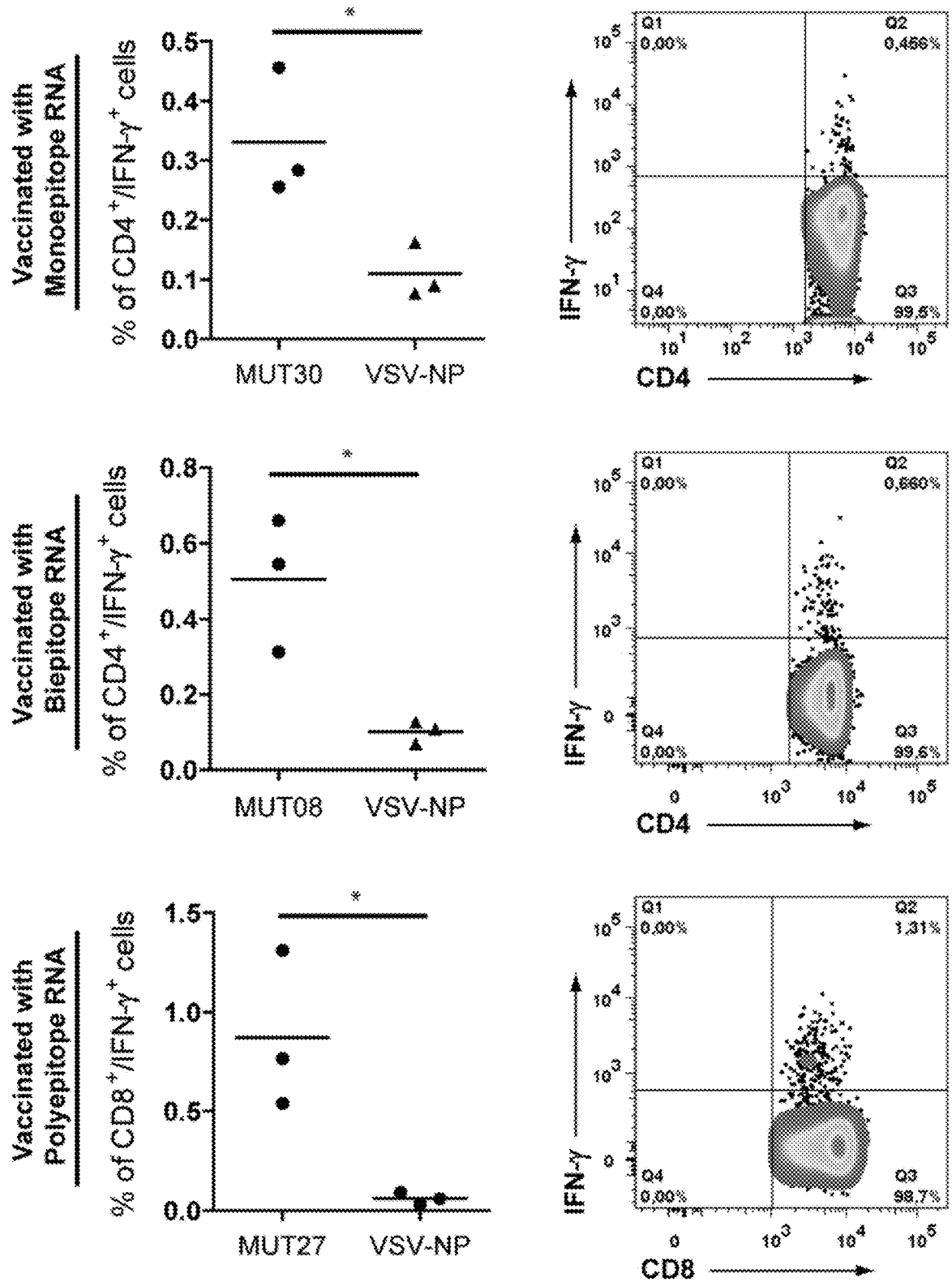

FIG. 12: Vaccination with mutation coding RNAs leads to $CD4^+$ and $CD8^+$ T-cell responses Intracellular cytokine staining analysis data for IFN-γ in $CD4^+$ and $CD8^+$ T-cell effectors from mice vaccinated with mutation coding RNAs. RNAs were coding for 1 (Monoepitope, upper row), 2 (Biepitope, middle row), or 16 (Polyepitope, lower row) different mutations. Dots represent means of 3 mice per group. Asterisks indicate statistically significant differences of reactivity against mutation and control peptide (VSV-NP) (student's t-test; value p<0.05). FACS plots show effectors from the highest IFN-γ secreting animal for each mutation and indicate phenotype of the T-cell response.

Figure 13:
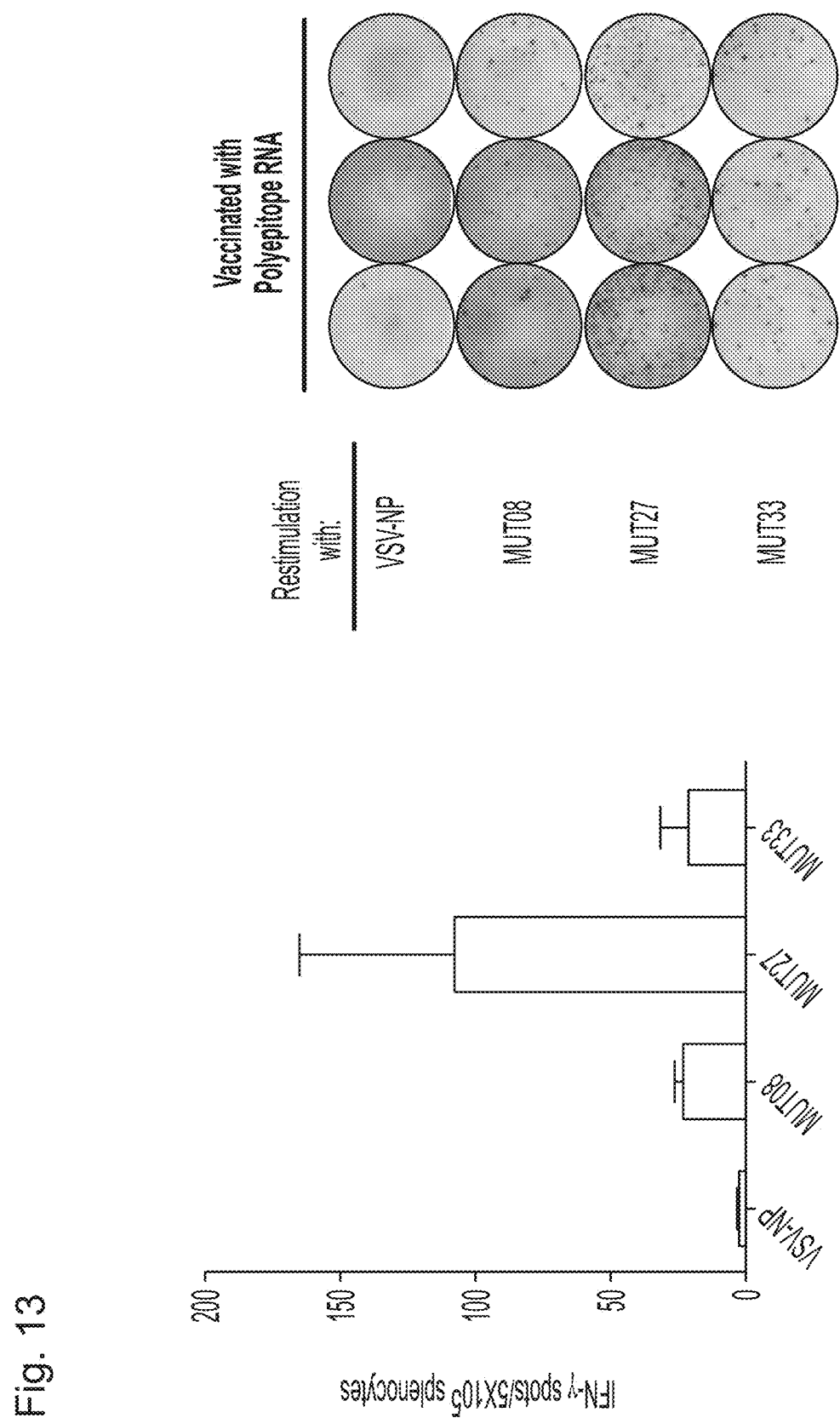

FIG. 13: Vaccination with mutation coding Polyepitope RNA leads T-cell responses against several mutations IFN-γ ELISPOT analysis of T-cell effectors from mice vaccinated with mutation coding Polyepitope including 16 different mutations. Columns represent means (ASEM) of 3 mice per group. Photograph shows triplicate wells of cells from one exemplary animal restimulated with the indicated peptides.

FIG. 14: Vaccination with 5 different model epitopes encoded by one RNA leads to immune responses against all encoded epitopes A) IFN-γ ELISPOT analysis of T-cell effectors from mice vaccinated with mutation coding model Polyepitope including 5 different model epitopes (SIINFEKL, Trp2, VSV-NP, Inf-NP, OVA class II). Splenocytes were restimulated with the indicated peptides. Spots represent means of triplicate wells from 5 mice per group. B) Pentamer staining of blood lymphocytes of one control mouse and one mouse immunized with the model Polyepitope. Inf-NP Pentamer stained $CD8^+$ cells are specific for the Inf-NP peptide.

Figure 15:
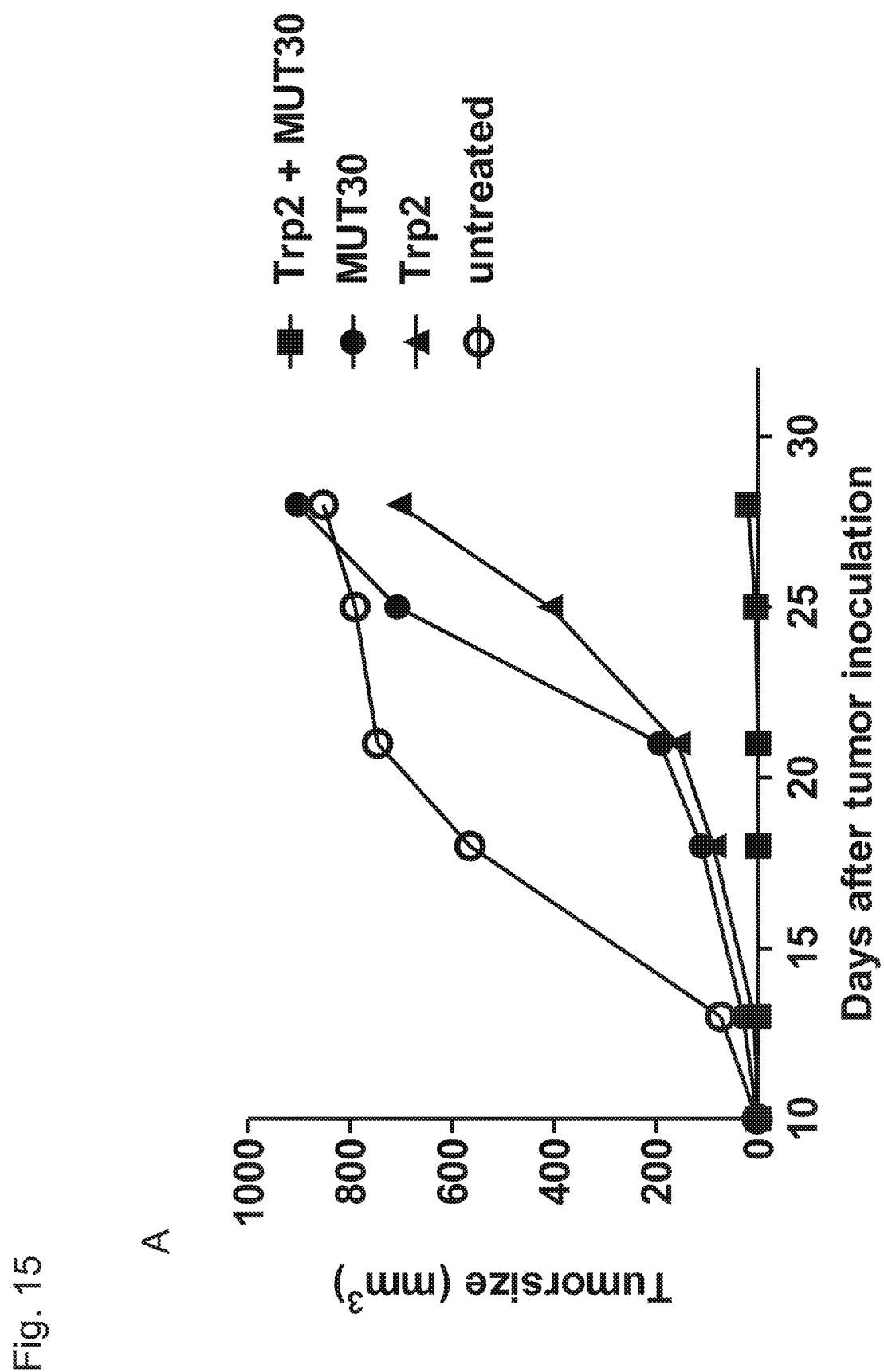
Figure 15:
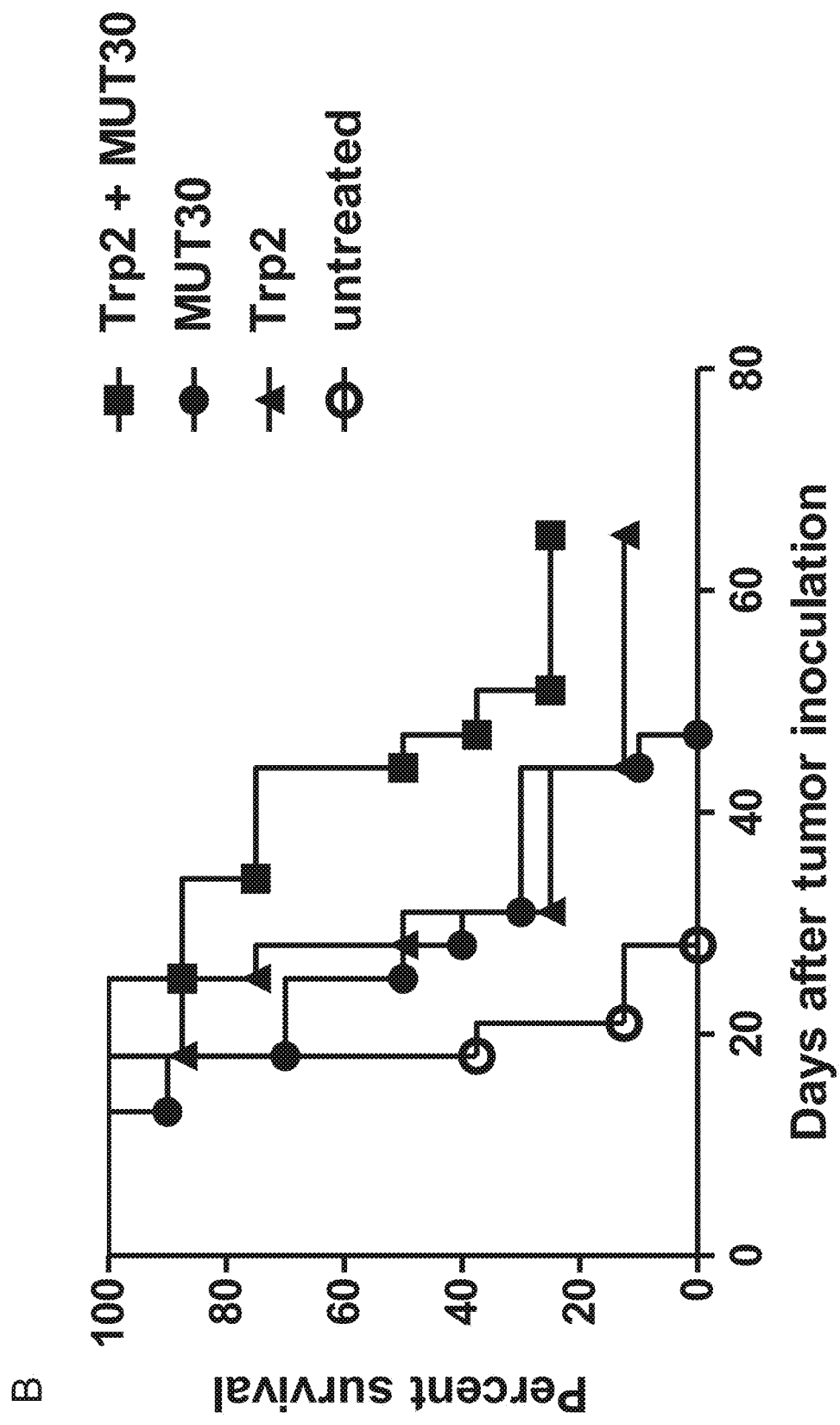

FIG. 15: A $CD4^+$ T-cell inducing mutation can induce a potent anti-tumoral effect B16F10 melanoma in synergy with a weak $CD8^+$ T-cell epitope C57BL6 mice (n=8) were inoculated with $1\times10^5$ B16F10 cells s.c. into the flank of the mice. On day 3, 10 and 17 after tumor inoculation the mice were vaccinated with 100 μg MUT30, Trp2 or both peptides+50 μg poly(I:C). A) Shown are the mean tumor growth kinetics of each group. On day 28 the mean values between the single treatment groups and the untreated animals and the combination group are statistically different (Mann-Whitney test, p-value <0.05). B) Kaplan-Meyer survival plot of the different groups. The survival curves of MUT30 and MUT30+Trp2 vaccinated mice are statistically different (Log-Rank test, p-value=0.0029).

Figure 16:
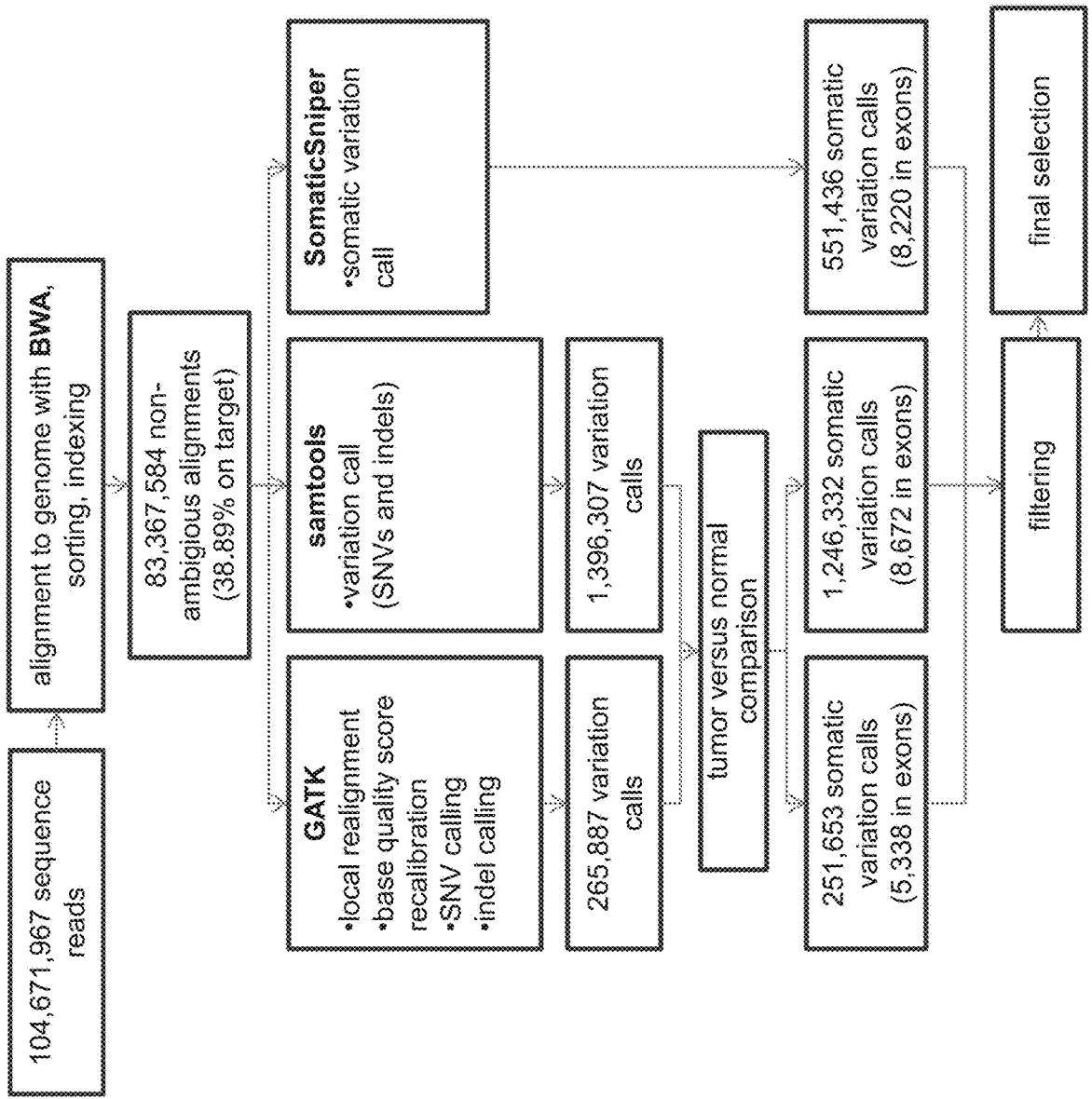

FIG. 16: Overview of process for finding somatic mutations in B16 Numbers for the individual steps are given as an example for one B16 sample, compared to one black6 sample. "Exons" refers to the exon coordinates defined by all protein coding RefSeq transcripts.

Figure 17:
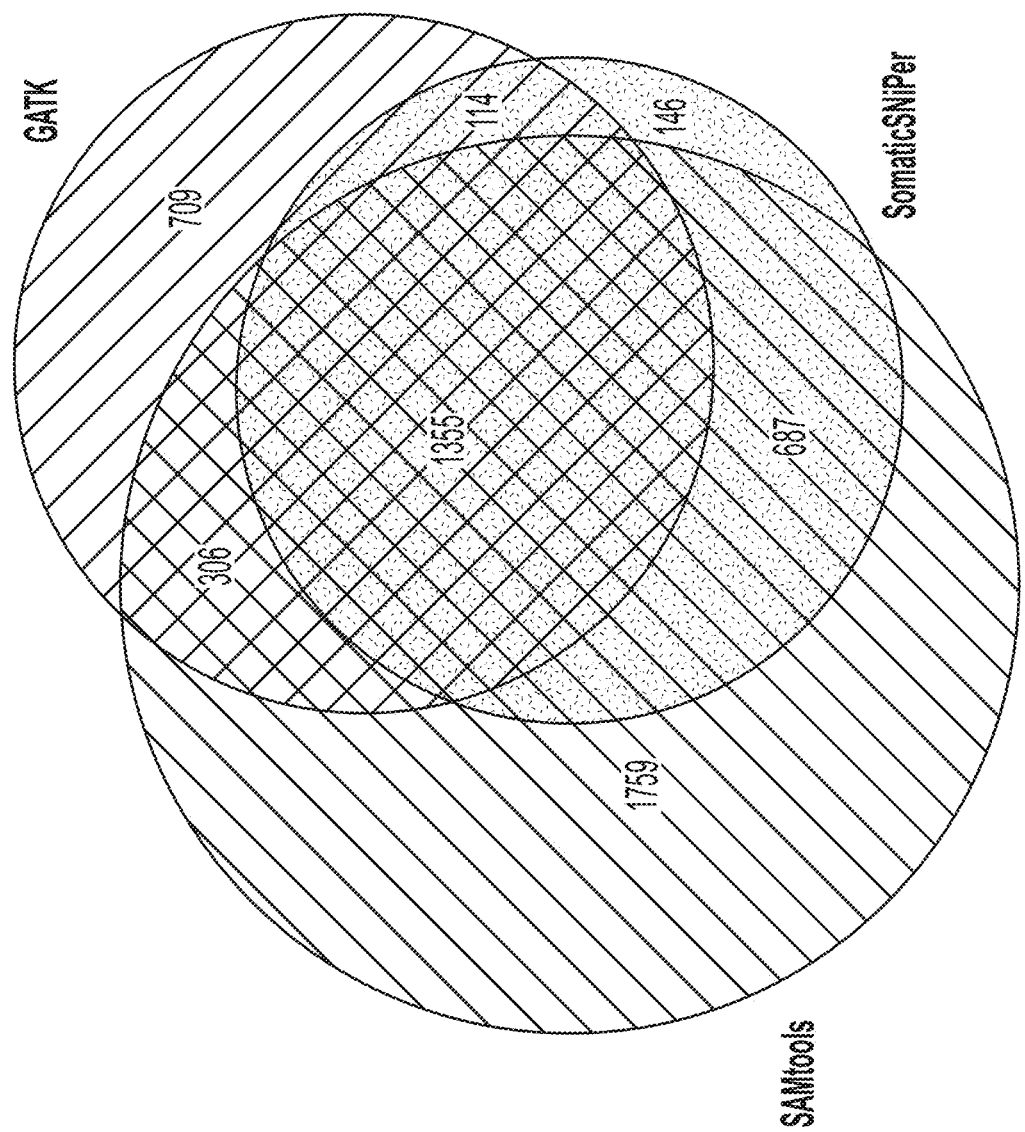

FIG. 17: Venn diagram showing the numbers of somatic variations in protein coding exons, found by the individual, two or all three software tools, respectively The numbers were calculated after filtering and represent the consensus of all three samples.

Figure 18:
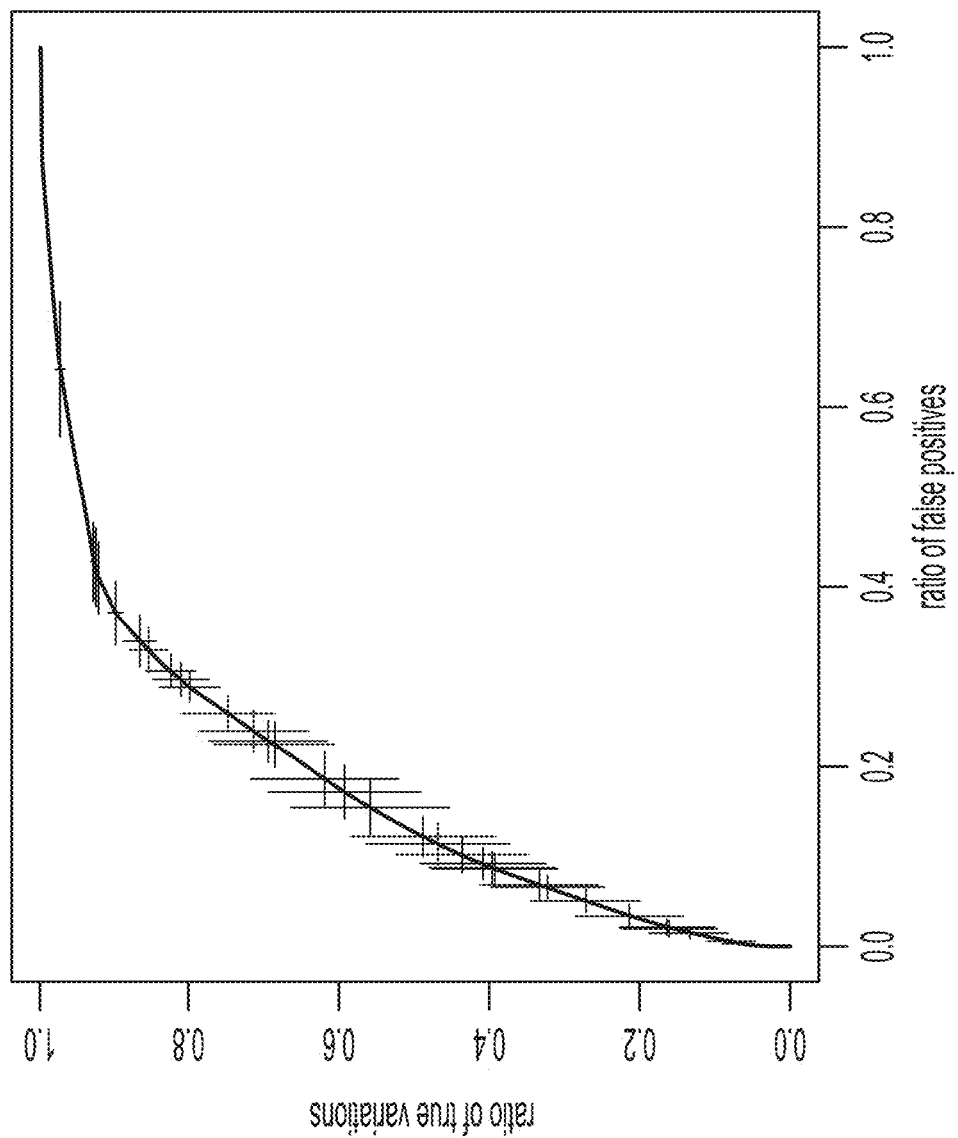

FIG. 18: A Examples of single nucleotide variations found: A somatic mutation found in all three B16 samples (left), a non-somatic mutation found in all B16 and black6 samples (middle) and a mutation found in only one black6 sample (right). B The calculated FDR distribution for the dataset of which the validated mutations were selected; the distribution is visualized as an average estimated ROC curve with the grey bars giving the 95% confidence interval for the mean in both dimensions at uniformly sampled positions. The mean was obtained from the distribution of estimated ROC curves of the FDRs for all possible 18 combinations (see text).

Figure 19:
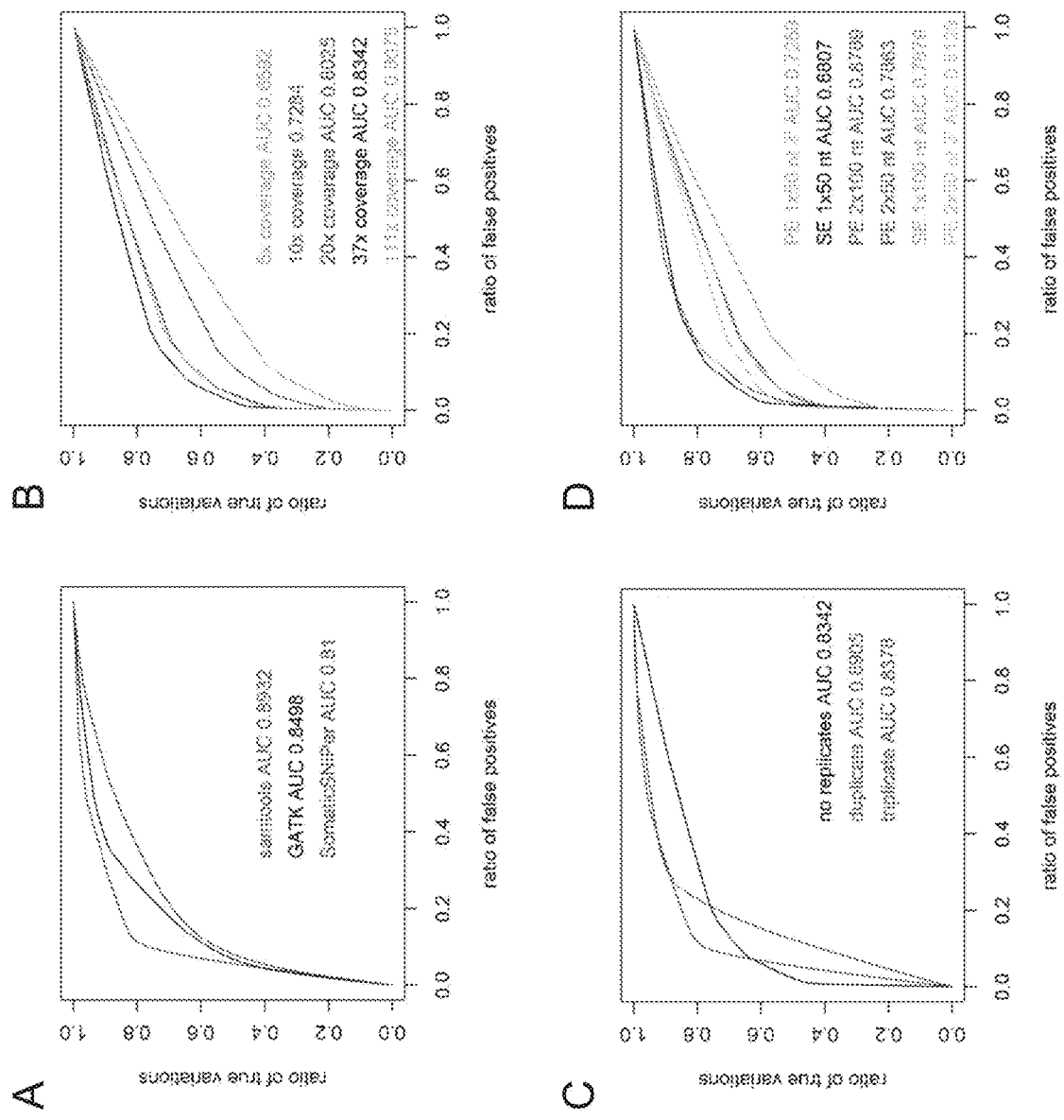

FIG. 19: A Estimated ROC curves for the comparison of the three different software tools (duplicates, 38× coverage). B Estimated ROC curves for the comparison of different average sequencing depths (samtools, no replication). 38× denotes the coverage obtained by the experiment, while other coverages were downsampled starting with this data. C Estimated ROC curves visualizing the effect of experiment replication (38× coverage, samtools). D Estimated ROC curves for different sequencing protocols (samtools, no replication). The curves were calculated using the results of the 2×100 nt library.

Figure 20:
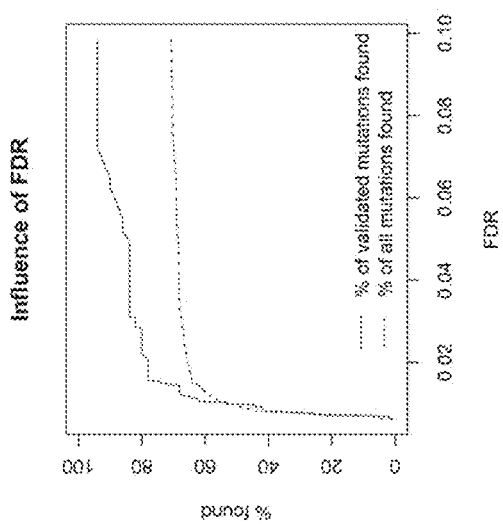

FIG. 20: A Ten validated mutations with the lowest FDRs, selected using the optimal set of parameters out of a final set of 2396 variations. None of these mutations is present in dbSNP (version 128; genome assembly mm9). B Relative amount of variations found in the same dataset as A for a given FDR cutoff, plotted separately for all variants in the dataset and the validated mutations. For visual clarity only values of 0 to 10% FDR are shown.

Figure 21:
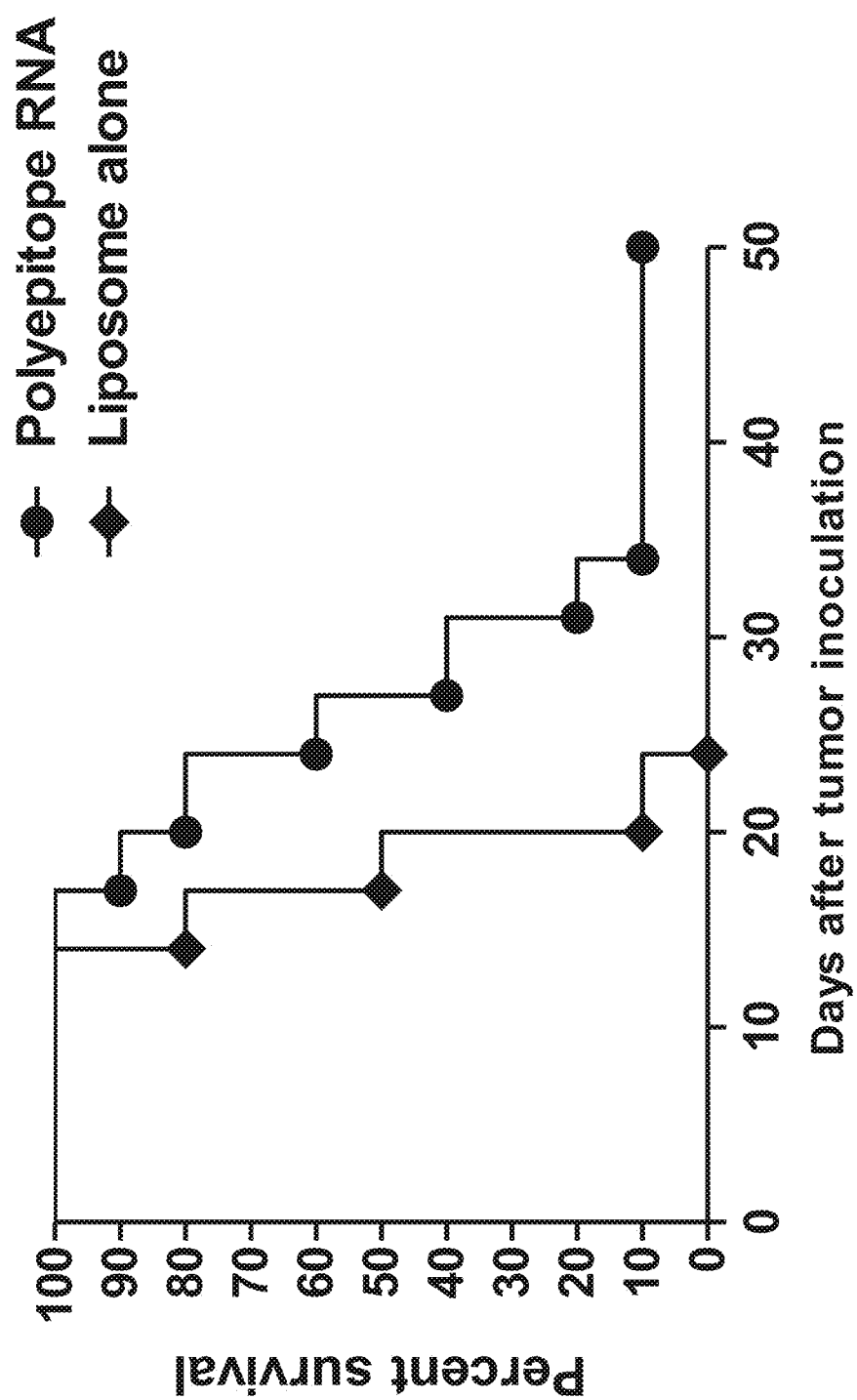

FIG. 21: Antitumoral activity of a mutation-encoding polyepitope RNA vaccine C57BL/6 mice (n=10) were inoculated with $1\times10^5$ B16F10 cells s.c. into the flank of the mice. On day 3, 6, 10, 17 and 21 after tumor inoculation the mice were vaccinated with a polytope RNA formulated a liposomal RNA transfection reagent. The control group received liposomes without RNA. The figure shows the Kaplan-Meyer survival plot of the different groups. The survival curves statistically different (Log-Rank test, p-value=0.0008).

EXAMPLES

The techniques and methods used herein are described herein or carried out in a manner known per se and as described, for example, in Sambrook et al., Molecular Cloning: A Laboratory Manual, $2^{nd}$ Edition (1989) Cold Spring Harbor Laboratory Press, Cold Spring Harbor, N.Y. All methods including the use of kits and reagents are carried out according to the manufacturers' information unless specifically indicated.

Example 1: Mutation Detection and Prioritization

We first demonstrate sequence profiling of tumor and normal samples to identify somatic mutations in an unbiased manner. We demonstrate this not only for bulk tumor samples but also, for the first time, demonstrate the ability to identify mutations from individual circulating tumor cells. Next, we prioritize the mutations for inclusion in a poly-neo-epitope vaccine based on the predicted immunogenicity of the mutation and demonstrate that the identified mutations are indeed immunogenic.

Mutation Detection

The rationale for using CTCs: the detection of circulating tumor cells (CTC) from the peripheral blood of cancer patients is a recognized independent prognostic marker for the clinical course of tumors (Pantel et al, Trends Mol Med 2010; 16(9):398-406). For many years, the clinical significance of CTCs has been the subject of intense scientific and clinical research in oncology. It has been shown that the detection of CTCs in the blood of patients with metastatic breast, prostate and colorectal cancer has prognostic relevance, providing additional information to conventional imaging techniques and other prognostic tumor biomarkers. Sequential blood samples drawn from a patient before, during an early stage, and after treatment with a therapeutic agent (systemic or targeted) provides information on treatment response/failure. The molecular analysis of drug-resistant CTCs may provide a further insight into resistance mechanisms (e.g. mutations in specific signaling pathways or loss of target expression) in individual patients. An additional possibility from the profiling and genetic characterization of CTCs is the identification of novel cancer targets for the development of new targeted therapies. This new diagnostic strategy is referred to as "Liquid Tumor Biopsy." As this profiling could be quickly and repetitively done, requiring only patient blood and no surgery, this would provide a "real time" view of the tumor state.

Mutations from tumor cells: We demonstrate our ability to identify mutations using B16 melanoma cells, exome capture to extract protein coding regions, next-generation sequencing using our HiSeq 2000, followed by bioinformatics analysis using our "iCAM" software pipeline (FIG. 1). We identify 2448 non-synonymous mutations and selected 50 for confirmation. We were able to confirm all 50 somatic mutations.

The following is an example of the protein impact of a discovered somatic mutation in B16 melanoma cells:

```
Kif18b, NM_197959, exon 3
Mutation (+15 aa)
SPSKPSFQEFVDWENVSPELNSTDQPFLPS

Wild type (+15 aa)
SPSKPSFQEFVDWEKVSPELNSTDQPFLPS
```

Mutations from individual circulating tumor cells (CTCs): Next, we were able to identify tumor-specific somatic mutations from NGS profiling of RNA from single CTCs. Labeled B16 melanoma cells were intravenously injected into mouse tails, mice were sacrificed, blood was collected from hearts, cells sorted to retrieve labeled circulating B16 cells (CTCs), RNA extracted, a SMART-based cDNA synthesis and unspecific amplification performed, followed by the NGS RNA-Seq assay and subsequence data analysis (below).

We profiled eight individual CTCs and identified somatic mutations. Furthermore, in eight of eight cells, previously identified somatic mutations were identified. In multiple cases, the data showed heterogeneity at the individual cell level. For example, at position 144078227 on chromosome 2 (assembly mm9), in gene Snx15, two cells showed the reference nucleotide (C) while two cells showed the mutated nucleotide (T).

This demonstrates that we are able to profile individual CTCs to identify somatic mutations, a fundamental path to a "real-time" iVAC (individualized vaccine), in which patients are profiled repetitively and the results reflect the current patient status rather than the status at an earlier time point. Furthermore, this demonstrates that we are able to identify heterogeneous somatic mutations that are present in a subset of tumor cells, enabling evaluation of mutation frequency, such as for identification of major mutations and rare mutations.

Methods

Samples: For the profiling experiment, samples included 5-10 mm tail samples from C57BL/6 mice ("Black6") and highly aggressive B16F10 murine melanoma cells ("B16"), which are originally derived from Black6 mice.

Circulating tumor cells (CTCs) were created using fluorescent labeled B16 melanoma cells. B16 cells were resuspended in PBS and an equal volume of freshly prepared CFSE-Solution (5 µM in PBS) was added to the cells. The sample was gentle mixed by vortex followed by incubation for 10 min at room temperature. To stop the labeling reaction, the equal amount of PBS containing 20% FSC was added to the sample and mixed gently by vortex. Following 20 min incubation at room temperature, the cells were washed twice using PBS. Finally, the cells were resuspended in PBS and injected intravenously (i.v.) in mice. After 3 minutes the mice were sacrificed and blood collected.

Erythrocytes from the blood samples were lysed by adding 1.5 ml fresh prepared PharmLyse Solution (Beckton Dickinson) per 100 µl blood. After one washing step, 7-AAD was added to the sample and incubated for 5 min at room temperature. The incubation was followed by two washing steps and the sample was resuspended in 500 µl PBS.

The CFSE labeled circulating B16 cells were sorted with an Aria I cells-sorter (BD). Single cells were sorted on 96-well-v-bottom plated prepared with 50 µl/well RLT buffer (Quiagen). After finishing the sorting the plates were stored at −80° C. until the Nucleic acid extraction and sample preparation started.

Nucleic acid extraction and sample preparation: nucleic acids from B16 cells (DNA and RNA) and Black6 tail tissue (DNA) were extracted using Qiagen DNeasy Blood and Tissue kit (DNA) and Qiagen RNeasy Micro kit (RNA).

For individual sorted CTCs, RNA was extracted and a SMART-based cDNA synthesis and unspecific amplification performed. RNA from sorted CTC cells was extracted with the RNeasy Micro Kit (Qiagen, Hilden, Germany) according to the instructions of the supplier. A modified BD SMART protocol was used for cDNA synthesis: Mint Reverse Transcriptase (Evrogen, Moscow, Russia) was combined with oligo(dT)-T-primer long for priming of the first-strand synthesis reaction and TS-short (Eurogentec S.A., Seraing, Belgium) introducing an oligo(riboG) sequence to allow for creation of an extended template by the terminal transferase activity of the reverse transcriptase and for template switch [Chenchik, A., Y. et al. 1998. *Generation and use of high quality cDNA from small amounts of total RNA by SMART PCR. In Gene Cloning and Analysis by RT-PCR.* P. L. J. Siebert, ed. *BioTechniques Books*, M A, Natick 305-319]. First strand cDNA synthesized according to the manufacturer's instructions was subjected to 35 cycles of amplification with 5 U Pfu Ultra Hotstart High-Fidelity DNA Polymerase (Stratagene, La Jolla, Calif.) and 0.48 µM primer TS-PCR primer in the presence of 200 µM dNTP (cycling conditions: 2 min at 95° C. for, 30 s at 94° C., 30 s at 65° C., 1 min at 72° C. for, final extension of 6 min at 72° C.). Successful amplification of the CTC genes was controlled with specific primers to monitor actin and GAPDH.

Next-generation sequencing, DNA sequencing: Exome capture for DNA resequencing was performed using the Agilent Sure-Select solution-based capture assay [Gnirke A et al: *Solution hybrid selection with ultra-long oligonucleotides for massively parallel targeted sequencing. Nat Biotechnol* 2009, 27:182-189], in this case designed to capture all mouse protein coding regions.

Shortly, 3 ug purified genomic DNA was fragmented to 150-200 bp's using a Covaris S2 ultrasound device. gDNA fragments were end repaired using T4 DNA polymerase, Klenow DNA polymerase and 5' phosphorylated using T4 polynucleotide kinase. Blunt ended gDNA fragments were 3' adenylated using Klenow fragment (3' to 5' exo minus). 3' single T-overhang Illumina paired end adapters were ligated to the gDNA fragments using a 10:1 molar ratio of adapter to genomic DNA insert using T4 DNA ligase. Adapter ligated gDNA fragments were enriched pre capture and flow cell specific sequences were added using Illumina PE PCR primers 1.0 and 2.0 and Herculase II polymerase (Agilent) using 4 PCR cycles.

500 ng of adapter ligated, PCR enriched gDNA fragments were hybridized to Agilent's SureSelect biotinylated mouse whole exome RNA library baits for 24 hrs at 65° C. Hybridized gDNA/RNA bait complexes where removed using streptavidin coated magnetic beads. gDNA/RNA bait complexes were washed and the RNA baits cleaved off during elution in SureSelect elution buffer leaving the captured adapter ligated, PCR enriched gDNA fragments. gDNA fragments were PCR amplified post capture using Herculase II DNA polymerase (Agilent) and SureSelect GA PCR Primers for 10 cycles.

All cleanups were done using 1.8× volume of AMPure XP magnetic beads (Agencourt) All quality controls were done using Invitrogen's Qubit HS assay and fragment size was determined using Agilent's 2100 Bioanalyzer HS DNA assay.

Exome enriched gDNA libraries were clustered on the cBot using Truseq SR cluster kit v2.5 using 7 pM and 50 bps were sequenced on the Illumina HiSeq2000 using Truseq SBS kit-HS 50 bp.

Next-generation sequencing, RNA sequencing (RNA-Seq): Barcoded mRNA-seq cDNA libraries were prepared from 5 ug of total RNA using a modified version of the Illumina mRNA-seq protocol. mRNA was isolated using Seramag Oligo(dT) magnetic beads (Thermo Scientific). Isolated mRNA was fragmented using divalent cations and heat resulting in fragments ranging from 160-220 bp. Fragmented mRNA was converted to cDNA using random primers and SuperScriptII (Invitrogen) followed by second strand synthesis using DNA polymerase I and RNaseH. cDNA was end repaired using T4 DNA polymerase, Klenow DNA polymerase and 5' phosphorylated using T4 polynucleotide kinase. Blunt ended cDNA fragments were 3' adenylated using Klenow fragment (3' to 5' exo minus). 3' single T-overhang Illumina multiplex specific adapters were ligated using a 10:1 molar ratio of adapter to cDNA insert using T4 DNA ligase.

cDNA libraries were purified and size selected at 200-220 bp using the E-Gel 2% SizeSelect gel (Invitrogen). Enrichment, adding of Illumina six base index and flow cell specific sequences was done by PCR using Phusion DNA polymerase (Finnzymes). All cleanups were done using 1.8× volume of AgencourtAMPure XP magnetic beads. All quality controls were done using Invitrogen's Qubit HS assay and fragment size was determined using Agilent's 2100 Bioanalyzer HS DNA assay.

Barcoded RNA-Seq libraries were clustered on the cBot using Truseq SR cluster kit v2.5 using 7 pM and 50 bps were sequenced on the Illumina HiSeq2000 using Truseq SBS kit-HS 50 bp.

CTCs: For the RNA-Seq profiling of CTCs, a modified version of this protocol was used in which 500-700 ng SMART amplified cDNA was used, paired end adapters were ligated and PCR enrichment was done using Illumina PE PCR primers 1.0 and 2.0.

NGS data analysis, gene expression: To determine expression values, the output sequence reads from RNA samples from the Illumina HiSeq 2000 were preprocessed according to the Illumina standard protocol. This includes filtering for low quality reads and demultiplexing. For RNA-Seq transcriptome analysis, sequence reads were aligned to the reference genomic sequence [*Mouse Genome Sequencing Consortium. Initial sequencing and comparative analysis of the mouse genome. Nature.* 420. 520-562 (2002)] using bowtie (version 0.12.5) [Langmead B. et al. *Ultrafast and memory-efficient alignment of short DNA sequences to the human genome. Genome Biol* 10:R25] using parameters "–v2-best" for genome alignments and default parameters for transcript alignments. The alignment coordinates were compared to the exon coordinates of the RefSeq transcripts [Pruitt K D. et al. *NCBI Reference Sequence (RefSeq): a curated non-redundant sequence database of genomes, transcripts and proteins. Nucleic Acids Res.* 2005 Jan. 1; 33 (Database issue):D501-4] and for each transcript the counts of overlapping alignments were recorded. Sequence reads not alignable to the genomic sequence were aligned to a database of all possible exon-exon junction sequences of the RefSeq transcripts. The counts of reads aligning to the splice junctions were aggregated with the respective transcript counts obtained in the previous step and normalized to RPKM (number of reads which map per kilobase of exon model per million mapped reads [Mortazavi, A. et al. (2008). *Mapping and quantifying mammalian transcriptomes by rna-seq. Nat Methods,* 5(7):621-628]) for each transcript. Both gene expression and exon expression values were calculated based on the normalized number of reads overlapping each gene or exon, respectively.

Mutation discovery, bulk tumor: 50 nt, single end, reads from the Illumina HiSeq 2000 were aligned using bwa (version 0.5.8c) [Li H. and Durbin R. (2009) *Fast and accurate short read alignment with Burrows-Wheeler Transform. Bioinformatics.* 25:1754-60] using default options to the reference mouse genome assembly mm9. Ambiguous reads—those reads mapping to multiple locations of the genome—were removed, the remaining alignments were sorted, indexed and converted to a binary and compressed format (BAM) and the read quality scores converted from the Illumina standard phred+64 to standard Sanger quality scores using shell scripts.

For each sequencing lane, mutations were identified using three software programs: including samtools (version 0.1.8) [Li H. *Improving SNP discovery by base alignment quality. Bioinformatics.* 2011 Apr. 15; 27(8):1157-8. Epub 2011 Feb. 13], GATK (version 1.0.4418) [McKenna A. et al. *The Genome Analysis Toolkit: a MapReduce framework for analyzing next-generation DNA sequencing data. Genome Res.* 2010 September; 20(9):1297-303. Epub 2010 Jul. 19], and SomaticSniper (http://genome.wust.edu/software/somaticsniper). For samtools, the author-recommend options and filter criteria were used, including first round filtering, maximum coverage 200. For samtools second round filtering, the minimum indel qualify score was 50, the point mutation minimum quality was 30. For GATK mutation calling, we followed the author-designed best practice guidelines presented on the GATK user manual (http://www.broadinstitute.org/gsa/wiki/index.php/The_Genome_Analysis_Toolkit). The variant score recalibration step was omitted and replaced by the hard-filtering option. For SomaticSniper mutation calling, the default options were used and only predicted mutations with a "somatic score" of 30 or more were considered further.

Mutation discovery. CTCs: As per the bulk tumor iCAM process, 50 nt, single end, reads from the Illumina HiSeq 2000 were aligned using bwa (version 0.5.8c) [5]) using default options to the reference mouse genome assembly mm9. As CTC NGS reads were derived from the RNA-Seq assay, reads were also aligned to transcriptome sequences, including exon-exon junctions, using bowtie (above). Using all alignments, the nucleotide sequences from the reads were compared to both the reference genome and the bulk-tumor derived B16 mutations. Identified mutations were evaluated both using perl scripts and manually using the software program samtools and the IGV (Integrated Genome Viewer) to image the results.

The output of "mutation discovery" is the identification of somatic mutations in tumor cells, from sample to NGS data to a list of mutations. In the B16 samples, we identified 2448 somatic mutations using exome resequencing.

Mutation Prioritization

Next, we demonstrate a possibility of a mutation prioritization pipeline for vaccine inclusion. This method, called "individual cancer mutation detection pipeline" (iCAM) identifies and prioritizes somatic mutations through a series of steps incorporating multiple cutting edge algorithms and bioinformatics methods. The output of this process is a list of somatic mutations, prioritized based on likely immunogenicity.

Somatic mutation identification: Mutations are identified using three different algorithms, for both the B16 and Black6 samples (Mutation discovery, above). The first iCAM step is to combine the output lists from each algorithm to generate a high-confidence list of somatic mutations. GATK and samtools report variants in one sample relative to a reference genome. To select high confidence mutations with few false-positives for a given sample (i.e., tumor or normal), mutations are selected that are identified in all replicates. Then, variants are selected which are present in the tumor sample but not present in the normal sample. SomaticSniper automatically reports potential somatic variations from tumor and normal data pairs. We further filtered results through the intersection of the results obtained from replicates. To remove as many false positive calls as possible, we intersected the list of mutations derived from the use of all three algorithms and all replicates. The final step for each somatic mutation is to assign a confidence value (p-value) for each mutation based on coverage depth, SNP quality, consensus quality and mapping quality.

Mutation impact: the impact of the filtered, consensus, somatic mutations is determined by a script within the iCaM mutation pipeline. First, mutations that occur in genomic regions that are not unique within the genome, such as occur for some protein paralogs and pseudogenes, are excluded from analysis as sequence reads that align to multiple locations are removed. Second, whether the mutation occurs in a transcript is determined. Third, whether the mutation occurs in a protein-coding region is determined. Fourth, the transcript sequence is translated with and without the mutation to determine if there is a change in amino acid sequence.

Mutation expression: the iCAM pipeline selects somatic mutations that are found in genes and exons that are expressed in tumor cells. Expression levels are determined through NGS RNA-Seq of tumor cells (above). The number of reads that overlap a gene and an exon indicates expression levels. These counts are normalized to RPKM (Reads Per Kilobase of exon model per Million mapped reads, [Mortazavi A. et al. *Mapping and quantifying mammalian transcriptomes by RNA-Seq. Nat Methods.* 2008 July; 5(7):621-8. Epub 2008 May 30]) and those expressed above 10 RPKM are selected.

MHC binding: to determine the likelihood that an epitope containing the mutated peptide is binds to an MHC molecule, the iCAM pipeline runs a modified version of the MHC prediction software from the Immune Epitope Database (http://www.iedb.org/). The local installation includes modifications to optimize data flow through the algorithm. For the B16 and Black6 data, the prediction was run using all available black6 MHC class I alleles and all epitopes for the respective peptide lengths. Mutations are selected which fall in an epitope ranked in the 95th percentile of the prediction score distribution of the IEDB training data (http://mhcbindingpredictions.immuneepitope.org/dataset.html), considering all MHC alleles and all potential epitopes overlapping the mutation.

Mutation selection criteria: somatic mutations are selected by the following criteria: a) have unique sequence content, b) identified by all three programs, c) high mutation confidence, d) non-synonymous protein change, e) high transcript expression, f) and favorable MHC class I binding prediction.

The output of this process is a list of somatic mutations, prioritized based on likely immunogenicity. In B16 melanoma cells, there are 2448 somatic mutations. 1247 of these mutations are found in gene transcripts. Of these, 734 cause non-synonymous protein changes. Of these, 149 are in genes expressed in the tumor cells. Of these, 102 of these expressed, non-synonymous mutations are predicted to be presented on MHC molecules. These 102 likely immunogenic mutations are then passed to mutation confirmation (below).

Mutation Confirmation

Somatic mutations from DNA exome-resequencing were confirmed by either of two methods, resequencing of the mutated region and RNA-Seq analysis.

For the confirmation of the mutations by resequencing, a genomic region containing the mutation was amplified by standard PCR from 50 ng of both the tumor DNA and the normal control DNA. The size of the amplified products was in the range of 150 to 400 nt. The specificity of the reaction was controlled by loading the PCR product on the Qiaxel device (Qiagen). PCR products were purified using the minElute PCR purification kit (Qiagen). Specific PCR products were sequenced using the standard Sanger sequencing method (Eurofins), followed by electropherogram analysis.

Mutation confirmation was also accomplished through examination of tumor RNA. Tumor gene and exon expression values were generated from RNA-Seq (NGS of RNA), which generates nucleotide sequences that were mapped to transcripts and counted. We examined sequence data itself to identify mutations in the tumor sample [Berger M F. et al. *Integrative analysis of the melanoma transcriptome. Genome Res.* 2010 April; 20(4):413-27. Epub 2010 Feb. 23], providing an independent confirmation of the DNA-derived identified somatic mutations.

TABLE 1

List of genes containing the 50 validated mutations
Genes containing the 50 identified and confirmed somatic mutations, with annotation regarding gene symbol, gene name, and predicted localization and function.

| ID | Symbol | Entrez Gene Name | Location |
| --- | --- | --- | --- |
| NM_021895 | ACTN4 | actinin, alpha 4 | Cytoplasm |
| NM_028840 | ARMC1 | armadillo repeat containing 1 | unknown |
| NM_029291 | ASCC2 | activating signal cointegrator 1 complex subunit 2 | unknown |
| NM_024184 | ASF1B | ASF1 anti-silencing function 1 homolog B (*S. cerevisiae*) | Nucleus |

TABLE 1-continued

List of genes containing the 50 validated mutations
Genes containing the 50 identified and confirmed somatic mutations, with annotation
regarding gene symbol, gene name, and predicted localization and function.

| ID | Symbol | Entrez Gene Name | Location |
| --- | --- | --- | --- |
| NM_138679 | ASH1L | ash1 (absent, small, or homeotic)-like (*Drosophila*) | Nucleus |
| NM_015804 | ATP11A | ATPase, class VI, type 11A | Plasma Membrane |
| NM_009730 | ATRN | attractin | Extracellular Space |
| NM_028020 | CPSF3L | cleavage and polyadenylation specific factor 3-like | Nucleus |
| NM_010017 | DAG1 | dystroglycan 1 (dystrophin-associated glycoprotein 1) | Plasma Membrane |
| NM_015735 | DDB1 | damage-specific DNA binding protein 1, 127 kDa | Nucleus |
| NM_001080981 | DDX23 | DEAD (Asp-Glu-Ala-Asp) box polypeptide 23 | Nucleus |
| NM_054046 | DEF8 | differentially expressed in FDCP 8 homolog (mouse) | unknown |
| NM_019965 | DNAJB12 | DnaJ (Hsp40) homolog, subfamily B, member 12 | Cytoplasm |
| NM_011262 | DPF2 | D4, zinc and double PHD fingers family 2 | Nucleus |
| NM_007907 | EEF2 | eukaryotic translation elongation factor 2 | Cytoplasm |
| NM_001081286 | FAT1 | FAT tumor suppressor homolog 1 (*Drosophila*) | Plasma Membrane |
| NM_173182 | FNDC3B | fibronectin type III domain containing 3B | unknown |
| NM_008057 | FZD7 | frizzled homolog 7 (*Drosophila*) | Plasma Membrane |
| NM_201617 | GNAS | GNAS complex locus | Plasma Membrane |
| NM_030035 | GOLGB1 | golgin B1 | Cytoplasm |
| NM_011365 | ITSN2 | intersectin 2 | Cytoplasm |
| NM_029841 | KIAA2013 | KIAA2013 | unknown |
| NM_197959 | KIF18B | kinesin family member 18B | unknown |
| NM_145479 | KLHL22 | kelch-like 22 (*Drosophila*) | unknown |
| NM_018810 | MKRN1 | makorin ring finger protein 1 | unknown |
| NM_001170785 | MTHFD1L | methylenetetrahydrofolate dehydrogenase (NADP+ dependent) 1-like | Cytoplasm |
| NM_133947 | NUMA1 | nuclear mitotic apparatus protein 1 | Nucleus |
| NM_178884 | OBSL1 | obscurin-like 1 | unknown |
| NM_008765 | ORC2 | origin recognition complex, subunit 2 | Nucleus |
| NM_023209 | PBK | PDZ binding kinase | Cytoplasm |
| NM_033594 | PCDHGA11 | protocadherin gamma subfamily A, 11 | Plasma Membrane |
| NM_025951 | PI4K2B | phosphatidylinositol 4-kinase type 2 beta | Cytoplasm |
| NM_011961 | PLOD2 | procollagen-lysine, 2-oxoglutarate 5-dioxygenase 2 | Cytoplasm |
| NM_023200 | PPP1R7 | protein phosphatase 1, regulatory (inhibitor) subunit 7 | Nucleus |
| NM_008986 | PTRF | polymerase I and transcript release factor | Nucleus |
| NM_011240 | RANBP2 | RAN binding protein 2 | Nucleus |
| NM_009438 | RPL13A | ribosomal protein L13a | Cytoplasm |
| NM_009113 | S100A13 | S100 calcium binding protein A13 | Cytoplasm |
| NM_001081203 | SBNO1 | strawberry notch homolog 1 (*Drosophila*) | unknown |
| NM_009153 | SEMA3B | sema domain, immunoglobulin domain (Ig), short basic domain, secreted, (semaphorin) 3B | Extracellular Space |
| NM_026912 | SNX15 | sorting nexin 15 | Cytoplasm |
| NM_024225 | SNX5 | sorting nexin 5 | Cytoplasm |
| NM_008188 | THUMPD3 | THUMP domain containing 3 | unknown |
| NM_133352 | TM9SF3 | transmembrane 9 superfamily member 3 | Cytoplasm |
| NM_177296 | TNPO3 | transportin 3 | Cytoplasm |
| NM_011640 | TP53 | tumor protein p53 | Nucleus |
| NM_023279 | TUBB3 | tubulin, beta 3 | Cytoplasm |
| NM_029896 | WDR82 | WD repeat domain 82 | unknown |
| NM_025830 | WWP2 | WW domain containing E3 ubiquitin protein ligase 2 | Cytoplasm |
| NM_001081056 | XPOT | exportin, tRNA (nuclear export receptor for tRNAs) | Nucleus |

Example 2: IVAC Selection Algorithm Enables the Detection of Immunogenic Mutations To investigate if specific T-cell responses could be induced against the confirmed mutations from B16F10 melanoma cells, naïve C57B/6 mice (n=5/peptide) were immunized twice (do, d7) subcutaneously with 100 pg peptide (+50 pg PolyI:C as adjuvant) comprising either the mutated or the wild type aa sequence (see Table 2). All peptides had a length of 27 aa with the mutated/wild type as at the central position. At day 12 mice were sacrificed and the spleen cells were harvested. As read-out method IFNγ ELISpot was performed using $5 \times 10^5$ spleen cells/well as effectors and $5 \times 10^4$ bone marrow dendritic cells loaded with peptides (2 pg/ml) as target cells. The effector spleen cells were tested against the mutated peptide, the wild type peptide and a control peptide (vesiculostomatitis virus nucleoprotein, VSV-NP).

With 44 sequences tested we observed that 6 of them induced a T-cell immunity directed against the mutated sequence only but not to the wild type peptide (FIG. 3).

The data prove that the identified and prioritized mutations can be utilized to induce tumor specific T-cell immunity after being utilized as peptide vaccine in antigen naïve mice.

TABLE 2

Listing of mutated sequences that induced a T-cell reactivity specific for the mutated versus the wild type peptide. The amino acid exchange is marked underlined.

| Number | RefSeq ID | Sequence Type | Peptide Sequence | T-cell reactivity (mice) |
|---|---|---|---|---|
| 12 | NM_00107750, NM_010309, NM_201618, NM_201617 | Mutated<br>Wild Type | TPPPEEAMPFEFN<u>G</u>PAQGDHSQPPLQV<br>TPPPEEAMPFEFN<u>E</u>PAQGDHSQPPLQV | 5/5<br>0/5 |
| 16 | NM_008188 | Mutated<br>Wild Type | RVTCNRAGEKHCF<u>S</u>SNEAARDFGGAIQ<br>RVTCNRAGEKHCF<u>T</u>SNEAARDFGGAIQ | 3/5<br>0/5 |
| 20 | NM_023279 | Mutated<br>Wild Type | FRRKAFLHWYTGE<u>A</u>MDEMEFTEAESNM<br>FRRKAFLHWYTGE<u>G</u>MDEMEFTEAESNM | 5/5<br>1/5 |
| 30 | NM_197959 | Mutated<br>Wild Type | PSKPSFQEFVDWE<u>N</u>VSPELNSTDQPFL<br>PSKPSFQEFVDWE<u>K</u>VSPELNSTDQPFL | 5/5<br>1/5 |
| 34 | NM_145479 | Mutated<br>Wild Type | HLTQQLDTYILKN<u>V</u>VAFSRTDKYRQLP<br>HLTQQLDTYILKN<u>F</u>VAFSRTDKYRQLP | 3/5<br>0/5 |
| 36 | NM_133352 | Mutated<br>Wild Type | CGTAFFINFIAIY<u>H</u>HASRAIPFGTMVA<br>CGTAFFINFIAIY<u>Y</u>HASRAIPFGTMVA | 5/5<br>0/5 |

Example 3: Identified Mutations can Provide Therapeutic Anti-Tumor Immunity

In order to validate whether the identified mutations have the potential to confer anti-tumor immunity after vaccination to naïve mice we investigated this question with the peptide for mutation number 30 that was shown to induce a mutation selective T-cell reactivity. B16F10 cells ($7.5 \times 10^4$) were inoculated subcutaneously on d0. Mice were vaccinated with peptide 30 (see table 1; 100 pg peptide+50 pg PolyI:C s.c.) on day −4, day +2, and day +9. The control group received only Poly I:C (50 pg s.c.). Tumor growth was monitored every other day. At day +16 we observed that only 1 out of 5 mice in the peptide vaccine group had developed a tumor whereas in the control group 4 out of 5 mice showed tumor growth.

The data prove that a peptide sequence incorporating a B16F10 specific mutation can confer anti tumor immunity that is efficiently able to destroy tumor cells (see FIG. 4). Since B16F10 is a highly aggressive tumor cell line the finding that the methodology applied to identify and prioritize mutations finally led to the selection of a mutation that by itself already is potent as a vaccine is an important proof of concept for the whole process.

Example 4: Data Supporting Polyepitopic Antigen Presentation

Figure 5:
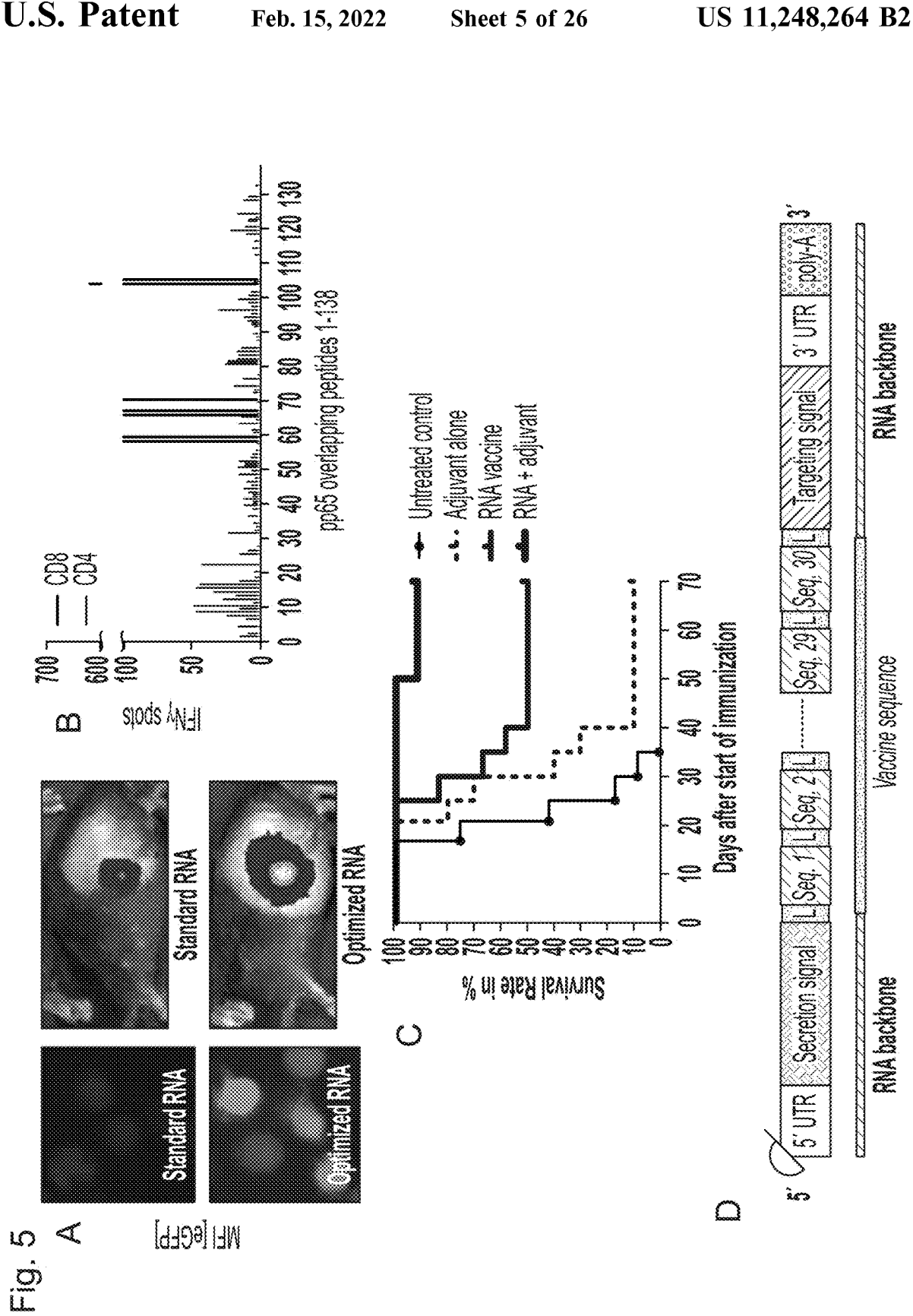

Validated mutations from protein-coding regions of a patient constitute the pool from which candidates can be selected for assembly of the poly-neo-epitope vaccine template to be used as precursor for GMP manufacturing of the RNA vaccine. Suitable vector cassettes as vaccine backbone has been already described (Holtkamp, S. et al., Blood, 108: 4009-4017, 2006; Kreiter, S. et al., Cancer Immunol. Immunother., 56: 1577-1587, 2007; Kreiter, S. et al., J. Immunol., 180: 309-318, 2008). The preferred vector cassettes are modified in their coding and untranslated regions (UTR) and ensure maximized translation of the encoded protein for extended periods (Holtkamp, S. et al., Blood, 108: 4009-4017, 2006; Kuhn, A. N. et al., Gene Ther., 17: 961-971, 2010). Furthermore, the vector backbone contains antigen routing modules for the simultaneous expansion of cytotoxic as well as helper T-cells (Kreiter, S. et al., Cancer Immunol. Immunother., 56: 1577-1587, 2007; Kreiter, S. et al., J. Immunol., 180: 309-318, 2008; Kreiter, S. et al., Cancer Research, 70 (22), 9031-9040, 2010 (FIG. 5). Importantly, we have proven that such RNA vaccine can be used to present multiple MHC class I and class II epitopes simultaneously.

The IVAC poly-neo-epitope RNA vaccine sequences are built from stretches of up to 30 amino acids that include the mutation in the center. These sequences are connected head-to-tail via short linkers to form a poly-neo-epitope vaccine coding for up to 30 or more selected mutations and their flanking regions. These patient-specific individually tailored inserts are codon-optimized and cloned into the RNA backbone described above. Quality control of such constructs includes in vitro transcription and expression in cells for validation of functional transcription and translation. Analysis of translation will be performed with antibodies against the c-terminal targeting domain.

Example 5: Scientific Proof of Concept for the RNA Poly-Neo Epitope Construct The RNA poly-neo epitope concept is based on a long in vitro transcribed mRNA which consists of sequentially arranged sequences coding for the mutated peptides connected by linker sequences (see FIG. 6). The coding sequences are chosen from the non synonymous mutations and are always built up of the codon for the mutated amino acid flanked by regions of 30 to 75 base-pairs from the original sequence context. The linker sequence codes for amino acids that are preferentially not processed by the cellular antigen processing machinery. In vitro transcription constructs are based on the pST1-A120 vector containing a T7 promotor, a tandem beta-globin 3' UTR sequence and a 120-bp poly(A) tail, which have been shown to increase the stability and translational efficiency of the RNA thereby enhancing the T-cell stimulatory capacity of the encoded antigen (Holtkamp S. et al., Blood 2006; PMID: 16940422). In addition, an MHC class I signal peptide fragment and the transmembrane and cytosolic domains including the stop-codon (MHC class I trafficking signal or MITD) flanking a poly-linker sequence for cloning the epitopes were inserted (Kreiter S. et al., J. Immunol., 180: 309-318, 2008). The latter have been shown to increase the antigen presentation, thereby enhancing the expansion of antigen-specific CD8+ and CD4+ T cells and improving effector functions.

For a first proof of concept, biepitopic vectors were used, i.e. encoding one polypeptide containing two mutated epitopes. Codon optimized sequences coding for (i) a mutated epitope of 20 to 50 amino acids, (ii) a glycine/serine-rich linker, (iii) a second mutated epitope of 20 to 50 amino acids, and (iv) an additional glycine/serine-rich linker—flanked by suitable recognition sites for restriction endonucleases to be cloned into the pST1-based construct as described above—were designed and synthesized by a commercial provider (Geneart, Regensburg, Germany). After verification of the sequence, these were cloned into the pST1-based vector backbone to obtain constructs as depicted in FIG. 6.

The pST1-A120-based plasmids as described above were linearized with a class IIs restriction endonuclease. The linearized plasmid DNAs were purified by phenol chloroform extraction and ethanol precipitation. Linearized vector DNAs were quantified spectrophotometrically and subjected to in vitro transcription essentially as described by Pokrovskaya and Gurevich (1994, Anal. Biochem. 220: 420-423). A cap analog has been added to the transcription reaction to obtain RNAs with the correspondingly modified 5'-cap structures. In the reactions, GTP was present at 1.5 mM, while the cap-analog was present at 6.0 mM. All other NTPs were present at 7.5 mM. At the end of the transcription reaction, linearized vector DNA was digested with 0.1 U/μl TURBO DNase (Ambion, Austin/TX, USA) for 15 minutes at 37° C. RNAs were purified from these reactions using the MEGAclear Kit (Ambion, Austin/TX, USA) as per manufacturer's protocol. RNA concentration and quality were assessed by spectrophotometry and analysis on a 2100 Bioanalyzer (Agilent, Santa Clara, Calif., USA).

In order to proof that a sequence incorporating a mutated amino acid and being 5'- as well as 3'-flanked by the linker sequence can be processed, presented and recognized by antigen specific T-cells we used T-cells from peptide vaccinated mice as effector cells. In an IFNγ ELISpot we tested whether the T-cells induced by peptide vaccination as described above are capable of recognizing the target cells (bone marrow dendritic cells, BMDC) either pulsed with peptide (2 pg/ml for 2 h at 37° C. and 5% $CO_2$) or transfected with RNA (20 μg produced as described above) by electroporation. As exemplified in FIG. 7 for mutation 12 and 30 (see table 2) we could observe that the RNA construct is able to give rise to the epitope recognized by mutation specific T-cells.

With the data provided we could demonstrate that an RNA encoded poly-neo epitope including glycine/serine rich linker can be translated and processed in antigen presenting cells leading to presentation of the correct epitope that is recognized by the antigen specific T-cells.

Example 6: Poly-Neo-Epitope Vaccine Design—the Relevance of the Linker

The poly-neo-epitope RNA construct contains a backbone construct into which multiple somatic mutation-encoding peptides connected with a linker peptide sequence are placed. In addition to codon optimization and increased RNA stability and translational efficiency due to the backbone, one embodiment of the RNA poly-neo-epitope vaccine contains linkers designed to increase MHC Class I and II presentation of antigenic peptides and decrease presentation of deleterious epitopes.

Linker: the linker sequence was designed to connect multiple mutation-containing peptides. The linker should enable creation and presentation of the mutation epitope while hinder creation of deleterious epitopes, such as those created at the junction suture between adjacent peptides or between linker sequence and endogenous peptides. These "junction" epitopes may not only compete with the intended epitopes to be presented on the cell surface, decreasing vaccine efficacy, but could generate an unwanted autoimmune reaction. Thus, we designed the linker sequence to a) avoid creating "junction" peptides that bind to MHC molecules, b) avoid proteasomal processing to create "junction" peptides, c) be efficiently translated and processed by the proteasome.

To avoid creation of "junction" peptides that bind MHC molecules, we compared different linker sequences. Glycine, for example, inhibits strong binding in MHC binding groove positions [Abastado J P. et al., J Immunol. 1993 Oct. 1; 151(7): 3569-75]. We examined multiple linker sequences and multiple linker lengths and calculated the number of "junction" peptides that bind MHC molecules. We used software tools from the Immune Epitope Database (IEDB, http://www.immuneepitoe.org) to calculate the likelihood that a given peptide sequence contains a ligand that will bind MHC Class I molecules.

In the B16 model, we identified 102 expressed, non-synonymous somatic mutations predicted to be presented on MHC Class I molecules. Using the 50 confirmed mutations, we computationally designed different vaccine constructs, including either the use of no linkers or the use of different linker sequences, and computed the number of deleterious "junction" peptides using the IEDB algorithm (FIG. 8).

Table 5 shows the results of several different linkers, different linker lengths, and the use of no linker and five linkers. The number of MHC-binding junction peptides ranges from 2 to 91 for the 9 aa and 10 aa epitope predictions (top and middle). The size of the linker influences the number of junction peptides (bottom). For this sequence, the fewest 9 aa epitopes are predicted for the 7 aa linker sequence GGSGGGG.

The Linker 1 and Linker 2 used in the RNA poly-neo epitope vaccine constructs tested experimentally (see below) also had a favorably low number of predicted junctional neoepitopes. This holds true for predictions of 9-mers and 10-mers.

This demonstrates that the sequence of the linker is critically important for the creation of bad MHC binding epitopes. Furthermore, the length of the linker sequence impacts the number of bad MHC binding epitopes. We find that sequences that are G-rich hinder the creation of MHC-binding ligands.

TABLE 3

Impact of Linker (10 aa epitopes). The predicted number of bad epitopes defined as MHC Class I binding epitopes that contain junction sequences, for each peptide linker. Here, 10 amino acid epitopes are considered. Glycine-rich linkers have the fewest junction epitopes.

| Linker | # bad epitopes (10 aa) |
| --- | --- |
| none | 14 |
| TSLNALLNAH | 54 |
| SIINFEKL | 65 |
| SSSSSSSSSS | 85 |
| GGGGGGGGGG | 6 |
| GGSGGGGSGG (Linker 1) | 8 |
| GGSGGGSGGG (Linker 2) | 9 |

TABLE 4

Impact of Linker Part (9 aa epitopes). The predicted number of bad epitopes, defined as MHC Class I binding epitopes that contain junction sequences, for each peptide linker. Here, 9 amino acid epitopes are considered. Glycine-rich linkers have the fewest junction epitopes.

| Linker | # bad epitopes (9 aa) |
| --- | --- |
| none | 17 |
| TSLNALLNAH | 83 |
| SIINFEKL | 64 |
| SSSSSSSSSS | 33 |
| GGGGGGGGGG | 2 |
| GGSGGGGSGG (Linker 1) | 4 |
| GGSGGGSGGG (Linker 2) | 3 |

TABLE 5

Impact of Linker Part. The predicted number of bad epitopes, defined as MHC Class I binding epitopes that contain junction sequences, for each peptide linker. Here, 9 amino acid epitopes are considered. Top: the number of 9 aa junction epitopes for no linker and 5 diverse linkers. Middle: the number of 10 aa junction epitopes for no linker and 5 diverse linkers. Lower: the number of 99 aa junction epitopes for similar linkers of different lengths. Glycine-rich linkers have the fewest junction epitopes.

| Linker sequence | # junction epitopes (9 aa) |
| --- | --- |
| none | 17 |
| TSLNALLNA | 91 |
| SIINFEKL | 64 |
| SSSSSSSS | 33 |
| GGGGGGGG | 2 |
| GGSGGGGSG | 4 |
| Linker sequence | # junction epitopes (10 aa) |
| none | 14 |
| TSLNALLNA | 63 |
| SIINFEKL | 65 |
| SSSSSSSS | 85 |
| GGGGGGGGG | 6 |
| GGSGGGSGG | 9 |
| Linker sequence | # junction epitopes (9 aa) |
| GGSGG | 5 |
| GGSGGG | 4 |
| GGSGGGG | 2 |
| GGSGGGGS | 7 |
| GGSGGGGSG | 4 |
| GGSGGGGSGG | 4 |

To avoid proteasomal processing that may create "junction" peptides, we explored usage of different amino acids in the linker. Glycine rich sequences impair proteasomal processing [Hoyt M A et al. (2006). EMBO J 25 (8): 1720-9; Zhang M. and Coffino P. (2004) J Biol Chem 279 (10): 8635-41]. Thus glycine rich linker sequences act to minimize the number of linker-containing peptides that can be processed by the proteasome.

The linker should allow the mutation-containing peptides to be efficiently translated and processed by the proteasome. Amino acids glycine and serine are flexible [Schlessinger A and Rost B., Proteins. 2005 Oct. 1; 61(1):115-26]; including them in a linker results in a more flexible protein. We incorporate glycine and serine into the linker to increase protein flexibility which should allow more efficient translation and processing by the proteasome, in turn enabling better access to the encoded antigenic peptides.

Thus, the linker should be glycine rich to hinder the creation of MHC binding bad epitopes; should hinder the ability of the proteasome to process linker peptides, which can be accomplished through inclusion of glycine; and should be flexible to increase access to mutation containing peptides, which can be accomplished through the combination of glycine and serine amino acids. Therefore, in one embodiment of the vaccine construct of the invention, the sequences GGSGGGGSGG and GGSGGGSGGS are preferably included as linker sequences.

Example 7: RNA Poly-Neo Epitope Vaccine

The RNA poly-neo epitope vaccine constructs are based on the pST1-A120 vector containing a T7 promotor, a tandem beta-globin 3' UTR sequence and a 120-bp poly(A) tail, which have been shown to increase the stability and translational efficiency of the RNA thereby enhancing the T-cell stimulatory capacity of the encoded antigen ((Holtkamp S. et al., Blood 2006; PMID: 16940422). In addition, an MHC class I signal peptide fragment and the transmembrane and cytosolic domains including the stop-codon (MHC class I trafficking signal or MITD) flanking a poly-linker sequence for cloning the epitopes were inserted (Kreiter S. et al., J. Immunol., 180: 309-318, 2008). The latter have been shown to increase the antigen presentation, thereby enhancing the expansion of antigen-specific CD8+ and CD4+ T cells and improving effector functions.

To provide RNA poly-neo epitope constructs for the 50 identified and validated mutations of B16F10 3 RNA constructs were generated. The construct consists of codon optimized sequences coding for (i) a mutated epitope of 25 amino acids, (ii) a glycine/serine-rich linker, (iii) repetitions of mutated epitope sequence followed by a glycin/serine-rich linker. The chain of mutated epitope containing sequences and linkers is flanked by suitable recognition sites for restriction endonucleases to be cloned into the pST1-based construct as described above. The vaccine constructs were designed and synthesized by GENEART. After verification of the sequence, these were cloned into the pST1-based vector backbone to obtain the RNA poly-neo epitope vaccine constructs.

Description of the Clinical Approach
The Clinical Application will cover following steps:
Eligible patients must consent to DNA analysis by next generation sequencing.
Tumor specimen obtained from routine diagnostic procedures (paraffin embedded formalin fixed tissue) and peripheral blood cells will be obtained and used for mutation analysis as described.
Discovered mutations will be confirmed
Based on Prioritization vaccine will be designed. For RNA vaccines a master plasmid template will be generated by gene synthesis and cloning
Plasmids will be used for clinical grade RNA production, quality control and release of the RNA vaccine.
The vaccine drug product will be sent to the respective trial center for clinical application.
The RNA vaccine can be used as a naked vaccine in formulation buffer or encapsulated into nanoparticles or liposomes for direct injection into e.g. lymph nodes, s.c., i.v., i.m. Alternatively, the RNA vaccine can be used for in vitro transfection e.g of dendritic cells for adoptive transfer.

The whole clinical process takes less than 6 weeks. The "lag phase" between patient informed consent and availability of the drug will be carefully addressed by the clinical trial protocol, including allowing the standard treatment regimen to be continued until the investigational drug product is available.

Example 8: Identification of Tumor Mutations and Exploiting them for Tumor Vaccination We applied NGS exome resequencing for mutation discovery in the B16F10 murine melanoma cell line and identified 962 non-synonymous somatic point mutations, 563 in expressed genes. Potential driver mutations occur in classical tumor suppressor genes (Pten, Trp53, Tp63, Pml) and genes involved in proto-oncogenic signaling pathways that control cell proliferation (e.g. Mdm1, Pdgfra), cell adhesion and migration (e.g. Fdz7, Fat1) or apoptosis (Casp9). Moreover, B16F10 harbors mutations in Aim1 and Trrap that were previously described to be frequently altered in human melanoma.

The immunogenicity and specificity of 50 validated mutations were assayed using C57BL/6 mice immunized with long peptides encoding the mutated epitopes. One third (16/50) of them were shown to be immunogenic. Of these, 60% elicited immune responses preferentially directed against the mutated sequence as compared to the wild type sequence.

We tested the hypothesis in tumor transplant models. Immunization with peptides conferred in vivo tumor control in protective and therapeutic settings, qualifying mutated epitopes containing single amino acid substitutions as effective vaccines.

Animals
C57BL/6 mice (Jackson Laboratories) were kept in accordance with federal and state policies on animal research at the University of Mainz.

Cells
B16F10 melanoma cell line was purchased in 2010 from the American Type Culture Collection (Product: ATCC CRL-6475, Lot Number: 58078645). Early (3rd, 4th) passages of cells were used for tumor experiments. Cells were routinely tested for *Mycoplasma*. Re-authentification of cells has not been performed since receipt.

Next-Generation Sequencing
Nucleic acid extraction and sample preparation: DNA and RNA from bulk B16F10 cells and DNA from C57B/6 tail tissue were extracted in triplicate using Qiagen DNeasy Blood and Tissue kit (for DNA) and Qiagen RNeasy Micro kit (for RNA).

DNA exome sequencing: Exome capture for DNA resequencing was performed in triplicate using the Agilent Sure-Select mouse solution-based capture assay (Gnirke A et al., Nat Biotechnol 2009; 27:182-9), designed to capture all mouse protein coding regions. 3 pg purified genomic DNA (gDNA) was fragmented to 150-200 bp using a Covaris S2 ultrasound device. Fragments were end repaired and 5' phosphorylated and 3' adenylated according to the manufacturer's instructions. Illumina paired end adapters were ligated to the gDNA fragments using a 10:1 molar ratio of adapter to gDNA. Enriched pre capture and flow cell specific sequences were added using Illumina PE PCR primers 1.0 and 2.0 for 4 PCR cycles. 500 ng of adapter ligated, PCR enriched gDNA fragments were hybridized to Agilent's SureSelect biotinylated mouse whole exome RNA library baits for 24 hrs at 65° C. Hybridized gDNA/RNA bait complexes where removed using streptavidin coated magnetic beads, washed and the RNA baits cleaved off during elution in SureSelect elution buffer. These eluted gDNA fragments were PCR amplified post capture 10 cycles. Exome enriched gDNA libraries were clustered on the cBot using Truseq SR cluster kit v2.5 using 7 pM and 50 bps were sequenced on the Illumina HiSeq2000 using Truseq SBS kit-HS 50 bp.

RNA gene expression "transcriptome" profiling (RNA-Seq): Barcoded mRNA-seq cDNA libraries were prepared in triplicate, from 5 pg of total RNA (modified Illumina mRNA-seq protocol). mRNA was isolated using Seramag Oligo(dT) magnetic beads (Thermo Scientific) and fragmented using divalent cations and heat. Resulting fragments (160-220 bp) were converted to cDNA using random primers and SuperScriptII (Invitrogen) followed by second strand synthesis using DNA polymerase I and RNaseH. cDNA was end repaired, 5' phosphorylated and 3' adenylated according to the manufacturer's instructions. 3' single T-overhang Illumina multiplex specific adapters were ligated with T4 DNA ligase using a 10:1 molar ratio of adapter to cDNA insert. cDNA libraries were purified and size selected at 200-220 bp (E-Gel 2% SizeSelect gel, Invitrogen). Enrichment, adding of Illumina six base index and flow cell specific sequences was done by PCR using Phusion DNA polymerase (Finnzymes). All cleanups up to this step were done with 1.8× volume of AgencourtAMPure XP magnetic beads. All quality controls were done using Invitrogen's Qubit HS assay and fragment size was determined using Agilent's 2100 Bioanalyzer HS DNA assay. Barcoded RNA-Seq libraries were clustered and sequenced as described above.

NGS data analysis, gene expression: The output sequence reads from RNA samples were preprocessed according to the Illumina standard protocol, including filtering for low quality reads. Sequence reads were aligned to the mm9 reference genomic sequence (Waterston R H et al., Nature 2002; 420:520-62) with bowtie (version 0.12.5) (Langmead B et al., Genome Biol 2009; 10:R25). For genome alignments, two mismatches were allowed and only the best alignment ("−v2-best") was recorded; for transcriptome alignments the default parameters were used. Reads not alignable to the genomic sequence were aligned to a database of all possible exon-exon junction sequences of RefSeq transcripts (Pruitt K D et al., Nucleic Acids Res 2007; 35:D61-D65). Expression values were determined by intersecting read coordinates with those of RefSeq transcripts, counting overlapping exon and junction reads, and normalizing to RPKM expression units (Reads which map per Kilobase of exon model per million mapped reads) (Mortazavi A et al., Nat Methods 2008; 5:621-8).

NGS data analysis, somatic mutation discovery: Somatic mutations were identified as described in Example 9. 50 nucleotide (nt), single-end reads were aligned to the mm9 reference mouse genome using bwa (default options, version 0.5.8c) (Li H and Durbin R, Bioinformatics 2009; 25:1754-60). Ambiguous reads mapping to multiple locations of the genome were removed. Mutations were identified using three software programs: samtools (version 0.1.8) (Li H, Bioinformatics 2011; 27:1157-8), GATK (version 1.0.4418) (McKenna A et al, Genome Res 2010; 20:1297-303), and SomaticSniper (http://genome.wustl.edu/software/somaticsniper) (Ding L et al., Hum Mol Genet 2010; 19:R188-R196). Potential variations identified in all B16F10 triplicates were assigned a "false discovery rate" (FDR) confidence value (cf. Example 9).

Mutation Selection, Validation, and Function

Selection: Mutations had to fulfill following criteria to be selected: (i) present in all B16F10 and absent in all C57BL/6 triplicates, (ii) FDR <0.05, (iii) homogeneous in C57BL/6, (iv) occur in a RefSeq transcript, and (v) cause non-synonymous changes to be scored as an authentic mutation. Selection for validation and immunogenicity testing required that mutations are expressed genes (median RPKM across replicates >10).

Validation: DNA-derived mutations were classified as validated if confirmed by either Sanger sequencing or the B16F10 RNA-Seq reads. All selected variants were amplified from 50 ng of DNA from B16F10 cells and C57BL/6 tail tissue using flanking primers, products visualized (QIAxcel system, Qiagen) and purified (QIAquick PCR Purification Kit, Qiagen). The amplicon of the expected size was excised from the gel, purified (QIAquick Gel Extraction Kit, Qiagen) and subjected to Sanger sequencing (Eurofins MWG Operon, Ebersberg, Germany) with the forward primer used for PCR amplification.

Functional impact: The programs SIFT (Kumar P et al., Nat Protoc 2009; 4:1073-81) and POLYPHEN-2 (Adzhubei I A et al., Nat Methods 2010; 7:248-9), which predict the functional significance of an amino acid on protein function based on the location of protein domains and cross-species sequence conservation, were employed to assess the impact of selected mutations. Ingenuity IPA tools were used to infer gene function.

Synthetic Peptides and Adjuvants

All peptides including ovalbumin class I ($OVA_{258-265}$), class II (OVA class $II_{330-338}$), influenza nucleoprotein (Inf-$NP_{366-374}$), vesiculo-stomatitis virus nucleoprotein ($VSV$-$NP_{52-59}$) and tyrosinase-related protein 2 ($Trp2_{180-188}$) were purchased from Jerini Peptide Technologies (Berlin, Germany). Synthetic peptides were 27 amino acids long with the mutated (MUT) or wild type (WT) amino acid on position 14. Polyinosinic:polycytidylic acid (poly(I:C), InvivoGen) was used as subcutaneously injected adjuvant. MHC-Pentamer specific for the Inf-$NP_{366-374}$ peptide was purchased from ProImmune Ltd.

Immunization of Mice

Age-matched female mice C57BL/6 mice were injected subcutaneously with 100 pg peptide and 50 pg poly(I:C) formulated in PBS (200 μl total volume) into the lateral flank (5 mice per group). Every group was immunized on day 0 and day 7 with two different mutation coding peptides, one peptide per flank. Twelve days after the initial injection mice were sacrificed and splenocytes were isolated for immunological testing.

Alternatively, age-matched female mice C57BL6 mice were injected intravenously with 20 pg in vitro transcribed RNA formulated with 20 μl Lipofectamine™ RNAiMAX (Invitrogen) in PBS in a total injection volume of 200 μl (3 mice per group). Every group was immunized on day 0, 3, 7, 14 and 18. Twenty-three days after the initial injection mice were sacrificed and splenocytes were isolated for immunological testing. DNA-sequences representing one (Monoepitope), two (Biepitope), or 16 mutations (Polyepitope) were constructed using 50 amino acids (aa) with the mutation on position 25 (Biepitope) or 27 aa with the mutation on position 14 (Mono- and Polyepitope), were separated by a glycin/serine linker of 9aa and cloned into the pST1-2BgUTR-A120 backbone (Holtkamp et al., Blood 2006; 108:4009-17). In vitro transcription from this template and purification were previously described (Kreiter et al., Cancer Immunol Immunother 2007; 56:1577-87).

Enzyme-Linked Immunospot Assay

Enzyme-linked immunospot (ELISPOT) assay (Kreiter S et al., Cancer Res 2010; 70:9031-40) and generation of syngeneic bone marrow derived dendritic cells (BMDCs) as stimulators were previously described (Lutz M B et al., J Immunol Methods 1999; 223:77-92). BMDCs were either peptide pulsed (2 μg/ml), or transfected with in vitro transcribed (IVT) RNA coding for the indicated mutation or for control RNA (eGFP-RNA). Sequences representing two mutations, each comprising 50 amino acids with the mutation on position 25 and separated by a glycin/serine linker of 9aa were cloned into the pST-2BgUTR-A120 backbone (Holtkamp S et al., Blood 2006; 108:4009-17). In vitro transcription from this template and purification were previously described (Kreiter S et al., Cancer Immunol Immunother 2007; 56:1577-87). For the assay, $5×10^4$ peptide or RNA engineered BMDCs were coincubated with $5×10^3$ freshly isolated splenocytes in a microtiter plate coated with anti-IFN-γ antibody (10 pg/mL, clone AN18; Mabtech). After 18 hours at 37° C., cytokine secretion was detected with an anti-IFN-γ antibody (clone R4-6A2; Mabtech). Spot numbers were counted and analyzed with the ImmunoSpot® S5 Versa ELISPOT Analyzer, the ImmunoCapture™ Image Acquisition software and the ImmunoSpot® Analysis software Version 5. Statistical analysis was done by student's t-test and Mann-Whitney test (non-parametric test). Responses were considered significant, when either the test gave a p-value <0.05 and the mean spot numbers were >30 spots/5×10$^5$ effector cells. Reactivities were rated by mean spot numbers (−: <30; +: >30; ++: >50; +++>200 spots/well).

Intracellular Cytokine Assay

Aliquots of the splenocytes prepared for the ELISPOT assay were subjected to analysis of cytokine production by intracellular flow cytometry. To this end 2×10$^6$ splenocytes per sample were plated in culture medium (RPMI+10% FCS) supplemented with the Golgi inhibitor Brefeldin A (10 μg/mL) in a 96-well plate. Cells from each animal were restimulated for 5 h at 37° C. with 2×10$^5$ peptide pulsed BMDCs. After incubation the cells were washed with PBS, resuspended in 50 μl PBS and extracellularly stained with the following anti-mouse antibodies for 20 min at 4° C.: anti-CD4 FITC, anti-CD8 APC-Cy7 (BD Pharmingen). After incubation the cells were washed with PBS and subsequently resuspended in 100 μL Cytofix/Cytoperm (BD Bioscience) solution for 20 min at 4° C. for permeabilization of the outer membrane. After permeabilization the cells were washed with Perm/Wash-Buffer (BD Bioscience), resuspended in 50 μL/sample in Perm/Wash-Buffer and intracellularly stained with the following anti-mouse antibodies for 30 min at 4° C.: anti-IFN-γ PE, anti-TNF-α PE-Cy7, anti-IL2 APC (BD Pharmingen). After washing with Perm/Wash-Buffer the cells were resuspended in PBS containing 1% paraformyldehyde for flow cytometry analysis. The samples were analyzed using a BD FACSCanto™ II cytometer and FlowJo (Version 7.6.3).

B16 Melanoma Tumor Model

For tumor vaccination experiments 7.5×10$^4$ B16F10 melanoma cells were inoculated s.c. into the flanks of C57BL/6 mice. In the prophylactic setting, immunization with mutation-specific peptide was performed 4 days before and on days 2 and 9 after tumor inoculation. For the therapeutic experiment the peptide vaccine was administered on days 3 and 10 after tumor injection. The tumor sizes were measured every three days and mice were sacrificed when tumor diameter reached 15 mm.

Alternatively, for tumor vaccination experiments 1×10$^5$ B16F10 melanoma cells were inoculated s.c. into the flanks of age-matched female C57BL/6 mice. Peptide vaccination was performed on days 3, 10 and 17 after tumor inoculation with 100 pg peptide and 50 pg poly(I:C) formulated in PBS (200 μl total volume) injected subcutaneously into the lateral flank. RNA immunizations were performed using 20 pg in vitro transcribed mutation-encoding RNA formulated with 20 μl Lipofectamine™ RNAiMAX (Invitrogen) in PBS in a total injection volume of 200 μl. As control one group of animals was injected with RNAiMAX (Invitrogen) in PBS. The animals were immunized on days 3, 6, 10, 17 and 21 after tumor inoculation. The tumor sizes were measured every three days using a caliper and mice were sacrificed when tumor diameter reached 15 mm.

Identification of Non-Synonymous Mutations in B16F10 Mouse Melanoma

Our objective was to identify potentially immunogenic somatic point mutations in B16F10 mouse melanoma by NGS and to test these for in vivo immunogenicity by peptide vaccination of mice measuring elicited T-cell responses by ELISPOT assay (FIG. 9A). We sequenced the exomes of the C57BL/6 wild type background genome and of B16F10 cells, each with triplicate extractions and captures. For each sample, more than 100 million single-end 50 nt reads were generated. Of these 80%, align uniquely to the mouse mm9 genome and 49% align on target, demonstrating successful target enrichment and resulting in over 20-fold coverage for 70% of the target nucleotides in each of the triplicate samples. RNA-Seq of B16F10 cells, also profiled in triplicate, generated a median of 30 million single-end 50 nt reads, of which 80% align to the mouse transcriptome.

DNA reads (exome-capture) from B16F10 and C57BL/6 were analyzed to identify somatic mutations. Copy number variation analysis (Sathirapongsasuti J F et al., Bioinformatics 2011; 27:2648-54) demonstrated DNA amplifications and deletions in B16F10, including the homozygous deletion of tumor suppressor Cdkn2a (Cyclin-dependent kinase inhibitor 2A, p16Ink4A). Focusing on point mutations to identify possible immunogenic mutations, we identified 3570 somatic point mutations at FDR ≤0.05 (FIG. 9B). The most frequent class of mutations were C>T/G>A transitions, typically resulting from ultraviolet light (Pfeifer G P et al., Mutat Res 2005; 571:19-31). Of these somatic mutations, 1392 occur in transcripts, with 126 mutations in untranslated regions. Of the 1266 mutations in coding regions, 962 cause non-synonymous protein changes and 563 of these occur in expressed genes (FIG. 9B).

Assignment of Identified Mutations to Carrier Genes and Validation

Noteworthy, many of the mutated genes (962 genes containing non-synonymous somatic point mutations) have been previously associated with the cancer phenotypes. Mutations were found in established tumor suppressor genes, including Pten, Trp53 (also called p53), and Tp63. In Trp53, the best established tumor suppressor (Zilfou J T et al., Cold Spring Harb Perspect Biol 2009; 1:a001883), the asparagine to aspartic acid mutation at protein position 127 (p.N127D) is localized in the DNA binding domain and is predicted by SIFT to alter function. Pten contained two mutations (p.A39V, p.T131P), both of which are predicted to have deleterious impact on protein function. The p.T131P mutation is adjacent to a mutation (p.R130M) shown to diminish phosphatase activity (Dey N et al., Cancer Res 2008; 68:1862-71). Moreover, mutations were found in genes associated with DNA repair pathways, such as Brca2 (breast cancer 2, early onset), Atm (ataxia telangiectasia mutated), Ddbl (damage-specific DNA binding protein 1) and Rad9b (RAD9 homolog B). Furthermore, mutations occur in other tumor associated genes, including Aim) (tumor suppressor "Absent In Melanoma 1"), Flt1 (oncogene Vegr1, fins-related tyrosine kinase 1), Pml (tumor suppressor "promyelocytic leukemia"), Fat1 ("FAT tumor suppressor homolog 1"), Mdm1 (TP53 binding nuclear protein), Mta3 (metastasis associated 1 family, member 3), and Alk (anaplastic lymphoma receptor tyrosine kinase). We found a mutation at p.S144F in Pdgfra (platelet-derived growth factor receptor, alpha polypeptide), a cell-membrane-bound receptor tyrosine kinase of the MAPK/ERK pathway, previously identified in tumors (Verhaak R G et al., Cancer Cell 2010; 17:98-110). A mutation occurs at p.L222V in Casp9 (caspase 9, apoptosis-related cysteine peptidase). CASP9 proteolytically cleaves poly(ADP-ribose) polymerase (PARP), regulates apoptosis, and has been linked to several cancers (Hajra K M et al., Apoptosis 2004; 9:691-704). The mutation we found may potentially impact PARP and apoptosis signaling. Most interestingly, no mutations were found in Braf, c-Kit, Kras or Nras. However, mutations were identified in Rass7 (RAS-associated protein) (p.S90R), Ksr1 (kinase suppressor of ras 1) (p.L301V), and Atm (PI3K pathway) (p.K91T), all of which are predicted to have significant impact on protein function. Trrap (transformation/transcription domain-associated protein) was identified earlier this year in human melanoma specimens as a novel potential melanoma target (Wei X et al., Nat Genet 2011; 43:442-6). In B16F10, a Trrap mutation occurs at p.K2783R and is predicted to disturb the overlapping phosphatidylinositol kinase (PIK)-related kinase FAT domain.

From the 962 non-synonymous mutations identified using NGS, we selected 50 mutations, including 41 with FDR <0.05, for PCR-based validation and immunogenicity testing. Selection criteria were location in an expressed gene (RPKM >10) and predicted immunogenicity. Noteworthy, we were able to validate all 50 mutations (Table 6, FIG. 9B).

TABLE 6

Mutations selected for validation.
From left: assigned ID, gene symbol, amino acid substitution and position, gene name, predicted subcellular localization and type (Ingenuity).

| ID | Symbol | Change | Entrez Gene Name | Subcellular localization | Type |
|---|---|---|---|---|---|
| MUT1 | Fzd7 | p.G304A | frizzled family receptor 7 | Plasma Membrane | G-protein coupled receptor |
| MUT2 | χpot | p.t830S | exportin, tRNA (nuclear export receptor for tRNAs) | Nucleus | other |
| MUT3 | Ranbp2 | p.Q2871H | RAN binding protein 2 | Nucleus | enzyme |
| MUT4 | Dnajb12 | p.P54T | DnaJ (Hsp40) homolog, subfamily B. member 12 | Cytoplasm | other |
| MUT5 | Eef2 | p.G795A | eukaryotic translation elongation factor 2 | Cytoplasm | translation regulator |
| MUT6 | Ptrf | p.D382G | polymerase I and transcript release factor | Nucleus | transcription regulator |
| MUT7 | Trp53 | p.N128D | tumor protein p53 | Nucleus | transcription regulator |
| MUT8 | Ddx23 | p.V602A | DEAD (Asp-Glu-Ala-Asp) box polypeptide 23 | Nucleus | enzyme |
| MUT9 | Golgb1 | p.E2855D | golgin B1 | Cytoplasm | other |
| MUT10 | Pcdhga11 | p.G82R | protocadherin gamma subfamily A, 11 | Plasma Membrane | other |
| MUT11 | Snx15 | p.E211G | sorting nexin 15 | Cytoplasm | transporter |
| MUT12 | Gnas | p.S112G | GNAS (guanine nucleotide binding protein, alpha stimulating) complex locus | Plasma Membrane | enzyme |
| MUT13 | Fndc3b | p.C561W | fibronectin type III domain containing 3B | Cytoplasm | other |
| MUT14 | Sbno1 | p.P309T | strawberry notch homolog 1 (*Drosophila*) | unknown | enzyme |
| MUT15 | Pi4k2b | p.R344Q | phosphatidylinositol 4-kinase type 2 beta | Cytoplasm | kinase |
| MUT16 | Thumpd3 | p.T243S | THUMP domain containing 3 | unknown | other |
| MUT17 | Tnpo3 | p.G504A | transportin 3 | Cytoplasm | other |
| MUT18 | Numa1 | p.Q447K | nuclear mitotic apparatus protein 1 | Nucleus | other |
| MUT19 | Wwp2 | p.E742K | WW domain containing E3 ubiquitin protein ligase 2 | Cytoplasm | enzyme |
| MUT20 | Tubb3 | p.G402A | tubulin, beta 3 | Cytoplasm | other |
| MUT21 | Atp11a | p.R522S | ATPase, class VI, type 11A | Plasma Membrane | transporter |
| MUT22 | Asf1b | p.A141P | ASF1 anti-silencing function 1 homolog B (*S. cerevisiae*) | Nucleus | other |
| MUT23 | Wdr82 | p.I221L | WD repeat domain 82 | Nucleus | other |
| MUT24 | Dag1 | p.P425A | dystroglycan 1 (dystrophin-associated glycoprotein 1) | Plasma Membrane | transmembrane receptor |
| MUT25 | Plod2 | p.F530V | procollagen-lysine, 2-oxoglutarate 5-dioxygenase 2 | Cytoplasm | enzyme |
| MUT26 | Orc2 | p.F278V | origin recognition complex, subunit 2 | Nucleus | other |
| MUT27 | Obsl1 | p.T1764M | obscurin-like 1 | unknown | other |
| MUT28 | Ppp1r7 | p.L170P | protein phosphatase 1, regulatory (inhibitor) subunit 7 | Nucleus | phosphatase |
| MUT29 | Mthfd1l | p.F294V | methylenetetrahydrofolate dehydrogenase (NADP+ dependent) 1-like | Cytoplasm | enzyme |
| MUT30 | Kif18b | p.K739N | kinesin family member 18B | unknown | other |
| MUT31 | Ascc2 | p.A59G | activating signal cointegrator 1 complex subunit 2 | unknown | other |
| MUT32 | Itsn2 | p.S1551R | intersectin 2 | Cytoplasm | other |
| MUT33 | Pbk | p.V145D | PDZ binding kinase | Cytoplasm | kinase |
| MUT34 | Klhl22 | p.F179V | kelch-like 22 (*Drosophila*) | unknown | other |
| MUT35 | Ddb1 | p.L438I | damage-specific DNA binding protein 1, 127 kDa | Nucleus | other |
| MUT36 | Tm9sf3 | p.Y382H | transmembrane 9 superfamily member 3 | Cytoplasm | transporter |
| MUT37 | Dpf2 | p.F275V | D4, zinc and double PHD fingers family 2 | Nucleus | other |
| MUT38 | Atrn | p.S745N | attractin | Extracellular Space | other |
| MUT39 | Snx5 | p.R373Q | sorting nexin 5 | Cytoplasm | transporter |
| MUT40 | Armc1 | p.S85I | armadillo repeat containing 1 | Cytoplasm | other |
| MUT41 | Ash1l | p.L632I | ash1 (absent, small, or homeotic)-like (*Drosophila*) | Nucleus | transcription regulator |
| MUT42 | S100a13 | p.S18C | S100 calcium binding protein A13 | Cytoplasm | other |
| MUT43 | 2510039O18 Rik | p.E391K | KIAA2013 | unknown | other |
| MUT44 | Cpsf3l | p.D314N | cleavage and polyadenylation specific factor 3-like | Nucleus | other |
| MUT45 | Mkrn1 | p.N346Y | makorin ring finger protein 1 | unknown | other |
| MUT46 | Actn4 | p.F835V | actinin, alpha 4 | Cytoplasm | other |
| MUT47 | Rpl13a | p.A24G | ribosomal protein L13a | Cytoplasm | other |
| MUT48 | Def8 | p.R255G | differentially expressed in FDCP 8 homolog (mouse) | unknown | other |
| MUT49 | Fat1 | p.I1940M | FAT tumor suppressor homolog 1 (*Drosophila*) | Plasma Membrane | other |
| MUT50 | Sema3b | p.L663V | sema domain, immunoglobulin domain (Ig), short basic domain, secreted, (semaphorin) 3B | Extracellular Space | other |

FIG. 9C shows the locations of the B16F10 chromosomes, genes density, gene expression, mutations, and filtered mutations (inner rings).

In Vivo Testing of Immunogenicity Testing with Mutation-Representing Long Peptides To provide antigens for immunogenicity testing of these mutations, we employed long peptides which have many advantages over other peptides for immunization (Melief C J and van der Burg S H, Nat Rev Cancer 2008; 8:351-60). Long peptides are capable of inducing antigen-specific CD8+ as well as CD4+ T-cells (Zwaveling S et al., Cancer Res 2002; 62:6187-93; Bijker M S et al., J Immunol 2007; 179:5033-40). Moreover, long peptides require processing to be presented on MHC molecules. Such uptake is most efficiently done by dendritic cells, which are optimal for priming a potent T-cell response. Fitting peptides, in contrast, do not require trimming and are loaded exogenously on all cells expressing MHC molecules, including non-activated B and T-cells, leading to induction of tolerance and fratricide (Toes R E et al., J Immunol 1996; 156:3911-8; Su M W et al., J Immunol 1993; 151:658-67). For each of the 50 validated mutations, we designed peptides of 27 amino acids length with the mutated or wild type amino acid positioned centrally. Thus, any potential MHC class I and class II epitope of 8 to 14 amino acid length carrying the mutation could be processed from this precursor peptide. As adjuvant for peptide vaccination we used poly(I:C) which is known to promote cross presentation and increase vaccine efficacy (Datta S K et al., J Immunol 2003; 170:4102-10; Schulz O et al., Nature 2005; 433:887-92). The 50 mutations were tested in vivo in mice for induction of T-cells. Impressively, 16 out of 50 mutation-coding peptides were found to elicit immune responses in immunized mice. The induced T-cells displayed different reactivity patterns (Table 7).

TABLE 7

Summary of T-cell reactivities determined consecutive to vaccination with mutation encoding peptide. Statistical analysis was done by student's t-test and Mann-Whitney test (non-parametric test). Responses were considered significant, when either test gave a p-value < 0.05 and the mean spot numbers were >30 spots/5 × $10^5$ effector cells.

| Mutation | Gene Symbol | Reactivity against mutation | Reactivity against WT |
|---|---|---|---|
| MUT01 | Fzd⁻ | − | − |
| MUT02 | Xpot | − | − |
| MUT03 | Ranbp2 | − | − |
| MUT04 | Dnajb12 | − | − |
| MUT05 | Eef2 | +++ | +++ |
| MUT06 | Ptrf | − | − |
| MUT07 | Trp53 | − | − |
| MUT08 | Ddx23 | − | − |
| MUT09 | Golgb1 | − | − |
| MUT10 | Pcdhga11 | − | − |
| MUT11 | Snx15 | − | − |
| MUT12 | Gnas | + | − |
| MUT13 | Fndc3b | − | − |
| MUT14 | Sbno1 | − | − |
| MUT15 | Pi4k2b | − | − |
| MUT16 | Thumpd3 | − | − |
| MUT17 | Tnpo3 | +++ | ++ |
| MUT18 | NumaJ | − | − |
| MUT19 | Wwp2 | − | − |
| MUT20 | Tubb3 | +++ | − |
| MUT21 | Arp11a | − | − |
| MUT22 | Asf1b | ++ | ++ |
| MUT23 | WdrS2 | − | − |
| MUT24 | Dag1 | ++ | + |
| MUT25 | Plod2 | +++ | ++ |

TABLE 7-continued

Summary of T-cell reactivities determined consecutive to vaccination with mutation encoding peptide. Statistical analysis was done by student's t-test and Mann-Whitney test (non-parametric test). Responses were considered significant, when either test gave a p-value < 0.05 and the mean spot numbers were >30 spots/5 × $10^5$ effector cells.

| Mutation | Gene Symbol | Reactivity against mutation | Reactivity against WT |
|---|---|---|---|
| MUT26 | Orc2 | − | − |
| MUT27 | Obsl1 | − | − |
| MUT28 | Ppp1r7 | + | + |
| MUT29 | Mthfd1l | + | − |
| MUT30 | Kif1Sb | +++ | − |
| MUT31 | Ascc2 | − | − |
| MUT32 | Itsn2 | − | − |
| MUT33 | Pbk | − | − |
| MUT34 | Klhl22 | − | − |
| MUT35 | Ddb1 | − | − |
| MUT36 | Tm9sf3 | + | − |
| MUT37 | Dpf2 | − | − |
| MUT38 | Atrn | − | − |
| MUT39 | Snx5 | − | − |
| MUT40 | Armc1 | − | − |
| MUT41 | Ash1l | − | − |
| MUT42 | S100a13 | − | − |
| MUT43 | Rik | − | − |
| MUT44 | Cpsf31 | +++ | ++ |
| MUT45 | Mkrn1 | ++ | ++ |
| MUT46 | Actn4 | ++ | + |
| MUT47 | Rpl13a | − | − |
| MUT48 | DefS | ++ | ++ |
| MUT49 | Fat1 | − | − |
| MUT50 | Sema3b | +++ | ++ |

Reactivities were rated by mean spot numbers −: <30; +: >30; ++: >50; +++ >200 spots/well.

Eleven peptides induced an immune response preferentially recognizing the mutated epitope. This is exemplified for mice immunized with mutations 30 (MUT30, Kif18b) and 36 (MUT36, Plod2) (FIG. 10A). ELISPOT testing revealed strong mutation-specific immune responses without cross reactivity against the wild-type peptide or an unrelated control peptide (VSV-NP). With five peptides, including mutations 05 (MUT05, EeJ2) and 25 (MUT25, Plod2) (FIG. 10A), immune responses with comparable recognition of both the mutated as well as the wild-type peptide were obtained. The majority of mutated peptides were not capable of inducing significant T-cell responses as exemplified by mutations 01 (MUT01, Fzd7), 02 (MUT02, Xpot), and 07 (MUT07, Trp53). Immune responses induced by several of the discovered mutations were well in the range of immunogenecity (500 spots/5×$10^5$ cells) generated by immunizing mice as a positive control with a described MHC-class I epitope from the murine melanoma tumor antigen tyrosinaserelated protein 2 (Trp2180-188, FIG. 10A) (Bloom M B et al., Exp Med 1997; 185:453-9; Schreurs M W et al. Cancer Res 2000; 60:6995-7001). For selected peptides that induce a strong mutation-specific T-cell response, we confirmed immune recognition by an independent approach. Instead of long peptides, in vitro transcribed RNA (IVT RNA) coding for the mutated peptide fragments MUT17, MUT30 and MUT44 was used for the immunological read-out. BMDCs transfected with mutation-coding RNA or irrelevant RNA served as antigen presenting cells (APCs) in an ELISPOT assay, whereas spleen cells of immunized mice served as effector cell population. BMDCs transfected with MUT17, MT30 and MUT44 encoding mRNA were specifically and strongly recognized by splenocytes of mice immunized with the respective long peptides (FIG. 10B). Significantly lower reactivity against control RNA-transfected BMDCs was recorded, which is likely due to the unspecific activation of the BMDCs by the single stranded RNA (student's t-test; MUT17: p=0.0024, MUT30: p=0.0122, MUT44: p=0.0075). These data confirm that the induced mutation-specific T-cells in effect recognize endogenously processed epitopes. Two mutations that induce a preferred recognition of mutated epitopes are in genes Actn4 and Kif18b. The somatic mutation in ACTN4 (actinin, alpha 4) is at p.F835V in the calcium binding "EF-hand" protein domain. While both SIFT and POLYPHEN predict a significant impact of this mutation on protein function, the gene is not an established oncogene. However, mutation-specific T-cells against ACTN4 have been recently associated with a positive patient outcome (Echchakir H et al., Cancer Res 2001; 61:4078-83). KIF18B (kinesin family member 18B) is a kinesin with microtubule motor activity and ATP and nucleotide binding that is involved in regulation of cell division (Lee Y M et al., Gene 2010; 466:16-25) (FIG. 10C). The DNA sequence at the position encoding p.K739 is homogeneous in the reference C57BL/6, whereas B16F10 DNA reads reveal a heterozygous somatic mutation. Both nucleotides were detected in the B16F10 RNA-Seq reads and validated by Sanger sequencing. KIF18B has not been previously associated with a cancer phenotype. The mutation p.K739N is not localized in a known functional or conserved protein domain (FIG. 10C, bottom) and thus most likely is a passenger rather than a driver mutation. These examples suggest a lack of correlation between the capability of inducing mutation-recognizing immune response and a functional or immunological relevance.

In Vivo Assessment of Antitumoral Activity of Vaccine Candidates

To assess whether immune responses elicited in vivo translate in anti-tumoral effects in tumor bearing mice, we chose MUT30 (mutation in Kif18b) and MUT44 as examples. These mutations had been shown to induce a strong immune reaction preferentially against the mutated peptide and to be endogenously processed (FIG. 10A, B). The therapeutical potential of vaccinating with mutated peptides was explored by immunizing mice with either MUT30 or MUT44 and adjuvant 3 and 10 days after grafting with $7.5 \times 10^5$ B16F10. Growth of tumors was inhibited by both peptide vaccinations as compared to the control group (FIG. 11A). As B16F10 is a very aggressively growing tumor, we also tested protective immune responses. Mice were immunized with MUT30 peptide, inoculated s.c. with $7.5 \times 10^3$ B16F10 cells 4 days later and boosted with MUT30 2 and 9 days after tumor challenge. Complete tumor protection and survival of 40% of the mice treated with MUT30 were observed, whereas all mice in the control treated group died within 44 days (FIG. 11B left). In those mice, developing tumors despite immunization with MUT30, growth of tumors was slower resulting in an elongation of the median survival by 6 days as compared to the control group (FIG. 11B right). These data imply that already vaccination against a single mutation is able to confer anti-tumoral effects.

Immunization with Mutation-Coding RNAs

The 50 validated mutations from the B16F10 melanoma cell line were used to construct different RNA vaccines. DNA-sequences representing one (Monoepitope), two (Biepitope), or 16 different mutations (Polyepitope), were constructed using 50 amino acids (aa) with the mutation on position 25 (Biepitope) or 27 aa with the mutation on position 14 (Mono- and Polyepitope) and were separated by a glycine/serine linker of 9aa. These constructs were cloned into the pST1-2BgUTR-A120 backbone for in vitro transcription of mRNA (Holtkamp et al., Blood 2006; 108:4009-17).

To test the in vivo ability to induce T-cell responses against the different RNA-vaccines groups of three C57BL/6 mice were immunized by formulation of the RNA with RNAiMAX lipofectamine and subsequent intravenous injection. After 5 immunizations the mice were sacrificed and splenocytes were analyzed for mutation-specific T-cell responses using intracellular cytokine staining and IFN-γ ELISPOT analysis after restimulation with the corresponding mutation coding peptide or control peptide (VSV-NP).

FIG. 12 shows one example for each vaccine design. In the upper row the mice were vaccinated with the Monoepitope-RNA coding for MUT30 (mutation in Kif78b), which induces MUT30-specific CD4⁺ T-cells (see exemplary FACS-plot). In the middle row the graph and FACS-plot show induction of MUT08-specific (mutation in Ddx23) CD4⁺ T-cells after immunization with the Biepitope coding for MUT33 and MUT08. In the lower row mice were immunized with a Polyepitope encoding 16 different mutations including MUT08, MUT33 and MUT27 (see Table 8). The graph and FACS-plot illustrate that MUT27 reactive T-cells are of a CD8 phenotype.

TABLE 8

Overview of mutations and gene names encoded by Mono-, Bi- and Polyepitope RNA-vaccines.

| Construct | Encoded mutation | Gene annotation |
| --- | --- | --- |
| Monoepitope | MUT30 | Kif18b |
| Biepitope | MUT33 | Pbk |
|  | MUT08 | Ddx23 |
| Polyepitope | MUT01 | Fzd7 |
|  | MUT02 | Xpot |
|  | MUT03 | Ranbp2 |
|  | MUT04 | Dnajb12 |
|  | MUT05 | Eef2 |
|  | MUT06 | Ptrf |
|  | MUT07 | Trp53 |
|  | MUT08 | Ddx23 |
|  | MUT26 | Orc2 |
|  | MUT27 | Obsl1 |
|  | MUT28 | Ppp1r7 |
|  | MUT29 | Mthfd1l |
|  | MUT30 | Kif18b |
|  | MUT31 | Ascc2 |
|  | MUT32 | Itsn2 |
|  | MUT33 | Pbk |

The same Polyepitope was used to generate the data shown in FIG. 13. The graph shows ELISPOT data after restimulation of splenocytes with control (VSV-NP), MUT08, MUT27 and MUT33 peptides, proving that the Polyepitope vaccine can induce specific T-cell responses against several different mutations.

Taken together the data show the possibility to induce mutation-specific T-cells using RNA-encoded Mono-, Bi- and Polyepitopes. Furthermore, the data show induction of CD4⁺ and CD8⁺ T cells and the induction of several different specificities from one construct.

Immunization with Model Epitopes

To further characterize the polyepitopic RNA-vaccine design a DNA-sequence was constructed, which included five different known model epitopes including one MHC class II epitope (ovalbumin class I (SIINFEKL), class II (OVA class II), influenza nucleoprotein (Inf-NP), vesiculostomatitis virus nucleoprotein (VSV-NP) and tyrosinase-related protein 2 (Trp2)). The epitopes were separated with the same glycine/serine linker of 9aa used for the mutation Polyepitope. This constructs was cloned into the pST1-2BgUTR-A120 backbone for in vitro transcription of mRNA.

The in vitro transcribed RNA was used to vaccinate five C57BL/6 mice by intranodal immunization (four immunizations with 20 µg of RNA into the inguinal lymphnodes). Five days after the last immunization blood samples and splenocytes were taken from the mice for analysis. FIG. 14A shows IFN-γ ELISPOT analysis of the splenocytes restimulated with the indicated peptides. It can be clearly seen that all three MHC-class I epitope (SIINFEKL, Trp2 and VSV-NP) induce a very high number of antigen-specific CD8+ T cells. Also the MHC-class II epitope OVA class II induces a strong CD4+ T-cell response. The fourth MHC class I epitope was analyzed by staining of Inf-NP-specific CD8+ T-cells with a fluorescence-labeled pentameric MHC-peptide complex (Pentamer) (FIG. 14B).

These data prove that the polyepitope design using the glycine/serine linker to separate different immunogenic MHC-class I and -class II epitopes is able to induce specific T-cells against every encoded epitope, regardless of its immunodominance.

Anti-Tumoral Response after Therapy with a Mutation-Encoding Polyepitopic RNA Vaccine The same Polyepitope which was analyzed in FIG. 13 for immunogenicity was used to investigate the anti-tumoral activity of the mutation-encoding RNAs against the B16F10 tumor cells. In detail, groups of C57BL/6 mice (n=10) were subcutaneously inoculated with 1 ×10$^5$ B16F10 melanoma cells into the flank. On days 3, 6, 10, 17 and 21 the mice were immunized with the polytopic RNA using a liposomal transfection reagent. The control group was injected with liposomes alone.

FIG. 21 shows the survival curves of the groups, revealing a strongly improved median survival of 27 days with 1 of 10 mice surviving without tumor compared to 18.5 days median survival in the control group.

Anti-Tumoral Response after Therapy with a Combination of Mutated and Normal Peptide Anti-tumoral activity of the validated mutations was evaluated by a therapeutic in vivo tumor experiment by using the MUT30 as a peptide vaccine. In detail, groups of C57BL/6 mice (n=8) were subcutaneously inoculated with 1×10$^5$ B16F10 melanoma cells into the flank. On day 3, 10 and 17 the mice were immunized using polyI:C as adjuvant with MUT30, tyrosinase-related protein 2 (Trp2$_{180-188}$) or a combination of both peptides. Trp2 is a known CD8+ epitope expressed by the B16F10 melanoma cells.

FIG. 15A shows the mean tumor growth of the groups. It can be clearly seen that until day 28 the tumor growth is almost completely inhibited in the group which was immunized with the combination of the known CD8+ T-cell epitope and the CD4+ T-cell inducing MUT30. The known Trp2 epitope alone is not sufficient to provide a good anti-tumoral effect in this setting, but both single therapy groups (MUT30 and Trp2) still provide a tumor growth inhibition in comparison to the untreated group in the beginning of the experiment up to day 25. These data are strengthened by the survival curves shown in FIG. 15B. Clearly the median survival is increased by the mice injected with the single peptides, with ⅛ mice surviving in the group with Trp2 vaccination. In addition the group treated with both peptides shows an even better median survival with ⅖ mice surviving.

Taken together both epitopes act in a synergistic manner to provide a strong anti-tumoral effect.

Example 9: Framework for Confidence-Based Somatic Mutation Detection and Application to B16-F10 Melanoma Cells NGS is unbiased in that it enables a high throughput discovery of variations within an entire genome or targeted regions, such as protein coding exons.

However, while revolutionary, the NGS platform is still prone to errors leading to erroneous variation calls. Furthermore, the quality of results is dependent on experimental design parameters and analysis methodologies. While variation calls typically include scores designed to differentiate true variations from errors, the utility of these scores is not fully understood, nor is their interpretation with regard to optimization of experiments. This is particularly true when comparing tissue states, such comparing tumor and normal for somatic mutations. As a consequence, researchers are forced to rely on personal experience to determine experimental parameters and arbitrary filtering thresholds for selecting mutations.

Our study aims a) to establish a framework for comparing parameters and methods to identify somatic mutations and b) to assign a confidence value to identified mutations. We sequence triplicate samples from C57BL/6 mice and the B16-F10 melanoma cell line. Using these data, we formulate the false discovery rate of detected somatic mutations, a measure that we then use to evaluate existing mutation discovery software and lab protocols.

Various experimental and algorithmic factors contribute to the false positive rate for variations found by NGS [Nothnagel, M. et al., Hum. Genet. 2011 Feb. 23 [Epub ahead of print]]. The error sources include PCR artifacts, biases in priming [Hansen, K. D., et al., Nucleic. Acids. Res. 38, e131 (2010); Taub, M. A. et al., Genome Med. 2, 87 (2010)] and targeted enrichment [Bainbridge, M. N. et al., Genome Biol. 11, R62 (2010)], sequence effects [Nakamura, K. et al., Acids Res. (2011) first published online May 16, 2011 doi:10.1093/nar/gkr344], base calling causing sequence errors [Kircher, M. et al., Genome Biol. 10, R83 (2009). Epub 2009 Aug. 14] and read alignment [Lassmann, T. et al., Bioinformatics 27, 130-131 (2011)], causing variation in coverage and sequencing errors which influence the further downstream analysis, e.g. variant calling around indels [Li, H., *Bioinformatics* 27, 1157-1158 (2011)].

No general statistical model has been described to describe the impact of different error sources on somatic mutation calls; only individual aspects are covered without removing all bias. Recent computational methods to measure the expected amount of false positive mutation calls include utilization of the transition/transversion ratio of a set of variations [Zhang, Z., Gerstein, M., Nucleic Acids Res 31, 5338-5348 (2003); DePristo, M. A. et al., Nature Genetics 43, 491-498 (2011)], machine learning [DePristo, M. A. et al., *Nature Genetics* 43, 491-498 (2011)] and inheritance errors when working with family genomes [Ewen, K. R. et al., Am. J. Hum. Genet. 67, 727-736 (2000)] or pooled samples [Druley, T. E. et al., Nature Methods 6, 263-265 (2009); Bansal, V., Bioinformatics 26, 318-324 (2010)]. For optimization purposes, Druley et al. [Druley, T. E. et al., Nature Methods 6, 263-265 (2009)] relied on short plasmid sequence fragments, which however might not be representative for the sample. For a set of single nucleotide variations (SNVs) and selected experiments, a comparison to SNVs identified by other techniques is feasible [Van Tassell, C. P. et al., Nature Methods 5, 247-252 (2008)] but is difficult to evaluate in terms of novel somatic mutations.

Using an exome sequencing project as an example, we propose the calculation of a false discovery rate (FDR) based on NGS data alone. The method is not only applicable to the selection and prioritization of diagnostic and therapeutic targets, but also supports algorithm and method development by allowing us to define confidence-driven recommendations for similar experiments.

To discover mutations, DNA from tail tissue of three C57BL/6 (black6) mice (litter mates) and DNA from B16-F10 (B16) melanoma cells, in triplicate, were individually enriched for protein coding exons (Agilent Sure Select Whole Mouse Exome), resulting in 6 samples. RNA was extracted from B16 cells in triplicate. Single end 50 nt (1×50 nt) and paired end 100 nt (2×100 nt) reads were generated on an Illumina HiSeq 2000. Each sample was loaded into an individual lane, resulting in an average of 104 million reads per lane. DNA reads were aligned to the mouse reference genome using bwa [Li, H. Durbin, R., Bioinformatics 25, 1754-1760 (2009)] and RNA reads were aligned with bowtie [Langmead, B. et al., Genome Biol. 10, R25 (2009)]. A mean coverage of 38 fold of 97% of the targeted regions was achieved for the 1×50 nt libraries, while the 2×100 nt experiment yielded an average coverage of 165 fold for 98% of the targeted regions.

Somatic variations were independently identified using the software packages SAMtools [Li, H. et al., Bioinformatics 25, 2078-2079 (2009)], GATK [DePristo, M. A. et al., Nature Genetics 43, 491-498 (2011)] and SomaticSNiPer (Ding, L. et al., Hum. Mol. Genet (2010) first published online Sep. 15, 2010] (FIG. 16) by comparing the single nucleotide variations found in B16 samples to the corresponding loci in the black6 samples (B16 cells were originally derived from a black6 mouse). The potential mutations were filtered according to recommendations by the respective software authors (SAMtools and GATK) or by selecting an appropriate lower threshold for the somatic score of SomaticSNiPer, respectively.

To create a false discovery rate (FDR) for mutation discovery, we first intersected the mutation sites and obtained 1,355 high quality somatic mutations as consensus among all three programs (FIG. 17). However, the observed differences in the results of the applied software tools are substantial. To avoid erroneous conclusions, we developed a method to assign a FDR to each mutation using the replicates. Technical repeats of a sample should generate identical results and any detected mutation in this "same vs. same comparison" is a false positive. Thus, to determine the false discovery rate for somatic mutation detection in a tumor sample relative to a normal sample ("tumor comparison"), we can use a technical repeat of the normal sample as a reference to estimate the number of false positives.

FIG. 18A shows examples of variations found in the black6/B16 data, including a somatic mutation (left), non-somatic variation to the reference (middle), and possible false positive (right). Each somatic mutation can be associated with a quality score Q. The number of false positives in the tumor comparison indicates a number of false positives in the same vs. same comparison. Thus, for a given mutation with quality score Q detected in the tumor comparison, we estimate the false discovery rate by computing the ratio of same vs. same mutations with a score of Q or better to the overall number of mutations found in the tumor comparison with a score of Q or better.

A challenge arises in defining Q since most mutation detection frameworks compute multiple quality scores. Here, we apply a random forest classifier [Breiman, L., Statist. Sci. 16, 199-231 (2001)] to combine multiple scores into a single quality score Q. We refer to the methods section for details regarding details of the quality score and FDR computation.

A potential bias in comparing methods is differential coverage; we thus normalize the false discovery rate for the coverage:

$$FDR(Q) = \frac{\#Same\ vs.\ Same\ SNVs\ with\ score \geq Q}{\#Tumor\ SNVs\ with\ score \geq Q} \times \frac{\#common\ coverage\ tumor\ comparison}{\#common\ coverage\ same\ vs.\ same\ comparison}$$

We calculate the common coverage by counting all bases of the reference genome which are covered by both the tumor and normal sample or by both "same vs. same" samples, respectively.

By estimating the number of false positives and positives at each FDR (see Methods), we generate receiver operating characteristic (ROC) curves and calculate the AUC (area under the curve) for each mutation discovery method, thus enabling a comparison of strategies for mutation discovery (FIG. 18B).

Furthermore, the selection of the reference data might influence the calculation of the FDRs. Using the available black6/B16 data it is possible to create 18 triplets (combinations of black6 vs. black6 and black6 vs. b16). When comparing the resulting FDR distributions for the sets of somatic mutations, the results are consistent (FIG. 18B).

Using this definition of a false discovery rate, we have established a generic framework for evaluating the influence of numerous experimental and algorithmic parameters on the resulting set of somatic mutations. Next, we apply this framework to study the influence of software tools, coverage, paired end sequencing and the number of technical replicates on somatic mutation identification.

First, the choice of the software tool has a clear impact on the identified somatic mutations (FIG. 19A). On the tested data, SAMtools produces the highest enrichment of true positives in a set of somatic mutations ranked by the FDR. However, we note that all tools offer many parameters and quality scores for the individual mutations. Here, we have used the default settings as specified by the algorithm developers; we expect that the parameters could be optimized and emphasize that the FDR framework defined here is designed for running and evaluating such an optimization.

For the described B16 sequencing experiment, we sequenced each sample in an individual flowcell lane and achieved a target region mean base coverage of 38 fold for the individual samples. However, this coverage might not be needed to obtain an equally good set of somatic mutations, possibly reducing costs. Also, the impact of the depth of caverage on whole genome SNV detection has been discussed recently [Ajay, S. S. et al., Genome Res. 21, 1498-1505 (2011)]. In order to study the effect of the coverage on exon capture data, we downsampled the number of aligned sequence reads for every 1×50 nt library to generate an approximate coverage of 5, 10 and 20 fold, respectively, and then reapplied the mutation call algorithms. As expected, a higher coverage results in a better (i.e. fewer false positives) somatic mutation set, although the improvement from the 20 fold coverage to the maximum is marginal (FIG. 19B).

It is straightforward to simulate and rank different experimental settings using the available data and framework. Comparing duplicates to triplicates, triplicates do not offer a benefit compared to the duplicates (FIG. 19C), while duplicates offer a clear improvement compared to a study without any replicates. In terms of the ratio of somatic mutations in the given sets, we see enrichment at a FDR of 5% from 24.2% for a run without replicates to 71.2% for duplicates and 85.8% for triplicates. Despite the enrichment, using the intersection of triplicates removes more mutations with a low FDR than ones with a high FDR, as indicated by the lower ROC AUC and the shift of the curve to the left (FIG. 19C): the specificity is slightly increased at the cost of a lower sensitivity.

The additionally sequenced 2×100 nt library was used to simulate a 1×100, two 2×50 and two 1×50 nt libraries, respectively, by in silico removal of the second read and/or the 3' and 5' ends of the reads, resulting in a total of 5 simulated libraries. These libraries were compared using the calculated FDRs of predicted mutations (FIG. 19D). Despite the much higher mean coverage (more than 77 vs. 38), the somatic mutations found using the 2×50 5' and 1×100 nt libraries have a lower ROC AUC and thus a worse FDR distribution than the 1×50 nt library. This phenomenon results from the accumulation of high FDR mutations in low coverage regions as the sets of low FDR mutations found are highly similar. The consequence is that the optimal sequencing length is either small so that the sequenced bases are concentrated around the capture probe sequences (potentially losing information on the somatic status of mutations in non-covered regions, though) or should be close to the fragment length (2×100 nt =200 nt total length for ~250 nt fragments in our case), effectively filling up the coverage gaps. This is also supported by the ROC AUC of the 2×50 nt 3' library (simulated by using only the 3' ends of the 2×100 nt library) which is higher than the one of the 2×50 nt 5' library (simulated by using only the 5' ends of the 2×100 nt library) despite the lower base quality of the 3' read ends.

These observations allow us to define best practice procedures for the discovery of somatic mutations. Across all evaluated parameters, 20 fold coverage in both samples and using a technical duplicate achieves close to the optimum results in these relatively homogeneous samples, while also considering costs. A 1×50 nt library resulting in approximately 100 million reads seems to be the most pragmatic choice to achieve this coverage. This remains true across all possible dataset pairings. We retrospectively applied those parameter settings, used no additional filtering of the raw variant calls, and calculated the FDRs for 50 selected mutations from the intersection of all three methods as shown in FIG. 17. All mutations were confirmed by a combination of Sanger resequencing and the B16 RNA-Seq sequence reads. 44 of those mutations would have been found using a FDR cutoff of 5% (FIG. 20). As a negative control, we re-sequenced the loci of 44 predicted mutations with high FDRs (>50%) and examined the respective sequences in the RNA-Seq data. We found 37 of these mutations to be not validated while the remaining seven loci of potential mutations were both not covered by RNA-Seq reads and yielded in not sequencing reaction.

While we show application of the framework to four specific questions, it is by no means limited to these parameters, but can be applied to study the influence of all experimental or algorithmic parameters, e.g. the influence of the alignment software, the choice of a mutation metric, or the choice of vendor for exome selection.

We performed all experiments on a set of B16 melanoma cell experiments; however, the method is not restricted to these data. The only requirement is the availability of a 'same-vs-same' reference data set, meaning at least a single technical repeat of a non-tumorous sample should be performed for each new protocol. While our experiments indicate that the method is robust with regard to the choice of the technical repeat within certain limits, so that a repeat is not necessarily required in every single experiment. However, the method does require that the various quality measures are comparable between the reference data set and remaining datasets.

Within this contribution, we have pioneered a statistical framework for a false-discovery-rate driven detection of somatic mutations. This framework is not only applicable for the diagnostic or therapeutic target selection, but also allows a generic comparison of experimental and computational protocol steps on a generated quasi ground truth data. Here, we applied this idea to make protocol decisions with regard to software tools, coverage, replicates as well as paired end sequencing.

Methods

Library Capture and Sequencing

Next-generation sequencing, DNA sequencing: Exome capture for DNA resequencing was performed using the Agilent Sure-Select solution-based capture assay [Gnirke, A., et al., *Nat. Biotechnol.* 27, 182-189 (2009)], in this case designed to capture all known mouse exons. 3 pg purified genomic DNA was fragmented to 150-200 nt using a Covaris S2 ultrasound device. gDNA fragments were end repaired using T4 DNA polymerase, Klenow DNA polymerase and 5' phosphorylated using T4 polynucleotide kinase. Blunt ended gDNA fragments were 3' adenylated using Klenow fragment (3' to 5' exo minus). 3' single T-overhang Illumina paired end adapters were ligated to the gDNA fragments using a 10:1 molar ratio of adapter to genomic DNA insert using T4 DNA ligase. Adapter ligated gDNA fragments were enriched pre capture and flow cell specific sequences were added using Illumina PE PCR primers 1.0 and 2.0 and Herculase II polymerase (Agilent) using 4 PCR cycles.

500 ng of adapter ligated, PCR enriched gDNA fragments were hybridized to Agilent's SureSelect biotinylated mouse whole exome RNA library baits for 24 hrs at 65° C. Hybridized gDNA/RNA bait complexes where removed using streptavidin coated magnetic beads. gDNA/RNA bait complexes were washed and the RNA baits cleaved off during elution in SureSelect elution buffer leaving the captured adapter ligated, PCR enriched gDNA fragments. gDNA fragments were PCR amplified post capture using Herculase II DNA polymerase (Agilent) and SureSelect GA PCR Primers for 10 cycles.

Cleanups were performed using 1.8× volume of AMPure XP magnetic beads (Agencourt). For quality controls we used Invitrogen's Qubit HS assay and fragment size was determined using Agilent's 2100 Bioanalyzer HS DNA assay.

Exome enriched gDNA libraries were clustered on the cBot using Truseq SR cluster kit v2.5 using 7 pM and sequenced on the Illumina HiSeq2000 using Truseq SBS kit.

Exome Data Analysis

Sequence reads were aligned using bwa (version 0.5.8c) [Li, H. Durbin, R., *Bioinformatics* 25, 1754-1760 (2009)] using default options to the reference mouse genome assembly mm9 (Mouse Genome Sequencing Consortium, Nature 420, 520-562 (2002)]. Ambiguous reads—those reads mapping to multiple locations of the genome as provided by the bwa output—were removed. The remaining alignments were sorted, indexed and converted to a binary and compressed format (BAM) and the read quality scores converted from the Illumina standard phred+64 to standard Sanger quality scores using shell scripts.

For each sequencing lane, mutations were identified using three software programs: SAMtools pileup (version 0.1.8) [Li, H. et al., *Bioinformatics* 25, 2078-2079 (2009)], GATK (version 1.0.4418) [DePristo, M. A. et al., *Nature Genetics* 43, 491-498 (2011)], and SomaticSniper [Ding, L. et al., *Hum. Mol. Genet* (2010) first published online Sep. 15, 2010]. For SAMtools, the author-recommend options and filter criteria were used (http://sourceforge.net/apys/mediawiki/SAMtools/index.pho?title=SAM FAO; accessed September 2011), including first round filtering, maximum coverage 200. For SAMtools second round filtering, the minimum indel quality score was 50, the point mutation minimum quality was 30. For GATK mutation calling, we followed the author-designed best practice guidelines presented on the GATK user manual (http://www.broadinstitute.or/gsa/wiki/index.php/The Genome Analysis Toolkit; accessed October 2010). For each sample a local realignment around indel sites followed by a base quality recalibration was performed. The UnifiedGenotyper module was applied to the resultant alignment data files. When needed, the known polymorphisms of the dbSNP [Sherry, S. T. et al., *Nucleic Acids Res.* 29, 308-311 (2009)] (version 128 for mm9) were supplied to the individual steps. The variant score recalibration step was omitted and replaced by the hard-filtering option. For SomaticSniper mutation calling, the default options were used and only predicted mutations with a "somatic score" of 30 or more were considered further. Additionally, for each potentially mutated locus we required a non-zero coverage in the normal tissue and removed all mutations located in repetitive sequences as defined by the RepeatMasker track of the UCSC Genome Browser for the mouse genome assembly mm9 [Fujita, P. A. et al., *Nucleic Acids Res.* 39, 876-882 (2011)].

RNA-Seq

Barcoded mRNA-seqcDNA libraries were prepared from 5 ug of total RNA using a modified version of the Illumina mRNA-seq protocol. mRNA was isolated using SeramagOligo(dT) magnetic beads (Thermo Scientific). Isolated mRNA was fragmented using divalent cations and heat resulting in fragments ranging from 160-200 bp. Fragmented mRNA was converted to cDNA using random primers and SuperScriptII (Invitrogen) followed by second strand synthesis using DNA polymerase I and RNaseH. cDNA was end repaired using T4 DNA polymerase, Klenow DNA polymerase and 5' phosphorylated using T4 polynucleotide kinase. Blunt ended cDNA fragments were 3' adenylated using Klenow fragment (3' to 5' exo minus). 3' single T-overhang Illumina multiplex specific adapters were ligated on the cDNA fragments using T4 DNA ligase. cDNA libraries were purified and size selected at 300 bp using the E-Gel 2% SizeSelect gel (Invitrogen). Enrichment, adding of Illumina six base index and flow cell specific sequences was done by PCR using Phusion DNA polymerase (Finnzymes). All cleanups were performed using 1.8× volume of Agencourt AMPure XP magnetic beads.

Barcoded RNA-seq libraries were clustered on the cBot using Truseq SR cluster kit v2.5 using 7 pM and sequenced on the Illumina HiSeq2000 using Truseq SBS kit.

The raw output data of the HiSeq was processed according to the Illumina standard protocol, including removal of low quality reads and demultiplexing. Sequence reads were then aligned to the reference genome sequence [Mouse Genome Sequencing Consortium, *Nature* 420, 520-562 (2002)] using bowtie [Langmead, B. et al., Genome Biol. 10, R25 (2009)]. The alignment coordinates were compared to the exon coordinates of the RefSeq transcripts [Pruitt, K. D. et al., *Nucleic Acids Res.* 33, 501-504 (2005)] and for each transcript the counts of overlapping alignments were recorded. Sequence reads not aligning to the genomic sequence were aligned to a database of all possible exon-exon junction sequences of the RefSeq transcripts [Pruitt, K. D. et al., *Nucleic Acids Res.* 33, 501-504 (2005)]. The alignment coordinates were compared to RefSeq exon and junction coordinates, reads counted, and normalized to RPKM (number of reads which map per nucleotide kilobase of transcript per million mapped reads [Mortazavi, A. et al., *Nat. Methods* 5, 621-628 (2008)]) for each transcript.

Validation of SNVs

We selected SNVs for validation by Sanger re-sequencing and RNA. SNVs were identified which were predicted by all three programs, non-synonymous, and found in transcripts having a minimum 10 RPKM. Of these, we selected the 50 with the highest SNP quality scores as provided by the programs. As a negative control, 44 SNVs were selected which have a FDR of 50% or more, are present in only one cell line sample and are predicted by only one mutation calling program. Using DNA, the selected variants were validated by PCR amplification of the regions using 50 ng of DNA, followed by Sanger sequencing (Eurofins MWG Operon, Ebersberg, Germany). The reactions were successful for 50 and 32 loci of positive and negative controls, respectively. Validation was also done by examination of the tumor RNA-Seq reads.

Calculation of FDRs and Machine Learning

Random Forest Quality Score Computation: Commonly-used mutation calling algorithms (DePristo, M. A. et al., *Nature Genetics* 43, 491-498 (2011), Li, H. et al., *Bioinformatics* 25, 2078-2079 (2009), Ding, L. et al., *Hum. Mol. Genet* (2010) first published online Sep. 15, 2010) output multiple scores, which all are potentially influencial for the quality of the mutation call. These include—but are not limited to—the quality of the base of interest as assigned by the instrument, the quality alignment for this position, the number of reads covering this position or a score for the difference between the two genomes compared at this position. For the computation of the false discovery rate we require an ordering of mutations, however this is not directly feasible for all mutations since we might have contradicting information from the various quality scores.

We use the following strategy to achieve a complete ordering. In a first step, we apply a very rigorous definition of superiority by assuming that a mutation has better quality than another if and only if it is superior in all categories. So a set of quality properties $S=(s_1, \ldots, s_n)$ is preferable to $T=(t_1, \ldots, t_n)$, denoted by $S>T$, if $s_i>t_i$ for all $i=1, \ldots, n$. We define an intermediate FDR (IFDR) as follows $$IFDR(T) = \frac{\#Same \; vs. \; Same \; SNVs \; with \; score \; S > T}{\#Tumor \; SNVs \; with \; score \; S > T} \times \frac{\#common \; coverage \; tumor \; comparison}{\#common \; coverage \; same \; vs. \; same \; comparison}$$

However, we regard the IFDR only as an intermediate step since in many closely related cases, no comparison is feasible and we are thus not benefitting from the vast amount of data available. Thus, we take advantage of the good generalization property of random forest regression [Breiman, L., Statist. Sci. 16, 199-231 (2001)] and train a random forest as implemented in R (R Development Core Team. R: A language and environment for statistical computing. R Foundation for Statistical Computing, Vienna, Austria, 2010, Liaw, A., Wiener, M., R News 2, 18-22 (2002)).

For m input mutations with n quality properties each, the value range for each property was determined and up top values were sampled with uniform spacing out of this range; when the set of values for a quality property was smaller than p, this set was used instead of the sampled set. Then each possible combination of sampled or selected quality values is created, which results in a maximum of $p^n$ data points in the n-dimensional quality space. A random sample of 1% of these points and the corresponding IFDR values were used as predictor and response, respectively, for the random forest training.

The resulting regression score is our generalized quality score Q; it can be regarded as a locally weighted combination of the individual quality scores. It allows direct, single value comparison of any two mutations and the computation of the actual false discovery rate:

$$FDR(Q) = \frac{\text{\#Same vs. Same SNVs with score} \geq Q}{\text{\#Tumor SNVs with score} \geq Q} \times \frac{\text{\#common coverage tumor comparison}}{\text{\#common coverage same vs. same comparison}}$$

For the training of the random forest model used to create the results for this study, we calculate the sample IFDR on the somatic mutations of all samples before selecting the random 1% subset. This ensures the mapping of the whole available quality space to FDR values. We used the quality properties "SNP quality", "coverage depth", "consensus quality" and "RMS mapping quality" (SAMtools, p=20); "SNP quality", "coverage depth", "Variant confidence/unfiltered depth" and "RMS mapping quality" (GATK, p=20); or SNP quality", "coverage depth", "consensus quality", "RMS mapping quality" and "somatic score" (SomaticSNiPer, p=12), respectively. The different values of p ensure a set size of comparable magnitude.

Common coverage computation: The number of possible mutation calls can introduce a major bias in the definition of a false discovery rate. Only if we have the same number of possible locations for mutations to occur for our tumor comparison and for our same vs. same comparison, the number of called mutations is comparable and can serve as a basis for a false discovery rate computation. To correct for this potential bias, we use the common coverage ratio. As common coverage we define the number of bases with coverage of at least one in both samples which are used for the mutation calling. We compute the common coverage individually for the tumor comparison as well as for the same vs. same comparison.

ROC Estimation

Receiver operating characteristic (ROC) curves and the corresponding area under curve (AUC) are useful for organizing classifiers and visualizing their performance [Fawcett, T., Pattern Recogn. Lett. 27, 861-874 (2006)]. We extend this concept for evaluating the performance of experimental and computational procedures. However, plotting ROC graphs requires knowledge of all true and false positive (TP and FP) examples in a dataset, information which is usually not given and hard to establish for high throughput data (such as NGS data). Thus, we use the calculated FDRs to estimate the respective TP and FP rates and plot a ROC graph and calculate an AUC. The central idea is that the FDR of a single mutation in the dataset gives the proportion how much this mutation contributes to the sum of TP/FP mutations, respectively. Also, for a list of random assignments to TP and FP, the resultant ROC AUC will be equal to 0.5 with our method, indicating a completely random prediction. We start with two conditions:

$$FDR = \frac{FPR}{FPR + TPR} \quad [1]$$

and $$FPR + TPR = 1 \quad [2]$$

with FPR and TPR being the needed false positive true positive ratios, respectively, for the given mutation, defining the corresponding point in ROC space. [1] and [2] can be rearranged to $$TPR = 1 - FPR \quad [3]$$

and $$FPR = FDR \quad [4]$$

To obtain an estimated ROC curve, the mutations in dataset are sorted by FDR and for each mutation a point is plotted at the cumulative TPR and FPR values up to this mutation, divided by the sum of all TPR and TPR values, respectively. The AUC is calculated by summing up the areas of all consecutive trapezoids between the curve and the x-axis.

The invention claimed is:

1. A method for treating cancer by:
administering to an individual with a tumor an individualized cancer vaccine comprising RNA encoding a recombinant polyepitopic polypeptide, wherein the polypeptide comprises two or more immunogenic neo-epitopes identified from a sample comprising tumor cells from the individual, wherein each immunogenic neo-epitope is characterized by each of the following characteristics:
 (i) occurs in a transcript;
 (ii) occurs in a protein-coding region;
 (iii) introduces a change in amino acid sequence; and
 (iv) is predicted to exhibit WIC binding;
wherein following the administration, the individualized cancer vaccine elicits a T cell response against the tumor of the individual.

2. The method of claim 1, wherein the individualized cancer vaccine was produced by a process comprising steps of:
 (a) obtaining nucleic acid sequence information from a sample comprising tumor cells from the individual;
 (b) obtaining nucleic acid sequence information from a sample comprising non-tumor cells from the same individual;
 (c) comparing the tumor cell sequence information with the non-tumor-cell sequence information so that somatic mutations present in the tumor cell sequence information are identified;
 (d) classifying as immunogenic neo-epitopes at least two of the identified somatic mutations characterized by each of the characteristics; and
 (e) producing a nucleic acid vaccine comprising RNA encoding a recombinant polyepitopic polypeptide, wherein the polypeptide comprises two or more immunogenic neo-epitopes identified in steps (a)-(d) and the neo-epitopes are fused together by peptide bonds or linkers.

3. The method of claim 2, wherein the step of obtaining nucleic acid sequence information from the sample comprising tumor cells from the individual comprises single cell sequencing of one or more tumor cells from the individual.

4. The method of claim 3, wherein the tumor cells are or comprise circulating tumor cells.

5. The method of claim 2, wherein the tumor cell and/or non-tumor-cell sequence information is or comprises genomic, transcriptome, and/or exome sequence information.

6. The method of claim 1, wherein the recombinant polyepitopic polypeptide encoded by the RNA comprises 10 or more neo-epitopes.

7. The method of claim 1, wherein the recombinant polyepitopic polypeptide encoded by the RNA further comprises one or more epitopes that are expressed by that individual's tumor, which epitopes do not contain the tumor-specific somatic mutation(s) of the neo-epitopes.

8. The method of claim 1, wherein RNA encoding a vaccine sequence of each neo-epitope is or comprises a RNA sequence encoding (i) respective somatic mutation(s) and (ii) its epitope flanking regions as present in a respective naturally occurring protein.

9. The method of claim 8, wherein the vaccine sequence of each neo-epitope encoded by the RNA comprises 20 or more amino acids.

10. The method of claim 1, wherein the neo-epitopes encoded by the RNA are arranged in a head-to-tail configuration.

11. The method of claim 1, wherein the RNA encoding the recombinant polyepitopic polypeptide comprises a linker sequence between each of the encoded neo-epitopes.

12. The method of claim 11, wherein the linker sequence encodes a peptide linker characterized in that at least 60% of amino acids of the peptide linker are glycine and serine residues.

13. The method of claim 1, wherein one or more of the neo-epitopes comprises at least one primary basal mutation.

14. The method of claim 2, wherein the nucleic acid sequence information from the sample comprising non-tumor cells is obtained from genomic germline DNA from peripheral blood mononuclear cells (PBMCs).

15. The method of claim 1, wherein the RNA comprises:
an unmasked poly-A sequence; a 3'-non translated region (UTR); an MHC class I signal peptide fragment and transmembrane and cytosolic domains including the stop codon; a 5' cap; or combinations thereof.

16. The method of claim 1, wherein the RNA comprises an unmasked poly-A sequence having a length of approximately 120 adenosine residues.

17. The method of claim 1, wherein the RNA comprises a 5' cap that is or comprises:

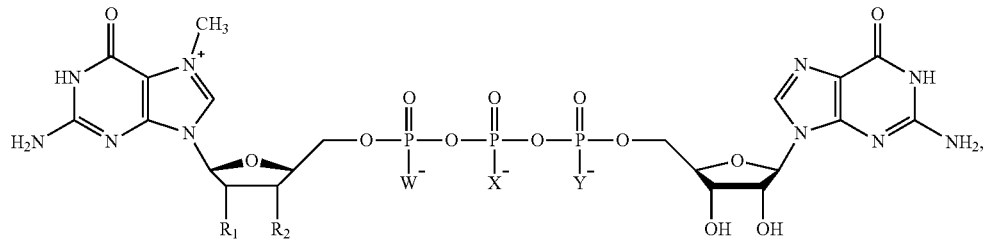

wherein $R_1$ and $R_2$ are independently hydroxy or methoxy, and W, X, and Y are independently oxygen, sulfur, selenium or $BH_3$.

18. The method of claim 17, wherein the 5' cap is or comprises $m_2^{7,2'-O} Gpp_s pG$.

19. The method of claim 1, wherein the individualized cancer vaccine is administered in combination with a cancer therapeutic regimen.

* * * * *

UNITED STATES PATENT AND TRADEMARK OFFICE
CERTIFICATE OF CORRECTION

PATENT NO. : 11,248,264 B2
APPLICATION NO. : 16/920286
DATED : February 15, 2022
INVENTOR(S) : Ugur Sahin et al.

It is certified that error appears in the above-identified patent and that said Letters Patent is hereby corrected as shown below:

In the Claims

In Claim 1, Column 99, Line 56, replace "WIC" with --MHC--.

Signed and Sealed this
Fourteenth Day of June, 2022

Katherine Kelly Vidal
*Director of the United States Patent and Trademark Office*

SEQUENCE LISTING

```
<160> NUMBER OF SEQ ID NOS: 39

<210> SEQ ID NO 1
<211> LENGTH: 15
<212> TYPE: PRT
<213> ORGANISM: Artificial Sequence
<220> FEATURE:
<223> OTHER INFORMATION: Linker sequence
<220> FEATURE:
<221> NAME/KEY: REPEAT
<222> LOCATION: (1)..(3)
<223> OTHER INFORMATION: Portion of sequence repeated a times, wherein a
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: MISC_FEATURE
<222> LOCATION: (1)..(15)
```

```
<223> OTHER INFORMATION: a + b + c + d + e are different from 0 and
      preferably are 2 or more, 3 or more, 4 or more or 5 or more
<220> FEATURE:
<221> NAME/KEY: REPEAT
<222> LOCATION: (4)..(6)
<223> OTHER INFORMATION: Portion of sequence repeated b times, wherein b
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: REPEAT
<222> LOCATION: (7)..(9)
<223> OTHER INFORMATION: Portion of sequence repeated c times, wherein c
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: REPEAT
<222> LOCATION: (10)..(12)
<223> OTHER INFORMATION: Portion of sequence repeated d times, wherein d
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: REPEAT
<222> LOCATION: (13)..(15)
<223> OTHER INFORMATION: Portion of sequence repeated e times, wherein e
      is independently a number selected from 0, 1, 2, 3, 4, 5, 6, 7, 8,
      9, 10, 11, 12, 13, 14, 15, 16, 17, 18, 19, or 20

<400> SEQUENCE: 1

Gly Gly Ser Gly Ser Ser Gly Gly Gly Ser Ser Gly Gly Ser Gly
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Linker sequence

<400> SEQUENCE: 2

Gly Gly Ser Gly Gly Gly Gly Ser Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Epitope sequence

<400> SEQUENCE: 3

Ser Ile Ile Asn Phe Glu Lys Leu
1               5

<210> SEQ ID NO 4
<211> LENGTH: 30
<212> TYPE: PRT
<213> ORGANISM: Artificial Sequence
<220> FEATURE:
<223> OTHER INFORMATION: Mutated peptide sequence

<400> SEQUENCE: 4

Ser Pro Ser Lys Pro Ser Phe Gln Glu Phe Val Asp Trp Glu Asn Val
1               5                   10                  15

Ser Pro Glu Leu Asn Ser Thr Asp Gln Pro Phe Leu Pro Ser
            20                  25                  30

<210> SEQ ID NO 5
<211> LENGTH: 30
<212> TYPE: PRT
<213> ORGANISM: Artificial Sequence
```

```
<220> FEATURE:
<223> OTHER INFORMATION: Wildtype peptide sequence

<400> SEQUENCE: 5

Ser Pro Ser Lys Pro Ser Phe Gln Glu Phe Val Asp Trp Glu Lys Val
1               5                   10                  15

Ser Pro Glu Leu Asn Ser Thr Asp Gln Pro Phe Leu Pro Ser
            20                  25              30

<210> SEQ ID NO 6
<211> LENGTH: 27
<212> TYPE: PRT
<213> ORGANISM: Artificial Sequence
<220> FEATURE:
<223> OTHER INFORMATION: Mutated peptide sequence

<400> SEQUENCE: 6

Thr Pro Pro Pro Glu Glu Ala Met Pro Phe Glu Phe Asn Gly Pro Ala
1               5                   10                  15

Gln Gly Asp His Ser Gln Pro Pro Leu Gln Val
            20                  25

<210> SEQ ID NO 7
<211> LENGTH: 27
<212> TYPE: PRT
<213> ORGANISM: Artificial Sequence
<220> FEATURE:
<223> OTHER INFORMATION: Wildtype peptide sequence

<400> SEQUENCE: 7

Thr Pro Pro Pro Glu Glu Ala Met Pro Phe Glu Phe Asn Glu Pro Ala
1               5                   10                  15

Gln Gly Asp His Ser Gln Pro Pro Leu Gln Val
            20                  25

<210> SEQ ID NO 8
<211> LENGTH: 27
<212> TYPE: PRT
<213> ORGANISM: Artificial Sequence
<220> FEATURE:
<223> OTHER INFORMATION: Mutated peptide sequence

<400> SEQUENCE: 8

Arg Val Thr Cys Asn Arg Ala Gly Glu Lys His Cys Phe Ser Ser Asn
1               5                   10                  15

Glu Ala Ala Arg Asp Phe Gly Gly Ala Ile Gln
            20                  25

<210> SEQ ID NO 9
<211> LENGTH: 27
<212> TYPE: PRT
<213> ORGANISM: Artificial Sequence
<220> FEATURE:
<223> OTHER INFORMATION: Wildtype peptide sequence

<400> SEQUENCE: 9

Arg Val Thr Cys Asn Arg Ala Gly Glu Lys His Cys Phe Thr Ser Asn
1               5                   10                  15

Glu Ala Ala Arg Asp Phe Gly Gly Ala Ile Gln
            20                  25

<210> SEQ ID NO 10
<211> LENGTH: 27
<212> TYPE: PRT
```

```
<213> ORGANISM: Artificial Sequence
<220> FEATURE:
<223> OTHER INFORMATION: Mutated peptide sequence

<400> SEQUENCE: 10

Phe Arg Arg Lys Ala Phe Leu His Trp Tyr Thr Gly Glu Ala Met Asp
1               5                   10                  15

Glu Met Glu Phe Thr Glu Ala Glu Ser Asn Met
            20                  25

<210> SEQ ID NO 11
<211> LENGTH: 27
<212> TYPE: PRT
<213> ORGANISM: Artificial Sequence
<220> FEATURE:
<223> OTHER INFORMATION: Wildtype peptide sequence

<400> SEQUENCE: 11

Phe Arg Arg Lys Ala Phe Leu His Trp Tyr Thr Gly Glu Gly Met Asp
1               5                   10                  15

Glu Met Glu Phe Thr Glu Ala Glu Ser Asn Met
            20                  25

<210> SEQ ID NO 12
<211> LENGTH: 27
<212> TYPE: PRT
<213> ORGANISM: Artificial Sequence
<220> FEATURE:
<223> OTHER INFORMATION: Mutated peptide sequence

<400> SEQUENCE: 12

Pro Ser Lys Pro Ser Phe Gln Glu Phe Val Asp Trp Glu Asn Val Ser
1               5                   10                  15

Pro Glu Leu Asn Ser Thr Asp Gln Pro Phe Leu
            20                  25

<210> SEQ ID NO 13
<211> LENGTH: 27
<212> TYPE: PRT
<213> ORGANISM: Artificial Sequence
<220> FEATURE:
<223> OTHER INFORMATION: Wildtype peptide sequence

<400> SEQUENCE: 13

Pro Ser Lys Pro Ser Phe Gln Glu Phe Val Asp Trp Glu Lys Val Ser
1               5                   10                  15

Pro Glu Leu Asn Ser Thr Asp Gln Pro Phe Leu
            20                  25

<210> SEQ ID NO 14
<211> LENGTH: 27
<212> TYPE: PRT
<213> ORGANISM: Artificial Sequence
<220> FEATURE:
<223> OTHER INFORMATION: Mutated peptide sequence

<400> SEQUENCE: 14

His Leu Thr Gln Gln Leu Asp Thr Tyr Ile Leu Lys Asn Val Val Ala
1               5                   10                  15

Phe Ser Arg Thr Asp Lys Tyr Arg Gln Leu Pro
            20                  25

<210> SEQ ID NO 15
<211> LENGTH: 27
```

```
<212> TYPE: PRT
<213> ORGANISM: Artificial Sequence
<220> FEATURE:
<223> OTHER INFORMATION: Wildtype peptide sequence

<400> SEQUENCE: 15

His Leu Thr Gln Gln Leu Asp Thr Tyr Ile Leu Lys Asn Phe Val Ala
1               5                   10                  15

Phe Ser Arg Thr Asp Lys Tyr Arg Gln Leu Pro
            20                  25

<210> SEQ ID NO 16
<211> LENGTH: 27
<212> TYPE: PRT
<213> ORGANISM: Artificial Sequence
<220> FEATURE:
<223> OTHER INFORMATION: Mutated peptide sequence

<400> SEQUENCE: 16

Cys Gly Thr Ala Phe Phe Ile Asn Phe Ile Ala Ile Tyr His His Ala
1               5                   10                  15

Ser Arg Ala Ile Pro Phe Gly Thr Met Val Ala
            20                  25

<210> SEQ ID NO 17
<211> LENGTH: 27
<212> TYPE: PRT
<213> ORGANISM: Artificial Sequence
<220> FEATURE:
<223> OTHER INFORMATION: Wildtype peptide sequence

<400> SEQUENCE: 17

Cys Gly Thr Ala Phe Phe Ile Asn Phe Ile Ala Ile Tyr Tyr His Ala
1               5                   10                  15

Ser Arg Ala Ile Pro Phe Gly Thr Met Val Ala
            20                  25

<210> SEQ ID NO 18
<211> LENGTH: 7
<212> TYPE: PRT
<213> ORGANISM: Artificial Sequence
<220> FEATURE:
<223> OTHER INFORMATION: Linker sequence

<400> SEQUENCE: 18

Gly Gly Ser Gly Gly Gly Gly
1               5

<210> SEQ ID NO 19
<211> LENGTH: 10
<212> TYPE: PRT
<213> ORGANISM: Artificial Sequence
<220> FEATURE:
<223> OTHER INFORMATION: Linker sequence

<400> SEQUENCE: 19

Thr Ser Leu Asn Ala Leu Leu Asn Ala His
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Linker sequence
```

```
<400> SEQUENCE: 20

Ser Ser Ser Ser Ser Ser Ser Ser Ser
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Linker sequence

<400> SEQUENCE: 21

Gly Gly Gly Gly Gly Gly Gly Gly Gly Gly
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Linker sequence

<400> SEQUENCE: 22

Gly Gly Ser Gly Gly Gly Gly Ser Gly Gly
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Linker sequence

<400> SEQUENCE: 23

Gly Gly Ser Gly Gly Gly Ser Gly Gly Gly
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Linker sequence

<400> SEQUENCE: 24

Thr Ser Leu Asn Ala Leu Leu Asn Ala
1               5

<210> SEQ ID NO 25
<211> LENGTH: 9
<212> TYPE: PRT
<213> ORGANISM: Artificial Sequence
<220> FEATURE:
<223> OTHER INFORMATION: Linker sequence

<400> SEQUENCE: 25

Ser Ser Ser Ser Ser Ser Ser Ser Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Linker sequence

<400> SEQUENCE: 26
```

Gly Gly Gly Gly Gly Gly Gly Gly Gly
1               5

<210> SEQ ID NO 27
<211> LENGTH: 9
<212> TYPE: PRT
<213> ORGANISM: Artificial Sequence
<220> FEATURE:
<223> OTHER INFORMATION: Linker sequence

<400> SEQUENCE: 27

Gly Gly Ser Gly Gly Gly Ser Gly Gly
1               5

<210> SEQ ID NO 28
<211> LENGTH: 5
<212> TYPE: PRT
<213> ORGANISM: Artificial Sequence
<220> FEATURE:
<223> OTHER INFORMATION: Linker sequence

<400> SEQUENCE: 28

Gly Gly Ser Gly Gly
1               5

<210> SEQ ID NO 29
<211> LENGTH: 6
<212> TYPE: PRT
<213> ORGANISM: Artificial Sequence
<220> FEATURE:
<223> OTHER INFORMATION: Linker sequence

<400> SEQUENCE: 29

Gly Gly Ser Gly Gly Gly
1               5

<210> SEQ ID NO 30
<211> LENGTH: 7
<212> TYPE: PRT
<213> ORGANISM: Artificial Sequence
<220> FEATURE:
<223> OTHER INFORMATION: Linker sequence

<400> SEQUENCE: 30

Gly Gly Ser Gly Gly Gly Gly
1               5

<210> SEQ ID NO 31
<211> LENGTH: 8
<212> TYPE: PRT
<213> ORGANISM: Artificial Sequence
<220> FEATURE:
<223> OTHER INFORMATION: Linker sequence

<400> SEQUENCE: 31

Gly Gly Ser Gly Gly Gly Gly Ser
1               5

<210> SEQ ID NO 32
<211> LENGTH: 10
<212> TYPE: PRT
<213> ORGANISM: Artificial Sequence
<220> FEATURE:
<223> OTHER INFORMATION: Linker sequence

<400> SEQUENCE: 32

Gly Gly Ser Gly Gly Gly Ser Gly Gly Ser
1               5                   10

<210> SEQ ID NO 33
<211> LENGTH: 14
<212> TYPE: DNA
<213> ORGANISM: Artificial Sequence
<220> FEATURE:
<223> OTHER INFORMATION: Oligonucleotide

<400> SEQUENCE: 33
ggaaactttt tccc                                              14

<210> SEQ ID NO 34
<211> LENGTH: 21
<212> TYPE: DNA
<213> ORGANISM: Artificial Sequence
<220> FEATURE:
<223> OTHER INFORMATION: Oligonucleotide

<400> SEQUENCE: 34
ccggggaaac ttttcccag t                                       21

<210> SEQ ID NO 35
<211> LENGTH: 21
<212> TYPE: DNA
<213> ORGANISM: Artificial Sequence
<220> FEATURE:
<223> OTHER INFORMATION: Oligonucleotide

<400> SEQUENCE: 35
ccggggaaac gttttcccag t                                      21

<210> SEQ ID NO 36
<211> LENGTH: 60
<212> TYPE: PRT
<213> ORGANISM: Artificial Sequence
<220> FEATURE:
<223> OTHER INFORMATION: Artificial construct

<400> SEQUENCE: 36

Asn Thr Thr Phe Asn Val Ser Glu Glu Ser Pro Ser Lys Pro Ser Phe
1               5                   10                  15

Gln Glu Phe Val Asp Trp Glu Asn Val Ser Pro Glu Leu Asn Ser Thr
                20                  25                  30

Asp Gln Pro Phe Leu Pro Ser Ala Pro Val Phe Ile Phe Thr Lys Gly
            35                  40                  45

Arg Lys Gly Gly Ser Gly Gly Gly Ser Gly Gly
        50                  55                  60

<210> SEQ ID NO 37
<211> LENGTH: 60
<212> TYPE: PRT
<213> ORGANISM: Artificial Sequence
<220> FEATURE:
<223> OTHER INFORMATION: Artificial construct

<400> SEQUENCE: 37

Tyr Phe Val Leu Tyr Lys Pro Pro Lys Asp Asn Ile Pro Ala Leu
1               5                   10                  15

Val Glu Glu Tyr Leu Glu Arg Gly Asn Phe Val Ala Asn Asp Leu Asp
                20                  25                  30

Trp Leu Leu Ala Leu Pro His Asp Lys Phe Trp Cys Gln Val Ile Phe
            35                  40                  45

```
Asp Glu Gly Gly Ser Gly Gly Ser Gly Gly Ser
    50                  55                  60

<210> SEQ ID NO 38
<211> LENGTH: 60
<212> TYPE: PRT
<213> ORGANISM: Artificial Sequence
<220> FEATURE:
<223> OTHER INFORMATION: Artificial construct

<400> SEQUENCE: 38

Phe Glu Gln Leu Ser Glu Ser Ala Lys Glu Glu Leu Ile Asn Phe Lys
1               5                   10                  15

Arg Lys Arg Val Ala Ala Phe Gln Lys Asn Leu Ile Glu Met Ser Glu
            20                  25                  30

Leu Glu Ile Lys His Ala Arg Asn Asn Val Ser Leu Leu Gln Ser Cys
        35                  40                  45

Ile Asp Gly Gly Ser Gly Gly Gly Ser Gly Gly
    50                  55              60

<210> SEQ ID NO 39
<211> LENGTH: 60
<212> TYPE: PRT
<213> ORGANISM: Artificial Sequence
<220> FEATURE:
<223> OTHER INFORMATION: Artificial construct

<400> SEQUENCE: 39

Thr Gly Ala Ser Pro Gly Leu Gly Ala Tyr Thr Pro Pro Glu Glu
1               5                   10                  15

Ala Met Pro Phe Glu Phe Asn Gly Pro Ala Gln Gly Asp His Ser Gln
            20                  25                  30

Pro Pro Leu Gln Val Pro Asp Leu Ala Pro Gly Gly Pro Glu Ala Leu
        35                  40                  45

Val Pro Gly Gly Ser Gly Gly Gly Ser Gly Gly Ser
    50                  55                  60
```